US012054550B2

(12) United States Patent
Zhukovsky et al.

(10) Patent No.: US 12,054,550 B2
(45) Date of Patent: *Aug. 6, 2024

(54) BISPECIFIC ANTIBODIES TARGETING EGFR AND HER2

(71) Applicants: BIOMUNEX PHARMACEUTICALS, Paris (FR); INSERM (INSTITUT NATIONAL DE LA SANTE ET DE LA RECHERCHE MEDICALE), Paris (FR); UNIVERSITE DE MONTPELLIER, Montpellier (FR); INSTITUT REGIONAL DU CANCER DE MONTPELLIER (ICM), Montpellier (FR)

(72) Inventors: Eugene Zhukovsky, Paris (FR); Olivier Leger, Saint Sixt (FR); Pierre-Emmanuel Gerard, Paris (FR); Andre Pelegrin, Paris (FR); Christel Larbouret, Paris (FR)

(73) Assignees: BIOMUNEX PHARMACEUTICALS, Paris (FR); INSERM (INSTITUT NATIONAL DE LA SANTE ET DE LA RECHERCHE MEDICALE), Paris (FR); UNIVERSITE DE MONTPELLIER, Montpellier (FR); INSTITUT REGIONAL DU CANCER DE MONTPELLIER (ICM), Motpellier (FR)

(*) Notice: Subject to any disclaimer, the term of this patent is extended or adjusted under 35 U.S.C. 154(b) by 0 days.

This patent is subject to a terminal disclaimer.

(21) Appl. No.: 16/096,698

(22) PCT Filed: Apr. 28, 2017

(86) PCT No.: PCT/EP2017/060280
§ 371 (c)(1),
(2) Date: Oct. 26, 2018

(87) PCT Pub. No.: WO2017/186950
PCT Pub. Date: Nov. 2, 2017

(65) Prior Publication Data
US 2019/0153104 A1 May 23, 2019

(51) Int. Cl.
*C07K 16/28* (2006.01)
*A61P 35/00* (2006.01)
*C07K 16/46* (2006.01)
*A61K 38/00* (2006.01)

(52) U.S. Cl.
CPC .......... C07K 16/2863 (2013.01); A61P 35/00 (2018.01); C07K 16/468 (2013.01); *A61K 38/00* (2013.01); *C07K 2317/51* (2013.01); *C07K 2317/515* (2013.01); *C07K 2317/53* (2013.01); *C07K 2317/73* (2013.01)

(58) Field of Classification Search
CPC .............. C07K 16/468; C07K 16/2863; C07K 2317/60
USPC ....................................................... 424/136.1
See application file for complete search history.

(56) References Cited

U.S. PATENT DOCUMENTS

| 9,631,031 | B2 | 4/2017 | Kadouche et al. | |
| 10,633,456 | B1* | 4/2020 | Boyd-Kirkup | C07K 16/2827 |
| 10,662,241 | B1* | 5/2020 | Boyd-Kirkup | C07K 14/7051 |
| 10,815,310 | B2 | 10/2020 | Kadouche et al. | |
| 11,046,776 | B2* | 6/2021 | Lazar | C07K 16/2878 |
| 11,560,437 | B2* | 1/2023 | Zhukovsky | C07K 16/2827 |
| 2002/0004587 | A1 | 1/2002 | Miller et al. | |
| 2014/0113348 | A1 | 4/2014 | Williams et al. | |
| 2018/0057598 | A1* | 3/2018 | Lazar | A61P 17/00 |
| 2019/0300610 | A1* | 10/2019 | Boyd-Kirkup | A61P 35/04 |
| 2019/0300624 | A1* | 10/2019 | Boyd-Kirkup | C07K 16/28 |
| 2019/0330377 | A1* | 10/2019 | Zhukovsky | C07K 16/2896 |
| 2020/0010559 | A1* | 1/2020 | Zhukovsky | C07K 16/2896 |
| 2020/0283524 | A1* | 9/2020 | Xu | C07K 14/7051 |
| 2020/0299413 | A1 | 9/2020 | Zhukovsky et al. | |
| 2020/0308275 | A1* | 10/2020 | Boyd-Kirkup | C07K 14/7051 |
| 2020/0308308 | A1* | 10/2020 | Boyd-Kirkup | C07K 16/464 |
| 2021/0024651 | A1* | 1/2021 | Boyd-Kirkup | C07K 14/7051 |
| 2021/0155712 | A1* | 5/2021 | Boyd-Kirkup | C07K 16/32 |

FOREIGN PATENT DOCUMENTS

| CA | 2 929 256 | 5/2015 |
| JP | 2014-522644 | 9/2014 |
| JP | 2016-509014 | 3/2016 |
| WO | WO 2012/088461 | 6/2012 |
| WO | WO 2012/131555 | 10/2012 |

(Continued)

OTHER PUBLICATIONS

Worn and Pluckthun (J. Mol. Biol. 305:989-1010 (2001)).*

(Continued)

Primary Examiner — Lynn A Bristol
(74) Attorney, Agent, or Firm — SALIWANCHIK, LLOYD & EISENSCHENK

(57) ABSTRACT

The present disclosure relates to bispecific antibodies targeting EGFR and HER2, and methods for the production of these antibodies. The bispecific antibodies consist of one complete antibody on which two VH-VL chains are attached via a linker to each NH terminal region of both VH chains of the antibody. The bispecific antibodies constructed use the amino acid sequences of the heavy chain (VH) and the light chain (VL) variable regions of two monoclonal antibodies targeting EGFR and HER2, namely cetuximab and trastuzumab, respectively.

10 Claims, 8 Drawing Sheets
Specification includes a Sequence Listing.

(56) References Cited

FOREIGN PATENT DOCUMENTS

| WO | WO 2013/005194 | 1/2013 |
|---|---|---|
| WO | WO 2014/028776 | 2/2014 |
| WO | WO 2014/124326 | 8/2014 |
| WO | WO 2015/149077 | 10/2015 |
| WO | WO 2015/173756 | 11/2015 |
| WO | WO 2016/014974 | 1/2016 |
| WO | WO 2016/172485 | 10/2016 |
| WO | WO 2017/162890 | 9/2017 |
| WO | WO 2018/127608 | 7/2018 |
| WO | WO 2018/178101 | 10/2018 |

OTHER PUBLICATIONS

Wang et al. (Cancer Letters 325 214-219 (2012)).*
https://clinicaltrials.gov/ct2/show/NCT00551421 pp. 1-12 (Aug. 11, 2021).*
Biotechnology, Chemical, Pharmaceutical (BCP) Partnership Meeting (SPE Dan Kolker, Sep. 17, 2020; pp. 1-36).*
Rudikoff et al (Proc Natl Acad Sci USA 1982 vol. 79 p. 1979).*
Brinkman et al (MABS vol. 9, No. 2, 182-212 (2017,)).*
Wang S et al. (Cancer Lett 325(2):214-9 (Dec. 28, 2012)).*
ClinicalTrials.gov Identifier: NCT00923299 (pp. 1-7; Jun. 18, 2009).*
Assenat, E. et al. "Dual targeting of HER1/EGFR and HER2 with cetuximab and trastuzumab in patients with metastatic pancreatic cancer after gemcitabine failure: results of the "Therapy" phase 1-2 trial" Oncotarget, Feb. 28, 2015, pp. 12796-12808, vol. 6, No. 14.
Wu, X. et al. "Fab-based bispecific antibody formats with robust biophysical properties and biological activity" mAbs, May/Jun. 2015, pp. 470-482, vol. 7, Issue 3.
Written Opinion in International Application No. PCT/EP2017/060280, Jul. 4, 2017, pp. 1-8.
Genmab, "Genmab Announces Studies of Daratumumab in Combination with Atezolizumab in a Solid Tumor and Multiple Myeloma" Company Announcement No. 15, Mar. 21, 2016, retrieved from the Internet on Jun. 1, 2017: URL:https://www.clinicalleader.com/doc/genmab-announces-studies-of-daratumumab-in-combination-with-atezolizumab-0001, pp. 1-2.
Moore, G. L. et al. "1798 Tuning T Cell Affinity Improves Efficacy and Safety of Anti-CD38×Anti-CD3 Bispecific Antibodies in Monkeys—a Potential Therapy for Multiple Myeloma" presented Dec. 5, 2015, 57th Annual Meeting & Exposition, Orlando, Florida, pp. 1-3, retrieved from Internet on Jun. 1, 2017: URL:https://ash.confex.com/ash/2015/webprogramscheduler/Paper78382.html.
Written Opinion in International Application No. PCT/EP2017/057220, Jun. 26, 2017, pp. 1-6.
Chu, S. Y. et al. "Immunotherapy with Long-Lived Anti-CD38×Anti-CD3 Bispecific Antibodies Simulates Potent T Cell-Mediated Killing of Human Myeloma Cell Lines and CD38+ Cells in Monkeys: A Potential Therapy for Multiple Myeloma" 2014, p. 1.
Lloyd, C. et al., "Modelling the human immune response: performance of a $10^{11}$ human antibody repertoire against a broad panel of therapeutically relevant antigens" Protein Engineering Design & Selection, 2009, vol. 22, pp. 159-168.
Edwards, B. M. et al., "The Remarkable Flexibility of the Human Antibody Repertoire; Isolation of Over One Thousand Different Antibodies to a Single Protein, BLyS" J Mol Biol., 2003, vol. 14, No. 334(1), pp. 103-118.
Goel, M. et al., "Plasticity within the Antigen-Combining Site May Manifest as Molecular Mimicry in the Humoral Immune Response" The Journal of Immunology, 2004, vol. 173, No. 12, pp. 7358-7367.
Malia, T. J. et al., "Epitope mapping and structural basis for the recognition of phosphorylated tau by the anti-tau antibody AT8" Proteins, 2016, vol. 84, pp. 427-434.

Barthelemy, P. A. et al., "Comprehensive Analysis of the Factors Contributing to the Stability and Solubility of Autonomous Human $V_H$ Domains" Journal of Biological Chemistry, 2008, vol. 283, pp. 3639-3654.
Beiboer, S. H. W. et al., "Guided Selection of a Pan Carcinoma Specific Antibody Reveals Similar Binding Characteristics yet Structural Divergence Between the Original Murine Antibody and its Human Equivalent" Journal of Molecular Biology, 2000, vol. 296, pp. 833-849.
Choi, Y. et al., "Predicting antibody complementarity determining region structures without classification" Molecular Biosystems, 2011, vol. 7, pp. 3327-3334.
De Genst, E. et al., "Antibody repertoire development in camelids" Developmental and Comparative Immunology, 2006, vol. 30, pp. 187-198.
Griffiths, A. D. et al., "Human anti-self antibodies with high specificity from phage display libraries" The EMBO Journal, 1993, vol. 12, pp. 725-734.
Klimka, A. et al., "Human anti-CD30 recombinant antibodies by guided phage antibody selection using cell panning" British Journal of Cancer, 2000, vol. 83, pp. 252-260.
Ward, E. S. et al. "Binding activities of a repertoire of single immunoglobulin variable domains secreted from Escherichia coli" Nature, 1989, vol. 341, pp. 544-546.
Holm, P. et al., "Functional mapping and single chain construction of the anti-cytokeratin 8 monoclonal antibody TS1" Mol. Immunol., Feb. 2007, vol. 44 No. 6, pp. 1075-1084.
Maccallum, R. M. et al., "Antibody-antigen Interactions: Contact Analysis and Binding Site Topography" J. Mol. Biol., Oct. 11, 1996, vol. 262, No. 5, pp. 732-745.
Golay, J. et al. "Design and Validation of a Novel Generic Platform for the Production of Tetravalent IgG1-like Bispecific Antibodies" The Journal of Immunology, Apr. 1, 2016, pp. 3199-3211, vol. 196, No. 7, supplemental p. 1.
Written Opinion in International Application No. PCT/EP2018/050481, Mar. 26, 2018, pp. 1-10.
Chen, X. et al. "Fusion Protein Linkers: Property, Design and Functionality" Adv Drug Deliv Rev., Oct. 15, 2013, vol. 65, No. 10, pp. 1357-1369.
Reusch, U. et al. "A tetravalent bispecific TandAb (CD19/CD3), AFM 11, efficiently recruits T cells for the potent lysis of CD19+ tumor cells" MAbs, May-Jun. 2015, vol. 7, No. 3, pp. 584-604.
Genmab Press Release, "Genmab Announces Studies of Daratumumab in Combination with Atezolizumab in a Solid Tumor and Multiple Myeloma" Mar. 21, 2016, pp. 1-2, retrieved from Internet: http://files.shareholder.com/downloads/AMDA-KPIBN/0x0x882184/5D77EB62-231D-41DA-9416-39D816CF878C/15_Dara%20atezolizumab%20combo_210316_uk.pdf.
Mazor, Y. et al. "Enhanced tumor-targeting selectivity by modulating bispecific antibody binding affinity and format valence" Scientific Reports, Jan. 9, 2017, pp. 1-11, vol. 7.
Written Opinion in International Application No. PCT/EP2018/057819, Jul. 24, 2018, pp. 1-11.
Debiec, K. T. et al. "Evaluating the Strength of Salt Bridges: a Comparison of Current Biomolecular Force Fields" J. Phys. Chem. B., 2014, pp. 6561-6569, vol. 118.
Meuzelaar, H. et al. Biophysical Journal, Jul. 7, 2016, vol. 110, pp. 2328-2341.
Hu, S. et al., "Four-in-One Antibodies Have Superior Cancer Inhibitory Activity against EGFR, HER2, HER3, and VEGF through Disruption of HER/MET Crosstalk" Cancer Res., 75(1):1-14; Jan. 1, 2015; Published Online First Nov. 4, 2014.
Magdelaine-Beuzelin, C. et al. "Structure-function relationships of the variable domains of monoclonal antibodies approved for cancer treatment" Critical Reviews in Oncology/Hematology, 2007, pp. 210-225, vol. 64.

* cited by examiner

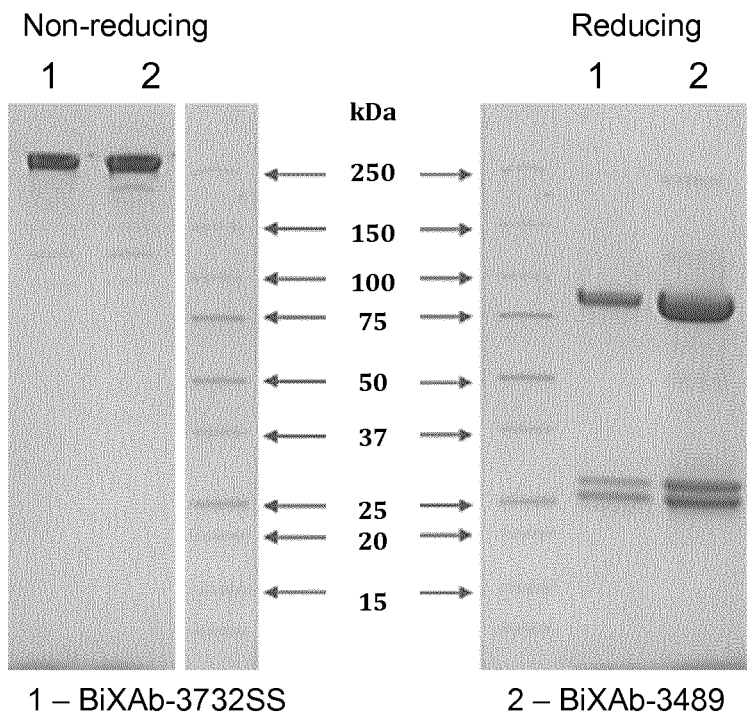
FIGURE 2A
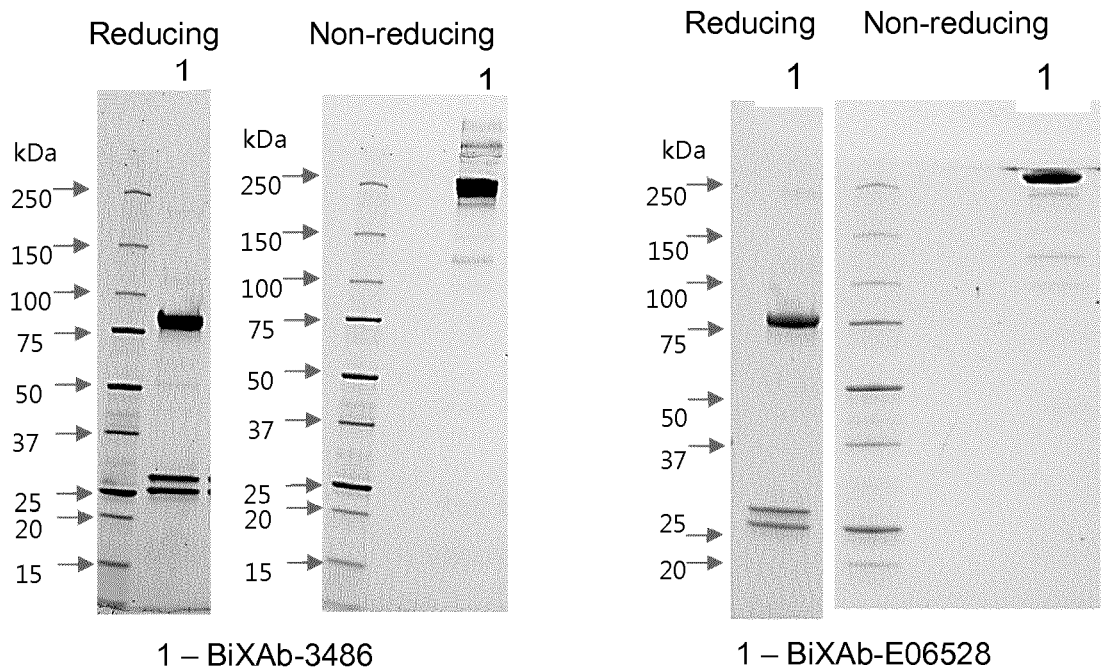
FIGURE 2B      FIGURE 2C

SEQUENCE LISTING

```
<160> NUMBER OF SEQ ID NOS: 38

<210> SEQ ID NO 1
<211> LENGTH: 120
<212> TYPE: PRT
<213> ORGANISM: Homo sapiens

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60
```

-continued

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
            115                 120

<210> SEQ ID NO 2
<211> LENGTH: 98
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val

<210> SEQ ID NO 3
<211> LENGTH: 34
<212> TYPE: PRT
<213> ORGANISM: Artificial Sequence
<220> FEATURE:
<223> OTHER INFORMATION: linker sequence

<400> SEQUENCE: 3

Glu Pro Lys Ser Cys Asp Lys Thr His Thr Cys Pro Pro Cys Pro Ala
  1               5                  10                  15

Pro Glu Leu Leu Gly Gly Pro Ser Thr Pro Pro Thr Pro Ser Pro Ser
                 20                  25                  30

Gly Gly

<210> SEQ ID NO 4
<211> LENGTH: 119
<212> TYPE: PRT
<213> ORGANISM: Homo sapiens

<400> SEQUENCE: 4

Gln Val Gln Leu Lys Gln Ser Gly Pro Gly Leu Val Gln Pro Ser Gln
  1               5                  10                  15

Ser Leu Ser Ile Thr Cys Thr Val Ser Gly Phe Ser Leu Thr Asn Tyr
                 20                  25                  30

Gly Val His Trp Val Arg Gln Ser Pro Gly Lys Gly Leu Glu Trp Leu
             35                  40                  45

Gly Val Ile Trp Ser Gly Gly Asn Thr Asp Tyr Asn Thr Pro Phe Thr
 50                  55                  60

Ser Arg Leu Ser Ile Asn Lys Asp Asn Ser Lys Ser Gln Val Phe Phe
```

```
            65                  70                  75                  80
Lys Met Asn Ser Leu Gln Ser Asn Asp Thr Ala Ile Tyr Tyr Cys Ala
                    85                  90                  95

Arg Ala Leu Thr Tyr Tyr Asp Tyr Glu Phe Ala Tyr Trp Gly Gln Gly
                    100                 105                 110

Thr Leu Val Thr Val Ser Ala
            115

<210> SEQ ID NO 5
<211> LENGTH: 98
<212> TYPE: PRT
<213> ORGANISM: Homo sapiens

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Glu Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 6
<211> LENGTH: 15
<212> TYPE: PRT
<213> ORGANISM: Homo sapiens

<400> SEQUENCE: 6

Glu Pro Lys Ser Cys Asp Lys Thr His Thr Cys Pro Pro Cys Pro
1               5                   10                  15

<210> SEQ ID NO 7
<211> LENGTH: 110
<212> TYPE: PRT
<213> ORGANISM: Homo sapiens

<400> SEQUENCE: 7

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 8
<211> LENGTH: 107
<212> TYPE: PRT
<213> ORGANISM: Homo sapiens

<400> SEQUENCE: 8

```
Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 9
<211> LENGTH: 701
<212> TYPE: PRT
<213> ORGANISM: Artificial Sequence
<220> FEATURE:
<223> OTHER INFORMATION: BiXAb 3486 heavy chain

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
```

```
            210                 215                 220
Lys Thr His Thr Cys Pro Pro Cys Pro Ala Pro Glu Leu Leu Gly Gly
225                 230                 235                 240

Pro Ser Thr Pro Pro Thr Pro Ser Pro Ser Gly Gly Gln Val Gln Leu
                    245                 250                 255

Lys Gln Ser Gly Pro Gly Leu Val Gln Pro Ser Gln Ser Leu Ser Ile
                260                 265                 270

Thr Cys Thr Val Ser Gly Phe Ser Leu Thr Asn Tyr Gly Val His Trp
            275                 280                 285

Val Arg Gln Ser Pro Gly Lys Gly Leu Glu Trp Leu Gly Val Ile Trp
        290                 295                 300

Ser Gly Gly Asn Thr Asp Tyr Asn Thr Pro Phe Thr Ser Arg Leu Ser
305                 310                 315                 320

Ile Asn Lys Asp Asn Ser Lys Ser Gln Val Phe Phe Lys Met Asn Ser
                    325                 330                 335

Leu Gln Ser Asn Asp Thr Ala Ile Tyr Tyr Cys Ala Arg Ala Leu Thr
                340                 345                 350

Tyr Tyr Asp Tyr Glu Phe Ala Tyr Trp Gly Gln Gly Thr Leu Val Thr
            355                 360                 365

Val Ser Ala Ala Ser Thr Lys Gly Pro Ser Val Phe Pro Leu Ala Pro
        370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
                    405                 410                 415

Leu Thr Ser Gly Val His Thr Phe Pro Ala Val Leu Gln Ser Ser Gly
                420                 425                 430

Leu Tyr Ser Leu Ser Ser Val Val Glu Val Pro Ser Ser Ser Leu Gly
            435                 440                 445

Thr Gln Thr Tyr Ile Cys Asn Val Asn His Lys Pro Ser Asn Thr Lys
        450                 455                 460

Val Asp Lys Lys Val Glu Pro Lys Ser Cys Asp Lys Thr His Thr Cys
465                 470                 475                 480

Pro Pro Cys Pro Ala Pro Glu Leu Leu Gly Gly Pro Ser Val Phe Leu
                    485                 490                 495

Phe Pro Pro Lys Pro Lys Asp Thr Leu Met Ile Ser Arg Thr Pro Glu
                500                 505                 510

Val Thr Cys Val Val Val Asp Val Ser His Glu Asp Pro Glu Val Lys
            515                 520                 525

Phe Asn Trp Tyr Val Asp Gly Val Glu Val His Asn Ala Lys Thr Lys
        530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                    565                 570                 575

Val Ser Asn Lys Ala Leu Pro Ala Pro Ile Glu Lys Thr Ile Ser Lys
                580                 585                 590

Ala Lys Gly Gln Pro Arg Glu Pro Gln Val Tyr Thr Leu Pro Pro Ser
            595                 600                 605

Arg Glu Glu Met Thr Lys Asn Gln Val Ser Leu Thr Cys Leu Val Lys
        610                 615                 620

Gly Phe Tyr Pro Ser Asp Ile Ala Val Glu Trp Glu Ser Asn Gly Gln
625                 630                 635                 640
```

```
Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
        660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Lys
    690                 695                 700

<210> SEQ ID NO 10
<211> LENGTH: 107
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 11
<211> LENGTH: 107
<212> TYPE: PRT
<213> ORGANISM: Homo sapiens

<400> SEQUENCE: 11

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 12
<211> LENGTH: 214
<212> TYPE: PRT
<213> ORGANISM: Homo sapiens

<400> SEQUENCE: 12
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
            210

<210> SEQ ID NO 13
<211> LENGTH: 107
<212> TYPE: PRT
<213> ORGANISM: Homo sapiens

<400> SEQUENCE: 13

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
                100                 105

<210> SEQ ID NO 14
<211> LENGTH: 107
<212> TYPE: PRT
<213> ORGANISM: Homo sapiens

<400> SEQUENCE: 14
```

```
Arg Thr Val Ala Ala Pro Ala Val Phe Ile Phe Pro Pro Ser Asp Glu
1               5                   10                  15

Gln Leu Lys Ser Gly Thr Ala Ser Val Val Cys Leu Leu Lys Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 15
<211> LENGTH: 214
<212> TYPE: PRT
<213> ORGANISM: Homo sapiens

<400> SEQUENCE: 15

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ala Val Phe Ile Phe Pro Pro Ser Asp Glu Gln Leu Lys Ser Gly
        115                 120                 125

Thr Ala Ser Val Val Cys Leu Leu Lys Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 16
<211> LENGTH: 34
<212> TYPE: PRT
<213> ORGANISM: Artificial Sequence
<220> FEATURE:
<223> OTHER INFORMATION: linker sequence -continued

<400> SEQUENCE: 16

Glu Pro Lys Ser Cys Asp Lys Thr His Thr Ser Pro Pro Ser Pro Ala
1               5                   10                  15

Pro Glu Leu Leu Gly Gly Pro Ser Thr Pro Pro Thr Pro Ser Pro Ser
            20                  25                  30

Gly Gly

<210> SEQ ID NO 17
<211> LENGTH: 701
<212> TYPE: PRT
<213> ORGANISM: Artificial Sequence
<220> FEATURE:
<223> OTHER INFORMATION: BiXAb 3489 heavy chain

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Ser Pro Pro Ser Pro Ala Pro Glu Leu Leu Gly Gly
225                 230                 235                 240

Pro Ser Thr Pro Pro Thr Pro Ser Pro Ser Gly Gly Gln Val Gln Leu
                245                 250                 255

Lys Gln Ser Gly Pro Gly Leu Val Gln Pro Ser Gln Ser Leu Ser Ile
            260                 265                 270

Thr Cys Thr Val Ser Gly Phe Ser Leu Thr Asn Tyr Gly Val His Trp
        275                 280                 285

Val Arg Gln Ser Pro Gly Lys Gly Leu Glu Trp Leu Gly Val Ile Trp
    290                 295                 300

Ser Gly Gly Asn Thr Asp Tyr Asn Thr Pro Phe Thr Ser Arg Leu Ser
305                 310                 315                 320

Ile Asn Lys Asp Asn Ser Lys Ser Gln Val Phe Phe Lys Met Asn Ser
            325                 330                 335

Leu Gln Ser Asn Asp Thr Ala Ile Tyr Tyr Cys Ala Arg Ala Leu Thr
        340                 345                 350

Tyr Tyr Asp Tyr Glu Phe Ala Tyr Trp Gly Gln Gly Thr Leu Val Thr
        355                 360                 365

Val Ser Ala Ala Ser Thr Lys Gly Pro Ser Val Phe Pro Leu Ala Pro
370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
                405                 410                 415

Leu Thr Ser Gly Val His Thr Phe Pro Ala Val Leu Gln Ser Ser Gly
            420                 425                 430

Leu Tyr Ser Leu Ser Ser Val Val Glu Val Pro Ser Ser Ser Leu Gly
        435                 440                 445

Thr Gln Thr Tyr Ile Cys Asn Val Asn His Lys Pro Ser Asn Thr Lys
    450                 455                 460

Val Asp Lys Lys Val Glu Pro Lys Ser Cys Asp Lys Thr His Thr Cys
465                 470                 475                 480

Pro Pro Cys Pro Ala Pro Glu Leu Leu Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Glu Glu Met Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Lys
    690                 695                 700

<210> SEQ ID NO 18
<211> LENGTH: 701
<212> TYPE: PRT
<213> ORGANISM: Artificial Sequence
<220> FEATURE:

<223> OTHER INFORMATION: BiXAb 3732 heavy chain

<400> SEQUENCE: 18

```
Gln Val Gln Leu Lys Gln Ser Gly Pro Gly Leu Val Gln Pro Ser Gln
  1               5                  10                  15

Ser Leu Ser Ile Thr Cys Thr Val Ser Gly Phe Ser Leu Thr Asn Tyr
             20                  25                  30

Gly Val His Trp Val Arg Gln Ser Pro Gly Lys Gly Leu Glu Trp Leu
         35                  40                  45

Gly Val Ile Trp Ser Gly Gly Asn Thr Asp Tyr Asn Thr Pro Phe Thr
     50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
             100                 105                 110

Thr Leu Val Thr Val Ser Ala Ala Ser Thr Lys Gly Pro Ser Val Phe
         115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Glu Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Thr Pro Pro Thr Pro Ser Pro Ser Gly Gly Glu Val Gln Leu Val
                245                 250                 255

Glu Ser Gly Gly Gly Leu Val Gln Pro Gly Gly Ser Leu Arg Leu Ser
            260                 265                 270

Cys Ala Ala Ser Gly Phe Asn Ile Lys Asp Thr Tyr Ile His Trp Val
        275                 280                 285

Arg Gln Ala Pro Gly Lys Gly Leu Glu Trp Val Ala Arg Ile Tyr Pro
    290                 295                 300

Thr Asn Gly Tyr Thr Arg Tyr Ala Asp Ser Val Lys Gly Arg Phe Thr
305                 310                 315                 320

Ile Ser Ala Asp Thr Ser Lys Asn Thr Ala Tyr Leu Gln Met Asn Ser
                325                 330                 335

Leu Arg Ala Glu Asp Thr Ala Val Tyr Tyr Cys Ser Arg Trp Gly Gly
            340                 345                 350

Asp Gly Phe Tyr Ala Met Asp Tyr Trp Gly Gln Gly Thr Leu Val Thr
        355                 360                 365

Val Ser Ser Ala Ser Thr Lys Gly Pro Ser Val Phe Pro Leu Ala Pro
    370                 375                 380

Ser Ser Lys Ser Thr Ser Gly Gly Thr Ala Ala Leu Gly Cys Leu Val
385                 390                 395                 400
```

```
Lys Asp Tyr Phe Pro Glu Pro Val Thr Val Ser Trp Asn Ser Gly Ala
                405                 410                 415

Leu Thr Ser Gly Val His Thr Phe Pro Ala Val Leu Gln Ser Ser Gly
            420                 425                 430

Leu Tyr Ser Leu Ser Ser Val Val Thr Val Pro Ser Ser Ser Leu Gly
        435                 440                 445

Thr Gln Thr Tyr Ile Cys Asn Val Asn His Lys Pro Ser Asn Thr Lys
    450                 455                 460

Val Asp Lys Lys Val Glu Pro Lys Ser Cys Asp Lys Thr His Thr Cys
465                 470                 475                 480

Pro Pro Cys Pro Ala Pro Glu Leu Leu Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Glu Glu Met Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Lys
    690                 695                 700

<210> SEQ ID NO 19
<211> LENGTH: 701
<212> TYPE: PRT
<213> ORGANISM: Artificial Sequence
<220> FEATURE:
<223> OTHER INFORMATION: BiXAb 3732SS heavy chain

<400> SEQUENCE: 19

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60
```

```
Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Glu Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Ser Pro Pro Ser Pro Ala Pro Glu Leu Leu Gly Gly Pro
225                 230                 235                 240

Ser Thr Pro Pro Thr Pro Ser Pro Ser Gly Gly Glu Val Gln Leu Val
                245                 250                 255

Glu Ser Gly Gly Gly Leu Val Gln Pro Gly Gly Ser Leu Arg Leu Ser
            260                 265                 270

Cys Ala Ala Ser Gly Phe Asn Ile Lys Asp Thr Tyr Ile His Trp Val
        275                 280                 285

Arg Gln Ala Pro Gly Lys Gly Leu Glu Trp Val Ala Arg Ile Tyr Pro
    290                 295                 300

Thr Asn Gly Tyr Thr Arg Tyr Ala Asp Ser Val Lys Gly Arg Phe Thr
305                 310                 315                 320

Ile Ser Ala Asp Thr Ser Lys Asn Thr Ala Tyr Leu Gln Met Asn Ser
                325                 330                 335

Leu Arg Ala Glu Asp Thr Ala Val Tyr Tyr Cys Ser Arg Trp Gly Gly
            340                 345                 350

Asp Gly Phe Tyr Ala Met Asp Tyr Trp Gly Gln Gly Thr Leu Val Thr
        355                 360                 365

Val Ser Ser Ala Ser Thr Lys Gly Pro Ser Val Phe Pro Leu Ala Pro
    370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
                405                 410                 415

Leu Thr Ser Gly Val His Thr Phe Pro Ala Val Leu Gln Ser Ser Gly
            420                 425                 430

Leu Tyr Ser Leu Ser Ser Val Val Thr Val Pro Ser Ser Ser Leu Gly
        435                 440                 445

Thr Gln Thr Tyr Ile Cys Asn Val Asn His Lys Pro Ser Asn Thr Lys
    450                 455                 460

Val Asp Lys Lys Val Glu Pro Lys Ser Cys Asp Lys Thr His Thr Cys
465                 470                 475                 480

Pro Pro Cys Pro Ala Pro Glu Leu Leu Gly Gly Pro Ser Val Phe Leu
```

485             490             495
Phe Pro Pro Lys Pro Lys Asp Thr Leu Met Ile Ser Arg Thr Pro Glu
                500             505             510
Val Thr Cys Val Val Val Asp Val Ser His Glu Asp Pro Glu Val Lys
                515             520             525
Phe Asn Trp Tyr Val Asp Gly Val Glu Val His Asn Ala Lys Thr Lys
                530             535             540
Pro Arg Glu Glu Gln Tyr Asn Ser Thr Tyr Arg Val Val Ser Val Leu
545             550             555             560
Thr Val Leu His Gln Asp Trp Leu Asn Gly Lys Glu Tyr Lys Cys Lys
                565             570             575
Val Ser Asn Lys Ala Leu Pro Ala Pro Ile Glu Lys Thr Ile Ser Lys
                580             585             590
Ala Lys Gly Gln Pro Arg Glu Pro Gln Val Tyr Thr Leu Pro Pro Ser
                595             600             605
Arg Glu Glu Met Thr Lys Asn Gln Val Ser Leu Thr Cys Leu Val Lys
                610             615             620
Gly Phe Tyr Pro Ser Asp Ile Ala Val Glu Trp Glu Ser Asn Gly Gln
625             630             635             640
Pro Glu Asn Asn Tyr Lys Thr Thr Pro Pro Val Leu Asp Ser Asp Gly
                645             650             655
Ser Phe Phe Leu Tyr Ser Lys Leu Thr Val Asp Lys Ser Arg Trp Gln
                660             665             670
Gln Gly Asn Val Phe Ser Cys Ser Val Met His Glu Ala Leu His Asn
                675             680             685
His Tyr Thr Gln Lys Ser Leu Ser Leu Ser Pro Gly Lys
                690             695             700

<210> SEQ ID NO 20
<211> LENGTH: 98
<212> TYPE: PRT
<213> ORGANISM: Homo sapiens

<400> SEQUENCE: 20

Ala Ser Thr Lys Gly Pro Ser Val Phe Pro Leu Ala Pro Ser Ser Lys
1               5               10              15
Ser Thr Ser Gly Gly Thr Ala Ala Leu Gly Cys Leu Val Lys Asp Tyr
                20              25              30
Phe Pro Glu Pro Val Thr Val Ser Trp Asn Ser Gly Ala Leu Thr Ser
                35              40              45
Gly Val His Thr Phe Pro Ala Val Leu Gln Ser Ser Gly Leu Tyr Ser
        50              55              60
Leu Ser Ser Val Val Thr Val Pro Ser Ser Ser Leu Gly Thr Gln Thr
65              70              75              80
Tyr Ile Cys Asn Val Asn His Lys Pro Ser Asn Thr Lys Val Asp Lys
                85              90              95
Lys Val

<210> SEQ ID NO 21
<211> LENGTH: 98
<212> TYPE: PRT
<213> ORGANISM: Homo sapiens

<400> SEQUENCE: 21

Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Lys Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 22
<211> LENGTH: 98
<212> TYPE: PRT
<213> ORGANISM: Homo sapiens

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Arg Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 23
<211> LENGTH: 107
<212> TYPE: PRT
<213> ORGANISM: Homo sapiens

<400> SEQUENCE: 23

Arg Thr Val Ala Ala Pro Ala Val Phe Ile Phe Pro Pro Ser Asp Glu
1               5                   10                  15

Gln Leu Lys Ser Gly Thr Ala Ser Val Val Cys Leu Leu Arg Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 24
<211> LENGTH: 107
<212> TYPE: PRT

<213> ORGANISM: Homo sapiens

<400> SEQUENCE: 24

Arg Thr Val Ala Ala Pro Ala Val Phe Ile Phe Pro Pro Ser Asp Glu
1               5                   10                  15

Gln Leu Lys Ser Gly Thr Ala Ser Val Val Cys Leu Leu Glu Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 25
<211> LENGTH: 107
<212> TYPE: PRT
<213> ORGANISM: Homo sapiens

<400> SEQUENCE: 25

Arg Thr Val Ala Ala Pro Ala Val Phe Ile Phe Pro Pro Ser Asp Glu
1               5                   10                  15

Gln Leu Lys Ser Gly Thr Ala Ser Val Val Cys Leu Leu Asp Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 26
<211> LENGTH: 119
<212> TYPE: PRT
<213> ORGANISM: Homo sapiens

<400> SEQUENCE: 26

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asp Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 27
<211> LENGTH: 119
<212> TYPE: PRT
<213> ORGANISM: Homo sapiens

<400> SEQUENCE: 27

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Glu Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 28
<211> LENGTH: 9
<212> TYPE: PRT
<213> ORGANISM: Homo sapiens

<400> SEQUENCE: 28

Ala Pro Glu Leu Leu Gly Gly Pro Ser
1               5

<210> SEQ ID NO 29
<211> LENGTH: 8
<212> TYPE: PRT
<213> ORGANISM: Homo sapiens

<400> SEQUENCE: 29

Thr Pro Pro Thr Pro Ser Pro Ser
1               5

<210> SEQ ID NO 30
<211> LENGTH: 107
<212> TYPE: PRT
<213> ORGANISM: Homo sapiens

<400> SEQUENCE: 30

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly

```
                        50                  55                  60
Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Asn Asn Asn Trp Pro Thr
                 85                  90                  95

Thr Phe Gly Gln Gly Thr Lys Leu Glu Ile Lys
                100                 105

<210> SEQ ID NO 31
<211> LENGTH: 107
<212> TYPE: PRT
<213> ORGANISM: Homo sapiens

<400> SEQUENCE: 31

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Ile Gly Thr Asn
             20                  25                  30

Ile His Trp Tyr Gln Gln Lys Pro Gly Gln Ala Pro Arg Leu Leu Ile
         35                  40                  45

Lys Tyr Ala Ser Glu Ser Ile Ser Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Asn Asn Asn Trp Pro Thr
                 85                  90                  95

Thr Phe Gly Gln Gly Thr Lys Leu Glu Ile Lys
                100                 105

<210> SEQ ID NO 32
<211> LENGTH: 119
<212> TYPE: PRT
<213> ORGANISM: Homo sapiens

<400> SEQUENCE: 32

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Asn Tyr
             20                  25                  30

Gly Val His Trp Val Arg Gln Pro Pro Gly Lys Gly Leu Glu Trp Leu
         35                  40                  45

Gly Val Ile Trp Ser Gly Gly Asn Thr Asp Tyr Asn Thr Pro Leu Thr
 50                  55                  60

Ser Arg Leu Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
        115

<210> SEQ ID NO 33
<211> LENGTH: 119
<212> TYPE: PRT
<213> ORGANISM: Homo sapiens

<400> SEQUENCE: 33
```

Gln Val Gln Leu Val Glu Ser Gly Gly Gly Val Val Gln Pro Gly Arg
1               5                   10                  15

Ser Leu Arg Leu Ser Cys Ala Val Ser Gly Phe Ser Leu Thr Asn Tyr
            20                  25                  30

Gly Val His Trp Val Arg Gln Ala Pro Gly Lys Gly Leu Glu Trp Leu
            35                  40                  45

Gly Val Ile Trp Ser Gly Gly Asn Thr Asp Tyr Asn Thr Pro Val Thr
        50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
            115

<210> SEQ ID NO 34
<211> LENGTH: 34
<212> TYPE: PRT
<213> ORGANISM: Artificial Sequence
<220> FEATURE:
<223> OTHER INFORMATION: linker sequence

<400> SEQUENCE: 34

Glu Pro Lys Ser Cys Asp Lys Thr His Thr Ser Pro Pro Ala Pro Ala
1               5                   10                  15

Pro Glu Leu Leu Gly Gly Pro Ala Ala Pro Pro Ala Pro Ala Pro Ala
            20                  25                  30

Gly Gly

<210> SEQ ID NO 35
<211> LENGTH: 701
<212> TYPE: PRT
<213> ORGANISM: Artificial Sequence
<220> FEATURE:
<223> OTHER INFORMATION: BiXAb E06528 heavy chain

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Ser Pro Pro Ala Pro Ala Pro Glu Leu Leu Gly Gly
225                 230                 235                 240

Pro Ala Ala Pro Pro Ala Pro Ala Pro Ala Gly Gly Gln Val Gln Leu
                245                 250                 255

Lys Gln Ser Gly Pro Gly Leu Val Gln Pro Ser Gln Ser Leu Ser Ile
            260                 265                 270

Thr Cys Thr Val Ser Gly Phe Ser Leu Thr Asn Tyr Gly Val His Trp
        275                 280                 285

Val Arg Gln Ser Pro Gly Lys Gly Leu Glu Trp Leu Gly Val Ile Trp
    290                 295                 300

Ser Gly Gly Asn Thr Asp Tyr Asn Thr Pro Phe Thr Ser Arg Leu Ser
305                 310                 315                 320

Ile Asn Lys Asp Asn Ser Lys Ser Gln Val Phe Phe Lys Met Asn Ser
                325                 330                 335

Leu Gln Ser Asn Asp Thr Ala Ile Tyr Tyr Cys Ala Arg Ala Leu Thr
            340                 345                 350

Tyr Tyr Asp Tyr Glu Phe Ala Tyr Trp Gly Gln Gly Thr Leu Val Thr
        355                 360                 365

Val Ser Ala Ala Ser Thr Lys Gly Pro Ser Val Phe Pro Leu Ala Pro
370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
                405                 410                 415

Leu Thr Ser Gly Val His Thr Phe Pro Ala Val Leu Gln Ser Ser Gly
            420                 425                 430

Leu Tyr Ser Leu Ser Ser Val Val Glu Val Pro Ser Ser Ser Leu Gly
        435                 440                 445

Thr Gln Thr Tyr Ile Cys Asn Val Asn His Lys Pro Ser Asn Thr Lys
        450                 455                 460

Val Asp Lys Lys Val Glu Pro Lys Ser Cys Asp Lys Thr His Thr Cys
465                 470                 475                 480

Pro Pro Cys Pro Ala Pro Glu Leu Leu Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560
```

```
Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Glu Glu Met Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Lys
    690                 695                 700

<210> SEQ ID NO 36
<211> LENGTH: 34
<212> TYPE: PRT
<213> ORGANISM: Artificial Sequence
<220> FEATURE:
<223> OTHER INFORMATION: linker sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 36

Glu Pro Lys Xaa Cys Asp Lys Xaa His Xaa Xaa Pro Pro Xaa Pro Ala
1               5                   10                  15

Pro Glu Leu Leu Gly Gly Pro Xaa Xaa Pro Pro Xaa Pro Xaa Pro Xaa
            20                  25                  30

Gly Gly

<210> SEQ ID NO 37
```

```
<211> LENGTH: 34
<212> TYPE: PRT
<213> ORGANISM: Artificial Sequence
<220> FEATURE:
<223> OTHER INFORMATION: linker sequence

<400> SEQUENCE: 37

Glu Pro Lys Ser Cys Asp Lys Thr His Thr Ser Pro Pro Ala Pro Ala
1               5                   10                  15

Pro Glu Leu Leu Gly Gly Pro Gly Gly Pro Pro Gly Pro Gly Pro Gly
            20                  25                  30

Gly Gly

<210> SEQ ID NO 38
<211> LENGTH: 34
<212> TYPE: PRT
<213> ORGANISM: Artificial Sequence
<220> FEATURE:
<223> OTHER INFORMATION: linker sequence

<400> SEQUENCE: 38

Glu Pro Lys Ser Cys Asp Lys Thr His Thr Ser Pro Pro Ala Pro Ala
1               5                   10                  15

Pro Glu Leu Leu Gly Gly Pro Ala Ala Pro Pro Gly Pro Ala Pro Gly
            20                  25                  30

Gly Gly
```

BISPECIFIC ANTIBODIES TARGETING EGFR AND HER2

CROSS-REFERENCE TO RELATED APPLICATION

This application is the U.S. national stage application of International Patent Application No. PCT/EP2017/060280, filed Apr. 28, 2017.

The Sequence Listing for this application is labeled "Seq-List.txt" which was created on Oct. 22, 2018 and is 59 KB. The entire content of the sequence listing is incorporated herein by reference in its entirety.

Subject matter disclosed within this application was developed and the claimed invention was made by, or on behalf of, one or more parties to a joint research agreement that was in effect on or before the effective filing date of the claimed invention and the claimed invention was made as a result of activities undertaken within the scope of the joint research agreement. The parties to the joint research agreement are Biomunex Pharmaceuticals, Institut National de la Sante et de la Recherche Medicale (INSERM), Universite de Montpellier, Universite de Tours, Centre National de la Recherche Scientifique (CNRS), and Institut Regional Du Cancer de Montpellier (ICM).

The present invention relates to bispecific antibodies targeting EGFR and HER2, methods for the production of this antibodies, compositions and uses thereof.

BACKGROUND OF THE INVENTION

The HER family, which includes 4 tyrosine kinase receptors (EGFR/HER1, HER2, HER3 and HER4), activates multiple, partially redundant, interconnected downstream signaling cascades, e.g. MAPK and PI3K/AKT pathways, which are involved in cell proliferation. HER abnormal signaling has been observed in a large number of solid tumors (lung, colorectal, pancreas, etc.). EGFR and HER2 are cell surface receptor tyrosine kinases (TKs) that transduce growth signals through homodimerization and heterodimerization with HER family receptors. The heterodimers of EGFR with HER2 induce more potent activation of TK signaling than does EGFR or HER2 homodimerization. When tumor cells overexpress both EGFR and HER2, they exhibit aggressive tumor cell growth, owing to the increased potential for EGFR/HER2 heterodimerization and signaling.

Pancreatic cancers are an example of solid tumors expressing EGFR and HER2 receptors with a very poor prognostic. In pancreatic tumors, EGFR is expressed in 45-95% of pancreatic cancer, and expression generally correlates with worse outcome in resected pancreatic cancers. Overexpression of HER2 has also been described in 7-58% of pancreatic cancer and HER2-amplified pancreatic cancers show an atypical metastatic pattern, suggesting that HER2 is likely to be also an important driver of tumorigenesis in pancreatic cancer. Moreover, it has been reported that approximately a quarter of pancreatic carcinomas that are EGFR+ are also additionally HER2+(Dancer et al (2007) Oncology Reports 18, p. 151), making them of double positive EGFR+/HER2 phenotype.

Pancreatic cancer is the fourth most common cause of cancer death in Europe with an increasing number of cases every year (+2% in men, +10% in women). It has a very poor prognosis, even when diagnosed early. It is one of the only cancers for which the survival rate has almost not been improved over the past 40 years: survival is inferior to 20% and 5% after 1 and 5 years respectively. Even though pancreatic cancer was responsible for more than 230,000 deaths in the world in 2012, it remains a rare disease, with as many deaths as newly diagnosed patients, due to lack of effective treatments. At present, pancreatic adenocarcinoma (90% of pancreatic cancers) is treated either surgically, by chemotherapy, or a combination of radiation and chemotherapy with limited results. The launch of gemcitabine in 1996 as first line treatment improved the survival without relapse by 1.3 month in median and the overall survival (OS) at one year from 2% to 18%. Since 2005, only two drugs, TARCEVA (erlotinib) and ABRAXANE (nab-paclitaxel), have been authorized for pancreatic cancer, despite various clinical trials, involving mainly combinations but few innovations. Erlotinib, that was the first targeted therapy, improved the survival without relapse by only 1 month in median in association with gemcitabine.

Treatment by means of therapeutic agents targeting HER receptors directly or downstream kinases often faces acquired resistance or is limited by the intrinsic robustness of the signal transduction network.

In such cases, combined therapies have emerged as natural countermeasures although their optimal design is not straightforward and can depend on the tumor or its subtypes, thus requiring prior patient stratification (Fitzgerald J B, Schoeberl B, Nielsen U B, Sorger P K. Systems biology and combination therapy in the quest for clinical efficacy. Nat Chem Biol. 2006; 2:458-66.). The current arsenal available to inhibit HER signaling is comprised of small molecule tyrosine kinase inhibitors (TKIs), e.g. lapatinib or erlotinib, and therapeutic antibodies, e.g. cetuximab or trastuzumab. Antibodies indeed represent a powerful approach that induces immunological effects on top of signaling reduction to help clearing the tumors as opposed to TKIs that are limited to signaling modulation.

Combined antibody-based therapies have been proposed by a number of authors. Targeting HER dimers, in particular EGFR/HER2 heterodimers, by mAb combinations was demonstrated to be advantageous for inhibition of pancreatic tumor growth.

Bispecific antibodies (BsAb) have further been designed, which combine the targets of two mAbs. Some bispecific anti-EGFR/anti-HER2 antibodies have more particularly been described. However they suffer from complicated designs that usually result in inferior manufacturability and stability, and efficacy of these antibodies could still be improved, since in in vivo pancreatic cancer models tumors continued to grow even while under treatment with bispecific antibodies.

For instance Liu and colleagues (Liu et al. A Novel Antibody Engineering Strategy for Making Monovalent Bispecific Heterodimeric IgG Antibodies by Electrostatic Steering Mechanism. J Biol. Chem. 2015; 290(12):7535-62) have described construction and characterization of a bispecific anti-EGFR and anti-HER2 antibody, in which panitumumab and trastuzumab sequences, respectively, were utilized. The antibody demonstrated improved activity against EGFR+/HER2+ cell lines in vitro and in vivo, however the activity of this antibody still needs to be improved. Lewis and colleagues (Lewis et al. Generation of bispecific IgG antibodies by structure-based design of an orthogonal Fab interface. Nature Biotechnology. 2014; 32; 191-198) also described a bispecific anti-EGFR and anti-HER2 antibody, however in this case different antibody sequences, matuzumab and pertuzumab sequences, respectively, and a different engineering design, were used.

International patent application WO2014/001324 reports a method for selecting and producing multispecific entities by using a transpeptidase, such as Sortase A, and the use of this method for the generation of novel tailor-made multispecific antibodies. A bispecific antibody containing pertuzumab and trastuzumab is exemplified. International patent application WO2014/124326 describes multispecific antibody constructs, containing for example trastuzumab and cetuximab, and multispecific antibody drug conjugates.

Bispecific HER2/EGFR antibodies are also described in European patent application EP2727940, wherein the antibodies carry six mutations in heavy chains to achieve heterodimeric pairing, as well as in European patent application EP2035456. However the structure of these antibodies may result in destabilization and immunogenicity.

Wang S et al. (Cancer Lett 2012 Dec. 28; 325(2):214-9) engineered an anti-EGFR/HER2 bispecific antibody using trastuzumab and cetuximab. However, binding to both antigens was monovalent and not bivalent like in natural antibodies, and thus full potential of EGFR and HER2 inhibition may not have been reached.

In view of the above, there is still a need for improved bispecific antibody constructs for treating tumors.

SUMMARY OF THE INVENTION

The inventors have now designed novel bispecific antibodies targeting EGFR and HER2, useful in the treatment of a variety of cancers.

The invention more particularly provides a bispecific antibody comprising two heavy chains and four light chains, wherein each heavy chain comprises
  a. a Fc region of an immunoglobulin comprising Hinge-CH2-CH3 domains,
  b. which Fc region is linked to Fab heavy chain CH1-VH of antibody 1 (Ab1) by said Hinge domain,
  c. which in turn is linked to Fab heavy chain CH1-VH of antibody 2 (Ab2), by a polypeptide linker sequence, wherein the polypeptide linker sequence links the N-terminus of said Fab heavy chain VH domain of Ab1 with the C-terminus of said CH1 domain of Ab2, and the four light chains comprise Fab light chains of Ab1 and Fab light chains of Ab2 associated with their cognate heavy chain domains;
  wherein Ab1 and Ab2, being different, independently are selected from the group consisting of cetuximab or a mutated derivative thereof, on the one hand, and trastuzumab, or a mutated derivative thereof, on the other hand.

In a first embodiment, Ab1 is cetuximab or a mutated derivative thereof, and Ab2 is trastuzumab, or a mutated derivative thereof.

In another embodiment, Ab1 is trastuzumab or a mutated derivative thereof, and Ab2 is cetuximab, or a mutated derivative thereof.

Bispecific antibodies are more particularly described, wherein Ab1 or Ab2 is cetuximab or a mutated derivative thereof, comprising
  a VH domain consisting of SEQ ID NO:4,
  a CH1 domain selected from the group consisting of SEQ ID NO: 2, SEQ ID NO: 5, SEQ ID NO: 20, SEQ ID NO: 21 and SEQ ID NO: 22,
  a VL domain consisting of SEQ ID NO: 13,
  a CL domain selected from the group consisting of SEQ ID NO: 11, SEQ ID NO: 14, SEQ ID NO: 23, SEQ ID NO: 24 and SEQ ID NO: 25,
  wherein the CH1 and CL domains associate as follows
  SEQ ID NO: 2 with SEQ ID NO: 11,
  SEQ ID NO: 5 with either SEQ ID NO: 14 or SEQ ID NO: 23,
  SEQ ID NO: 20 with either SEQ ID NO: 14 or SEQ ID NO: 23,
  SEQ ID NO: 21 with either SEQ ID NO: 24 or SEQ ID NO: 25,
  SEQ ID NO: 22 with either SEQ ID NO: 24 or SEQ ID NO: 25.

In another embodiment, bispecific antibodies are described, wherein Ab1 or Ab2 is trastuzumab or a mutated derivative thereof, comprising
  a VH domain consisting of sequence SEQ ID NO:1.
  a CH1 domain selected from the group consisting of SEQ ID NO: 2, SEQ ID NO: 5, SEQ ID NO: 20, SEQ ID NO: 21 and SEQ ID NO: 22,
  a VL domain consisting of sequence SEQ ID NO: 10,
  a CL domain selected from the group consisting of SEQ ID NO: 11, SEQ ID NO: 14, SEQ ID NO: 23, SEQ ID NO: 24 and SEQ ID NO:25, wherein the CH1 and CL domains associate as follows
  SEQ ID NO: 2 with SEQ ID NO: 11,
  SEQ ID NO: 5 with either SEQ ID NO: 14 or SEQ ID NO: 23,
  SEQ ID NO: 20 with either SEQ ID NO: 14 or SEQ ID NO: 23,
  SEQ ID NO: 21 with either SEQ ID NO: 24 or SEQ ID NO: 25,
  SEQ ID NO: 22 with either SEQ ID NO: 24 or SEQ ID NO: 25.

Preferably, the CH1 and CL domains of Ab1 have a combination of sequences different from the CH1 and CL domains of Ab2.

In an advantageous embodiment, the polypeptide linker sequence consists of SEQ ID NO: 3, SEQ ID NO: 16 or SEQ ID NO:34.

A particular antibody is provided which consists of
  a) two heavy chains, each consisting of a continuous sequence comprising, in N- to C-terminus order:
    trastuzumab heavy chain VH consisting of SEQ ID NO: 1,
    CH1 domain consisting of SEQ ID NO: 2,
    a polypeptide linker consisting of SEQ ID NO: 3, SEQ ID NO:16 or SEQ ID NO:34,
    cetuximab heavy chain VH consisting of SEQ ID NO: 4,
    CH1 domain consisting of SEQ ID NO: 5,
    Hinge domain consisting of SEQ ID NO: 6,
    CH2 domain consisting of SEQ ID NO: 7,
    CH3 domain of consisting of SEQ ID NO: 8,
  b) two trastuzumab light chains, each comprising
    a VL domain consisting of SEQ ID NO: 10,
    a CL domain consisting of SEQ ID NO: 11,
  c) two cetuximab light chains, each comprising:
    a VL domain consisting of SEQ ID NO: 13,
    a CL domain consisting of SEQ ID NO: 14.

Another particular antibody is provided which consists of
  a) two heavy chains, each consisting of a continuous sequence comprising, in N- to C-terminus order:
    cetuximab heavy chain VH consisting of SEQ ID NO: 4,
    CH1 domain consisting of SEQ ID NO: 5,
    a polypeptide linker consisting of SEQ ID NO: 3, SEQ ID NO:16 or SEQ ID NO:34,
    trastuzumab heavy chain VH consisting of SEQ ID NO: 1, CH1 domain consisting of SEQ ID NO: 2,
Hinge domain consisting of SEQ ID NO: 6,
CH2 domain consisting of SEQ ID NO: 7,
CH3 domain consisting of SEQ ID NO: 8,
b) two trastuzumab light chains, each comprising SEQ ID NO: 12,
c) two cetuximab light chains, each comprising SEQ ID NO: 15.

Preferred bispecific antibodies of the invention are antibodies with cetuximab VH sequences consisting of sequences SEQ ID NO: 4, SEQ ID NO:26 and SEQ ID NO:27.

The invention further encompasses bispecific antibodies containing humanized version of light chains and/or heavy chains of cetuximab.

In a particular embodiment, bispecific antibodies of the invention contain mutated VH and VL sequences of trastuzumab.

Also herein described is a polynucleotide comprising a sequence encoding a protein chain of the invention. Said polynucleotide may also comprise additional sequences: in particular it may advantageously comprise a sequence encoding a leader sequence or signal peptide allowing secretion of said protein chain.

The present invention also encompasses host-cells transformed with said polynucleotide.

It is further described a polypeptide which consists of a heavy chain of the bispecific antibody as defined above, as well as a polynucleotide comprising a sequence encoding said polypeptide.

A host cell transfected with an expression vector comprising said polynucleotide is also described.

Still another object of the invention is a method for preparing the bispecific antibodies of the invention.

A method for producing the bispecific antibody of the invention is thus provided, said method comprising the following steps: a) culturing in suitable medium and culture conditions a host cell expressing an antibody heavy chain as defined above, and antibody light chains as defined above; and b) recovering said produced antibodies from the culture medium or from said cultured cells.

LEGENDS TO THE FIGURES

FIG. 2A shows a SDS polyacrylamide gel electrophoresis of bispecific antibodies BiXAb-3732SS and BiXAb-3489 under reducing and non-reducing conditions.

FIG. 2B shows a SDS polyacrylamide gel electrophoresis of bispecific antibody BiXAb-3486 under reducing and non-reducing conditions.

FIG. 2C shows a SDS polyacrylamide gel electrophoresis of bispecific antibody BiXAb-E06528 under reducing and non-reducing conditions.

Figure 7A:
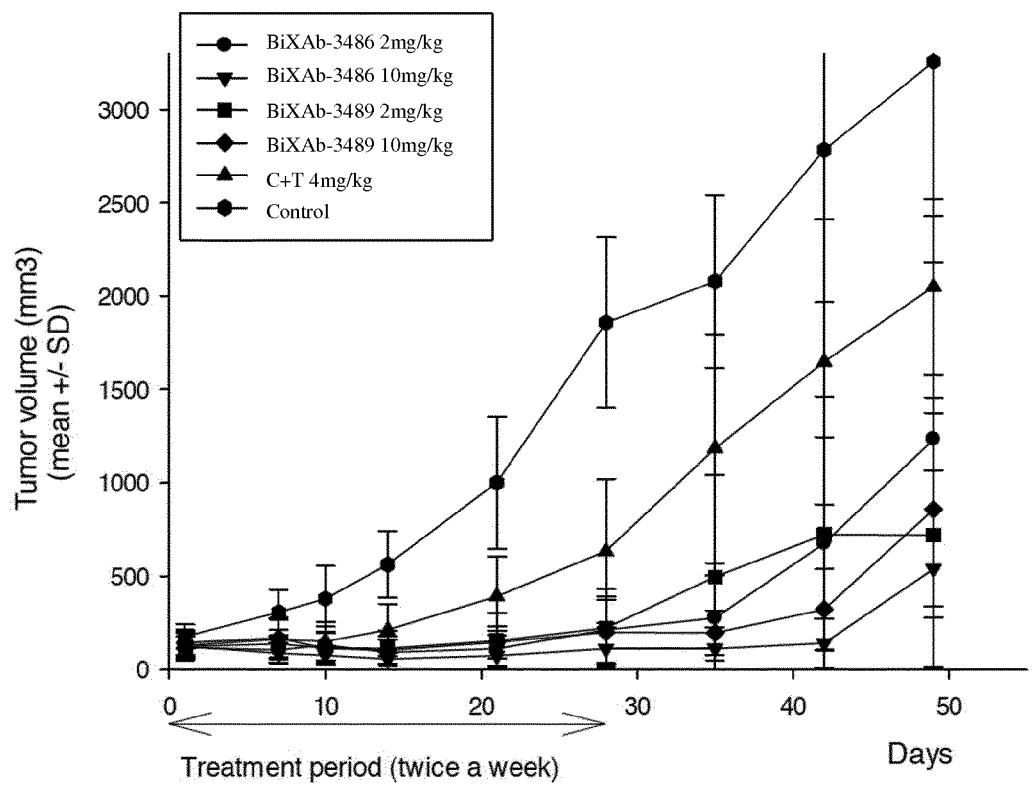
FIG. 7A shows the effect of BiXab-3486, BiXab-3489 at different doses (2 mg/kg and 10 mg/kg), and the combination of parental anti-EGFR and anti-HER2 with a total concentration of 4 mg/kg, and control in nude mice bearing BxPC-3 (linear scale).
Figure 7B:
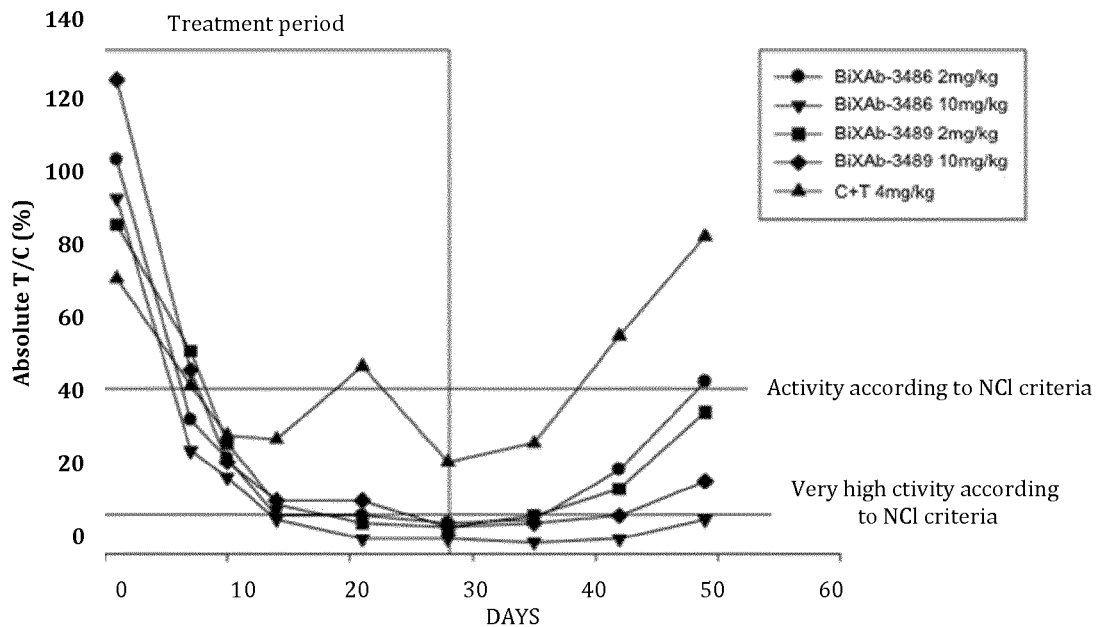

FIG. 7B shows the tumor growth inhibition (T/C %) of six different cohorts of mice that received different doses (2 mg/kg and 10 mg/kg) of BiXAb-3486 and BiXAb-3489, the combination of anti-HER2 and anti-EGFR antibodies with a total concentration of 4 mg/kg, or control. Tumor growth inhibition (T/C %) is defined as the ratio of the median tumor volume for the treated vs. control group and was calculated as T/C %=[(median tumor volume of treated group at day X)/(median tumor volume of control group at day X)]×100.

Figure 7C:
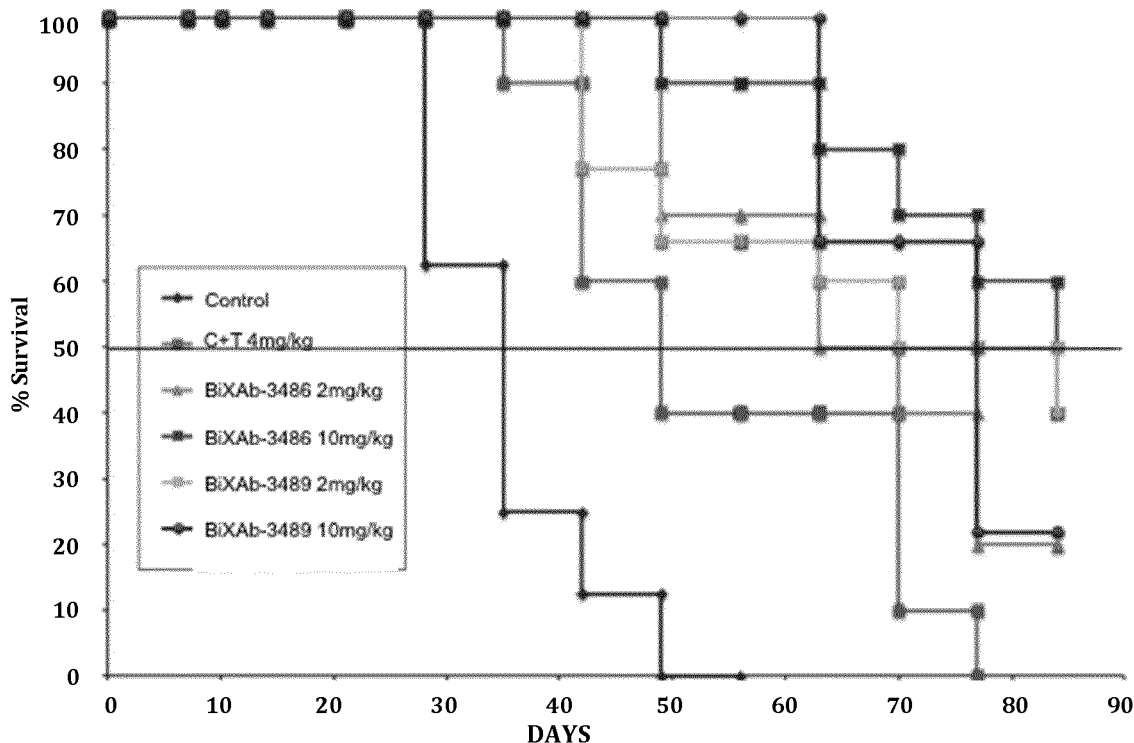

FIG. 7C Kaplan-Meier survival curves comparing mice treated with different doses (2 mg/kg and 10 mg/kg) of BiXAb-3486 and BiXAb-3489, the combination of anti-HER2 and anti-EGFR antibodies with a total concentration of 4 mg/kg, and control.

Figure 7D:
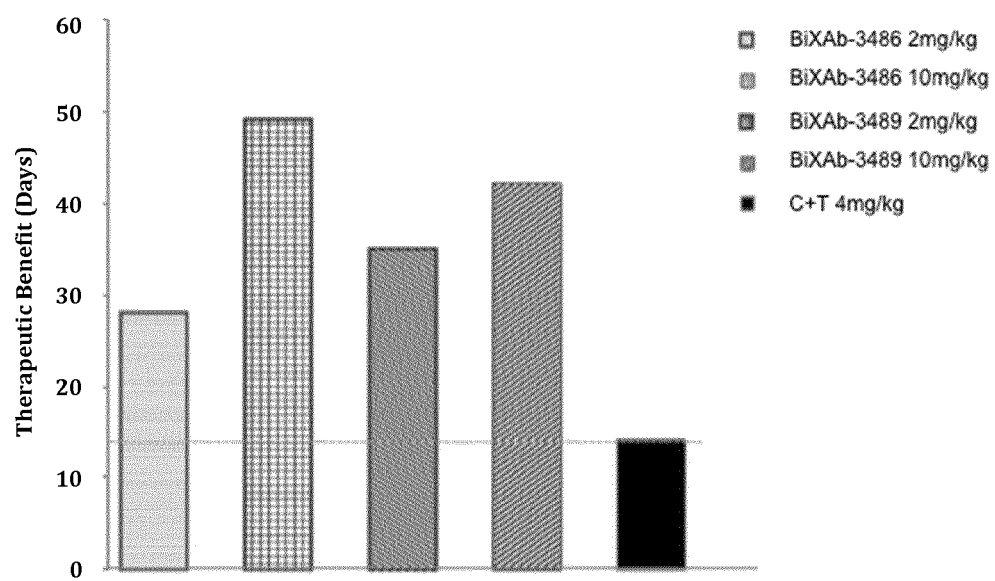

FIG. 7D shows therapeutic benefit observed in mice that received treatment with BiXAbs or the combination of parental anti-HER2- and anti-EGFR relative to mice that received no treatment (control). Therapeutic benefit is defined as median survival of treated groups—median survival of the control group.

DETAILED DESCRIPTION OF THE INVENTION

Definitions

The basic structure of a naturally occurring antibody molecule is a Y-shaped tetrameric quaternary structure consisting of two identical heavy chains and two identical light chains, held together by non-covalent interactions and by inter-chain disulfide bonds.

In mammalian species, there are five types of heavy chains: α, δ, ε, γ, and μ, which determine the class (isotype) of immunoglobulin: IgA, IgD, IgE, IgG, and IgM, respectively. The heavy chain N-terminal variable domain (VH) is followed by a constant region, containing three domains (numbered CH1, CH2, and CH3 from the N-terminus to the C-terminus) in heavy chains γ,α, and δ, while the constant region of heavy chains μ and ε is composed of four domains (numbered CH1, CH2, CH3 and CH4 from the N-terminus to the C-terminus). The CH1 and CH2 domains of IgA, IgG, and IgD are separated by a flexible hinge, which varies in length between the different classes and in the case of IgA and IgG, between the different subtypes: IgG1, IgG2, IgG3, and IgG4 have respectively hinges of 15, 12, 62 (or 77), and 12 amino acids, and IgA1 and IgA2 have respectively hinges of 20 and 7 amino acids.

There are two types of light chains: γ and κ, which can associate with any of the heavy chains isotypes, but are both of the same type in a given antibody molecule. Both light chains appear to be functionally identical. Their N-terminal variable domain (VL) is followed by a constant region consisting of a single domain termed CL.

The heavy and light chains pair by protein/protein interactions between the CH1 and CL domains, and via VH/VL interactions and the two heavy chains associate by protein/protein interactions between their CH3 domains. The structure of the immunoglobulin molecule is generally stabilized by interchains disulfide bonds between the CH1 and CL domains and between the hinges.

The antigen-binding regions correspond to the arms of the Y-shaped structure, which consist each of the complete light chain paired with the VH and CH1 domains of the heavy chain, and are called the Fab fragments (for Fragment antigen binding). Fab fragments were first generated from native immunoglobulin molecules by papain digestion which cleaves the antibody molecule in the hinge region, on the amino-terminal side of the interchains disulfide bonds, thus releasing two identical antigen-binding arms. Other proteases such as pepsin, also cleave the antibody molecule in the hinge region, but on the carboxy-terminal side of the interchains disulfide bonds, releasing fragments consisting of two identical Fab fragments and remaining linked through disulfide bonds; reduction of disulfide bonds in the F(ab')2 fragments generates Fab' fragments.

The part of the antigen binding region corresponding to the VH and VL domains is called the Fv fragment (for Fragment variable); it contains the CDRs (complementarity determining regions), which form the antigen-binding site (also termed paratope).

The effector region of the antibody which is responsible of its binding to effector molecules or cells, corresponds to the stem of the Y-shaped structure, and contains the paired CH2 and CH3 domains of the heavy chain (or the CH2, CH3 and CH4 domains, depending on the class of antibody), and is called the Fc (for Fragment crystallisable) region. Due to the identity of the two heavy chains and the two light chains, naturally occurring antibody molecules have two identical antigen-binding sites and thus bind simultaneously to two identical epitopes.

An antibody "specifically binds" to a target antigen if it binds with greater affinity, avidity, more readily, and/or with greater duration than it binds to other substances. "Specific binding" or "preferential binding" does not necessarily require (although it can include) exclusive binding. Generally, but not necessarily, reference to binding means preferential binding.

Cetuximab (ERBITUX; ImClone/Lilly, Merck-Serono) is a chimeric mouse-human monoclonal antibody (ATCC HB-9764 & ATCC-97-63) targeting epidermal growth factor receptor (EGFR). See also EP0359282, EP0667165, and U.S. Pat. No. 6,217,866. Cetuximab is approved for use as a treatment for colorectal cancer and squamous cell carcinoma of the head and neck.

Trastuzumab (HERCEPTIN; Genentech/Roche) is a humanized IgG1 that interferes with the HER2/neu receptor. See also EP0590058, U.S. Pat. Nos. 5,821,337, 8,075,890, 6,407,213, 6,054,297, 5,772,997, 6,165,464, 6,399,063 and 6,639,055. Its indications are the treatment of adjuvant and metastatic breast and metastatic gastric cancers.

In the context of the present invention, the term "polypeptide linker sequence" is a polypeptide of about 20 to 80 amino acids, preferably between 30 and 60 amino acids, still preferably between 30 and 40 amino acids. Advantageously, the linker sequence is "hinge-derived", which means that the polypeptide linker comprises all or part of the sequence of the hinge region of one or more immunoglobulin(s) selected among IgA, IgG, and IgD, preferably of human origin. Said polypeptide linker may comprise all or part of the sequence of the hinge region of only one immunoglobulin. In this case, said immunoglobulin may belong to the same isotype and subclass as the immunoglobulin from which the adjacent CH1 domain is derived, or to a different isotype or subclass.

Alternatively, said polypeptide linker may comprise all or part of the sequences of hinge regions of at least two immunoglobulins of different isotypes or subclasses. In this case, the N-terminal portion of the polypeptide linker, which directly follows the CH1 domain, preferably consists of all or part of the hinge region of an immunoglobulin belonging to the same isotype and subclass as the immunoglobulin from which said CH1 domain is derived. Optionally, said polypeptide linker may further comprise a sequence of from 2 to 15, preferably of from 5 to 10 N-terminal amino-acids of the CH2 domain of an immunoglobulin. In some cases, sequences from native hinge regions can be used; in other cases point mutations can be brought to these sequences, in particular the replacement of one or more cysteine residues in native IgG1, IgG2 or IgG3 hinge sequences by alanine or serine, in order to avoid unwanted intra-chain or inter-chains disulfide bonds.

A non-limitative example of a polypeptide linker which can be used in a bispecific antibody of the invention is a polypeptide having the following sequence:

```
                                              (SEQ ID NO: 3)
        EPKSCDKTHTCPPCPAPELLGGPSTPPTPSPSGG.
```

Said polypeptide consists of the full length sequence of human IgG1 hinge, followed by the 9 N-terminal amino-acids of human IgG1 CH2 (APELLGGPS (SEQ ID NO:28)), by a portion of the sequence of human IgA1 hinge (TPPTPSPS (SEQ ID NO:29)), and by the dipeptide GG, added to provide supplemental flexibility to the linker. In another preferred embodiment, the hinge-derived polypeptide linker sequence is SEQ ID NO:16 or SEQ ID NO:34.

The terms "subject," "Individual," and "patient" are used interchangeably herein and refer to a mammal being assessed for treatment and/or being treated. Subjects may be human, but also include other mammals, particularly those mammals useful as laboratory models for human disease, e.g. mouse, rat, rabbit, dog, etc.

The term "treatment" or "treating" refers to an action, application or therapy, wherein a subject, including a human being, is subjected to medical aid with the purpose of improving the subject's condition, directly or indirectly. Particularly, the term refers to reducing incidence, or alleviating symptoms, eliminating recurrence, preventing recurrence, preventing incidence, improving symptoms, improving prognosis or combination thereof in some embodiments. The skilled artisan would understand that treatment does not necessarily result in the complete absence or removal of symptoms. For example, with respect to cancer, "treatment" or "treating" may refer to slowing neoplastic or malignant cell growth, proliferation, or metastasis, preventing or delaying the development of neoplastic or malignant cell growth, proliferation, or metastasis, or some combination thereof.

Design of the Bispecific Antibodies

The inventors now provide bispecific tetravalent antibodies, comprising two binding sites to each of their targets, and a functional Fc domain allowing the activation of effector functions such as antibody-dependent cell-mediated cytotoxicity (ADCC), phagocytosis, and complement-dependent cytotoxicity (CDC).

The invention relates specifically to bispecific antibodies constructed using the amino acid sequences of the heavy chain (VH) and the light chain (VL) variable regions of two monoclonal antibodies targeting EGFR and HER2, namely cetuximab and trastuzumab, respectively.

The antibodies of the invention are full-length antibodies. They preferably comprise heavy chains and light chains from human immunoglobulins, preferably IgG, still preferably IgG1. The light chains preferably are Kappa light chains.

Figure 1:
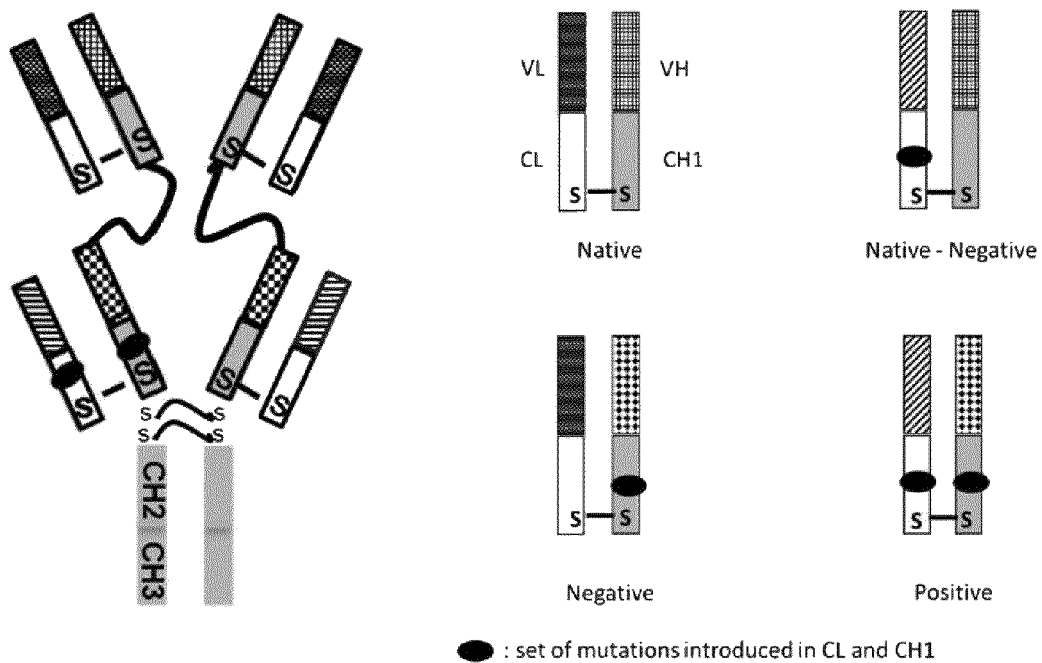
FIG. 1 is a schematic drawing of a bispecific antibody of the invention.

An example of the antibodies of the invention, which have an IgG-like structure, is illustrated in FIG. 1.

The bispecific antibodies of the invention typically comprise
   a continuous heavy chain constructed of an Fc (Hinge-CH2-CH3),
   followed by antibody 1 Fab heavy chain (CH1-VH) and the successive Fab heavy chain (CH1-VH) of antibody 2, the latter joined by a hinge-derived polypeptide linker sequence,
   and during protein expression the resulting heavy chain assembles into dimers while the co-expressed antibody 1 and antibody 2 light chains (VL-CL) associate with their cognate heavy chains in order to form the final tandem F(ab)'2-Fc molecule,
the antibody 1 (Ab1) and the antibody 2 (Ab2) being different and selected from the group consisting of cetuximab, trastuzumab and they mutated or humanized derivatives.

In one embodiment, of the invention, the bispecific antibodies comprise
   a continuous heavy chain constructed of an Fc (Hinge-CH2-CH3),
   followed by trastuzumab Fab heavy chain (CH1-VH) and the successive Fab heavy chain (CH1-VH) of cetuximab, the latter joined by a hinge-derived polypeptide linker sequence,
   and during protein expression the resulting heavy chain assembles into dimers while the co-expressed light chains (VL-CL) of wild type or mutated trastuzumab and wild type or mutated or humanized cetuximab associate with their cognate heavy chains in order to form the final tandem F(ab)'2-Fc molecule.

In another embodiment, of the invention, the bispecific antibodies comprise
   a continuous heavy chain constructed of an Fc (Hinge-CH2-CH3),
   followed by cetuximab Fab heavy chain (CH1-VH) and the successive Fab heavy chain (CH1-VH) of trastuzumab, the latter joined by a hinge-derived polypeptide linker sequence,
   and during protein expression the resulting heavy chain assembles into dimers while the co-expressed light chains (VL-CL) of wild type or mutated cetuximab and wild type or mutated trastuzumab associate with their cognate heavy chains in order to form the final tandem F(ab)'2-Fc molecule.

In a preferred embodiment, it is described bispecific antibodies which comprise
   two Fab fragments with different CH1 and CL domains consisting of
   a) Fab fragment having CH1 and C-Kappa domains derived from a human IgG1/Kappa, and the VH and VL domains of Ab1,
   b) Fab fragment having CH1 and C-Kappa domains derived from a human IgG1/Kappa and the VH and VL domains of Ab2,
   c) a mutated light chain constant domain which is derived from human Kappa constant domain,
   the Fab fragments being tandemly arranged in the following order
      the C-terminal end of the CH1 domain of Ab1 Fab fragment being linked to the N-terminal end of the VH domain of Ab2 Fab fragment through a polypeptide linker,
      the hinge region of a human IgG1 linking the C-terminal ends of CH1 domain of Ab2 fragment to the N-terminal of the CH2 domain,
      the dimerized CH2 and CH3 domains of a human IgG1.

In still a preferred embodiment,

Ab1 is trastuzumab having
   a VH region corresponding to the sequences SEQ ID NO:1,
   a CH1 region corresponding to one of the sequences selected from the group consisting of SEQ ID NO: 2, SEQ ID NO: 5, SEQ ID NO: 20, SEQ ID NO: 21 and SEQ ID NO: 22.
   a VL region corresponding to the sequences SEQ ID NO: 10,
   a C-Kappa region corresponding to one of the sequences selected from the group consisting of SEQ ID NO: 11, SEQ ID NO: 14, SEQ ID NO: 23, SEQ ID NO: 24 and SEQ ID NO:25,
CH1 and C-Kappa regions that can only associate in the following combinations:
SEQ ID NO: 2 with SEQ ID NO: 11,
SEQ ID NO: 5 with either SEQ ID NO: 14 or SEQ ID NO: 23,
SEQ ID NO: 20 with either SEQ ID NO: 14 or SEQ ID NO: 23,
SEQ ID NO: 21 with either SEQ ID NO: 24 or SEQ ID NO: 25,
SEQ ID NO: 22 with either SEQ ID NO: 24 or SEQ ID NO: 25, Ab2 is cetuximab having
   a VH region corresponding to the sequences SEQ ID NO:4,
   a CH1 region corresponding to one of the sequences selected from the group consisting of SEQ ID NO: 2, SEQ ID NO: 5, SEQ ID NO: 20, SEQ ID NO: 21 and SEQ ID NO: 22,
   a VL region corresponding to the sequences SEQ ID NO: 13,
   a C-Kappa region corresponding to one of the sequences selected from the group consisting of SEQ ID NO: 11, SEQ ID NO: 14, SEQ ID NO: 23, SEQ ID NO: 24 and SEQ ID NO: 25, CH1 and C-Kappa regions that can only associate in the following combinations:
SEQ ID NO: 2 with SEQ ID NO: 11,
SEQ ID NO: 5 with either SEQ ID NO: 14 or SEQ ID NO: 23,
SEQ ID NO: 20 with either SEQ ID NO: 14 or SEQ ID NO: 23,
SEQ ID NO: 21 with either SEQ ID NO: 24 or SEQ ID NO: 25,
SEQ ID NO: 22 with either SEQ ID NO: 24 or SEQ ID NO: 25,
Ab1 and Ab2 have each a different CH1 and C-Kappa combination of sequences.

In another aspect,
Ab1 is cetuximab having
a VH region corresponding to the sequences SEQ ID NO: 4,
a CH1 region corresponding to one of the sequences selected from the group consisting of SEQ ID NO: 2, SEQ ID NO: 5, SEQ ID NO: 20, SEQ ID NO: 21 and SEQ ID NO: 22,
a VL region corresponding to the sequences SEQ ID NO: 13,
a C-Kappa region corresponding to one of the sequences selected from the group consisting of SEQ ID NO: 11, SEQ ID NO: 14, SEQ ID NO: 23, SEQ ID NO: 24 and SEQ ID NO: 25,
CH1 and C-Kappa regions that can only associate in the following combinations:
SEQ ID NO: 2 with SEQ ID NO: 11,
SEQ ID NO: 5 with either SEQ ID NO: 14 or SEQ ID NO: 23,
SEQ ID NO: 20 with either SEQ ID NO: 14 or SEQ ID NO: 23,
SEQ ID NO: 21 with either SEQ ID NO: 24 or SEQ ID NO: 25,
SEQ ID NO: 22 with either SEQ ID NO: 24 or SEQ ID NO: 25,
And Ab2 is trastuzumab having
a VH region corresponding to the sequences SEQ ID NO: 1,
a CH1 region corresponding to one of the sequences selected from the group consisting of
SEQ ID NO: 2, SEQ ID NO: 5, SEQ ID NO: 20, SEQ ID NO: 21 and SEQ ID NO: 22,
a VL region corresponding to the sequences SEQ ID NO: 10,
a C-Kappa region corresponding to one of the sequences selected from the group consisting of SEQ ID NO: 11, SEQ ID NO: 14, SEQ ID NO: 23, SEQ ID NO: 24 and SEQ ID NO: 25,
CH1 and C-Kappa regions that can only associate in the following combinations:
SEQ ID NO: 2 with SEQ ID NO: 11,
SEQ ID NO: 5 with either SEQ ID NO: 14 or SEQ ID NO: 23,
SEQ ID NO: 20 with either SEQ ID NO: 14 or SEQ ID NO: 23,
SEQ ID NO: 21 with either SEQ ID NO: 24 or SEQ ID NO: 25,
SEQ ID NO: 22 with either SEQ ID NO: 24 or SEQ ID NO: 25,
Ab1 and Ab2 have each a different CH1 and C-Kappa combination of sequences.

Throughout the present description, amino acid sequences are defined according to Kabat et al, Sequences of Proteins of Immunological Interest, 5th Ed. Public Health Service, National Institutes of Health, Bethesda, Md. (1991).

In a particular embodiment, the bispecific antibodies have the following structure:
a) a continuous heavy chain consisting of:
trastuzumab heavy chain variable region (VH) corresponding to SEQ ID NO: 1,
wild-type CH1 constant domain (residue at Kabat position 192 is threonine, T) from human IgG1 corresponding to SEQ ID NO: 2,
polypeptide linker joining the 2 Fab heavy chains corresponding to SEQ ID NO: 3,
cetuximab heavy chain variable region (VH) corresponding to SEQ ID NO: 4,
mutated CH1 constant domain (residue at Kabat position 192 has been mutated from threonine to glutamic acid, E) from human IgG1 corresponding to SEQ ID NO: 5,
wild-type Hinge region from human IgG1 corresponding to SEQ ID NO: 6,
wild-type CH2 domain of human IgG1 corresponding to SEQ ID NO: 7,
wild-type CH3 domain of human IgG1 allotype G1m (3) corresponding to SEQ ID NO: 8,
b) a trastuzumab light chain consisting of:
a wild-type variable region (VL) corresponding to SEQ ID NO: 10,
a wild-type human Kappa constant domain (residue at Kabat positions 114 and 137 are serine (S) and asparagine (N), respectively) corresponding to SEQ ID NO: 11,
c) a cetuximab light chain consisting of:
a wild-type variable region (VL) corresponding to SEQ ID NO: 13,
a mutated human Kappa constant domain (residue at Kabat positions 114 and 137 are alanine (A) and lysine (K), respectively) corresponding to SEQ ID NO: 14.

In another embodiment, the bispecific antibodies have the following structure:
a) continuous heavy chain consisting of
trastuzumab heavy chain variable region (VH) corresponding to SEQ ID NO: 1,
wild-type CH1 constant domain (residue at Kabat position 192 is threonine, T) from human IgG1 corresponding to SEQ ID NO: 2,
polypeptide linker joining the 2 Fab heavy chains corresponding to SEQ ID NO: 16 or SEQ ID NO:34,
cetuximab heavy chain variable region (VH) corresponding to SEQ ID NO: 4,
mutated CH1 constant domain (residue at Kabat position 192 has been mutated from threonine to glutamic acid, E,) from human IgG1 corresponding to SEQ ID NO: 5,
wild-type Hinge region from human IgG1 corresponding to SEQ ID NO: 6,
wild-type CH2 domain of human IgG1 corresponding to SEQ ID NO: 7,
wild-type CH3 domain of human IgG1 allotype G1m (3) corresponding to SEQ ID NO: 8,
b) an amino acid sequence of wild-type trastuzumab light chain corresponding to SEQ ID NO: 12,
c) amino acid sequence of mutated cetuximab light chain corresponding to SEQ ID NO: 15.

In a further aspect, the bispecific antibodies may have the following structure:
a) a continuous heavy chain consisting of
   cetuximab heavy chain variable region (VH) corresponding to SEQ ID NO: 4,
   mutated CH1 constant domain (residue at Kabat position 192 has been mutated from threonine to glutamic acid, E) from human IgG1 corresponding to SEQ ID NO: 5,
   polypeptide linker joining the 2 Fab heavy chains corresponding to SEQ ID NO: 3,
   trastuzumab heavy chain variable region (VH) corresponding to SEQ ID NO: 1,
   wild-type CH1 constant domain (residue at Kabat position 192 is threonine, T) from human IgG1 corresponding to SEQ ID NO: 2,
   wild-type Hinge region from human IgG1 corresponding to SEQ ID NO: 6,
   wild-type CH2 domain of human IgG1 corresponding to SEQ ID NO: 7,
   wild-type CH3 domain of human IgG1 allotype G1m (3) corresponding to SEQ ID NO: 8,
b) an amino acid sequence of wild-type trastuzumab light chain corresponding to SEQ ID-NO: 12 NO: 12,
c) an amino acid sequence of mutated cetuximab light chain corresponding to SEQ ID NO: 15.

In still a further aspect, the bispecific antibodies may have the following structure:
a) a continuous heavy chain consisting of
   cetuximab heavy chain variable region (VH) corresponding to SEQ ID NO: 4,
   mutated CH1 constant domain (residue at Kabat position 192 has been mutated from threonine to glutamic acid, E) from human IgG1 corresponding to SEQ ID NO: 5,
   polypeptide linker joining the 2 Fab heavy chains corresponding to SEQ ID NO: 16,
   trastuzumab heavy chain variable region (VH) corresponding to SEQ ID NO: 1,
   wild-type CH1 constant domain (residue at Kabat position 192 is threonine, T) from human IgG1 corresponding to SEQ ID NO: 2,
   wild-type Hinge region from human IgG1 corresponding to SEQ ID NO: 6,
   wild-type CH2 domain of human IgG1 corresponding to SEQ ID NO: 7,
   wild-type CH3 domain of human IgG1 allotype G1m (3) corresponding to SEQ ID NO: 8,
b) a amino acid sequence of wild-type trastuzumab light chain corresponding to SEQ ID NO: 12,
c) a amino acid sequence of mutated cetuximab light chain corresponding to SEQ ID NO: 15.

The bispecific antibodies may contain at least one of the following mutations:
a mutated CH1 constant domain from human IgG1 corresponding to SEQ ID NO: 20,
a mutated CH1 constant domain from human IgG1 corresponding to SEQ ID NO: 21,
a mutated CH1 constant domain from human IgG1 corresponding to SEQ ID NO: 22,
a mutated human Kappa constant corresponding to SEQ ID NO: 23,
a mutated human Kappa constant corresponding to SEQ ID NO: 24,
a mutated human Kappa constant domain corresponding to SEQ ID NO: 25.

In further aspects, the bispecific antibodies have a VH region, a CH1 domain, a VL region and a C-Kappa domain according to the combinations listed in Table 1 and Table 2, which show various possible formats for the antibodies of the invention.

The bispecific antibodies preferably show a higher binding affinity to EGFR and/or to HER2. For instance, the bispecific antibodies can show a Kd less than $1\times10^{-7}$ M, $10^{-8}$ M, preferably less than $1\times10^{-9}$ or $1\times10^{-10}$ M, with respect to EGFR and/or HER2.

TABLE 1

| Fab 1 trastuzumab | | | | Fab 2 cetuximab | | | |
| --- | --- | --- | --- | --- | --- | --- | --- |
| VH | CH1 | VL | C-Kappa | VH | CH1 | VL | C-Kappa |
| SEQ No 1 | SEQ No 5 | SEQ No 10 | SEQ No 14 | SEQ No 4 | SEQ No 21 | SEQ No 13 | SEQ No 24 |
| SEQ No 1 | SEQ No 5 | SEQ No 10 | SEQ No 14 | SEQ No 4 | SEQ No 21 | SEQ No 13 | SEQ No 25 |
| SEQ No 1 | SEQ No 5 | SEQ No 10 | SEQ No 14 | SEQ No 4 | SEQ No 22 | SEQ No 13 | SEQ No 24 |
| SEQ No 1 | SEQ No 5 | SEQ No 10 | SEQ No 14 | SEQ No 4 | SEQ No 22 | SEQ No 13 | SEQ No 25 |
| SEQ No 1 | SEQ No 5 | SEQ No 10 | SEQ No 23 | SEQ No 4 | SEQ No 21 | SEQ No 13 | SEQ No 24 |
| SEQ No 1 | SEQ No 5 | SEQ No 10 | SEQ No 23 | SEQ No 4 | SEQ No 21 | SEQ No 13 | SEQ No 25 |
| SEQ No 1 | SEQ No 5 | SEQ No 10 | SEQ No 23 | SEQ No 4 | SEQ No 22 | SEQ No 13 | SEQ No 24 |
| SEQ No 1 | SEQ No 5 | SEQ No 10 | SEQ No 23 | SEQ No 4 | SEQ No 22 | SEQ No 13 | SEQ No 25 |
| SEQ No 1 | SEQ No 20 | SEQ No 10 | SEQ No 14 | SEQ No 4 | SEQ No 21 | SEQ No 13 | SEQ No 24 |
| SEQ No 1 | SEQ No 20 | SEQ No 10 | SEQ No 14 | SEQ No 4 | SEQ No 21 | SEQ No 13 | SEQ No 25 |
| SEQ No 1 | SEQ No 20 | SEQ No 10 | SEQ No 14 | SEQ No 4 | SEQ No 22 | SEQ No 13 | SEQ No 24 |
| SEQ No 1 | SEQ No 20 | SEQ No 10 | SEQ No 14 | SEQ No 4 | SEQ No 22 | SEQ No 13 | SEQ No 25 |
| SEQ No 1 | SEQ No 20 | SEQ No 10 | SEQ No 23 | SEQ No 4 | SEQ No 21 | SEQ No 13 | SEQ No 24 |
| SEQ No 1 | SEQ No 20 | SEQ No 10 | SEQ No 23 | SEQ No 4 | SEQ No 21 | SEQ No 13 | SEQ No 25 |
| SEQ No 1 | SEQ No 20 | SEQ No 10 | SEQ No 23 | SEQ No 4 | SEQ No 22 | SEQ No 13 | SEQ No 24 |
| SEQ No 1 | SEQ No 20 | SEQ No 10 | SEQ No 23 | SEQ No 4 | SEQ No 22 | SEQ No 13 | SEQ No 25 |
| SEQ No 1 | SEQ No 2 | SEQ No 12 | | SEQ No 4 | SEQ No 21 | SEQ NO 13 | SEQ No 24 |
| SEQ No 1 | SEQ No 2 | SEQ No 12 | | SEQ No 4 | SEQ No 21 | SEQ NO 13 | SEQ No 25 |
| SEQ No 1 | SEQ No 2 | SEQ No 12 | | SEQ No 4 | SEQ No 22 | SEQ NO 13 | SEQ No 24 |
| SEQ No 1 | SEQ No 2 | SEQ No 12 | | SEQ No 4 | SEQ No 22 | SEQ NO 13 | SEQ No 25 |
| SEQ No 1 | SEQ No 2 | SEQ No 12 | | SEQ No 4 | SEQ No 5 | SEQ No 15 | |
| SEQ No 1 | SEQ No 2 | SEQ No 12 | | SEQ No 4 | SEQ No 5 | SEQ NO 13 | SEQ No 23 |
| SEQ No 1 | SEQ No 2 | SEQ No 12 | | SEQ No 4 | SEQ No 20 | SEQ No 15 | |
| SEQ No 1 | SEQ No 2 | SEQ No 12 | | SEQ No 4 | SEQ No 20 | SEQ NO 13 | SEQ No 23 |
| SEQ No 1 | SEQ No 21 | SEQ No 10 | SEQ No 24 | SEQ No 4 | SEQ No 2 | SEQ NO 13 | SEQ No 11 |

TABLE 1-continued

| Fab 1 trastuzumab | | | | Fab 2 cetuximab | | | |
|---|---|---|---|---|---|---|---|
| VH | CH1 | VL | C-Kappa | VH | CH1 | VL | C-Kappa |
| SEQ No 1 | SEQ No 21 | SEQ No 10 | SEQ No 25 | SEQ No 4 | SEQ No 2 | SEQ NO 13 | SEQ No 11 |
| SEQ No 1 | SEQ No 22 | SEQ No 10 | SEQ No 24 | SEQ No 4 | SEQ No 2 | SEQ NO 13 | SEQ No 11 |
| SEQ No 1 | SEQ No 22 | SEQ No 10 | SEQ No 25 | SEQ No 4 | SEQ No 2 | SEQ NO 13 | SEQ No 11 |
| SEQ No 1 | SEQ No 5 | SEQ No 10 | SEQ No 14 | SEQ No 4 | SEQ No 2 | SEQ NO 13 | SEQ No 11 |
| SEQ No 1 | SEQ No 5 | SEQ No 10 | SEQ No 23 | SEQ No 4 | SEQ No 2 | SEQ NO 13 | SEQ No 11 |
| SEQ No 1 | SEQ No 20 | SEQ No 10 | SEQ No 14 | SEQ No 4 | SEQ No 2 | SEQ NO 13 | SEQ No 11 |
| SEQ No 1 | SEQ No 20 | SEQ No 10 | SEQ No 23 | SEQ No 4 | SEQ No 2 | SEQ NO 13 | SEQ No 11 |

TABLE 2

| Fab 1 cetuximab | | | | Fab 2 trastuzumab | | | |
|---|---|---|---|---|---|---|---|
| VH | CH1 | VL | C-Kappa | VH | CH1 | VL | C-Kappa |
| SEQ No 4 | SEQ No 21 | SEQ No 13 | SEQ No 24 | SEQ No 1 | SEQ No 5 | SEQ No 10 | SEQ No 14 |
| SEQ No 4 | SEQ No 21 | SEQ No 13 | SEQ No 25 | SEQ No 1 | SEQ No 5 | SEQ No 10 | SEQ No 14 |
| SEQ No 4 | SEQ No 22 | SEQ No 13 | SEQ No 24 | SEQ No 1 | SEQ No 5 | SEQ No 10 | SEQ No 14 |
| SEQ No 4 | SEQ No 22 | SEQ No 13 | SEQ No 25 | SEQ No 1 | SEQ No 5 | SEQ No 10 | SEQ No 14 |
| SEQ No 4 | SEQ No 21 | SEQ No 13 | SEQ No 24 | SEQ No 1 | SEQ No 5 | SEQ No 10 | SEQ No 23 |
| SEQ No 4 | SEQ No 21 | SEQ No 13 | SEQ No 25 | SEQ No 1 | SEQ No 5 | SEQ No 10 | SEQ No 23 |
| SEQ No 4 | SEQ No 22 | SEQ No 13 | SEQ No 24 | SEQ No 1 | SEQ No 5 | SEQ No 10 | SEQ No 23 |
| SEQ No 4 | SEQ No 22 | SEQ No 13 | SEQ No 25 | SEQ No 1 | SEQ No 5 | SEQ No 10 | SEQ No 23 |
| SEQ No 4 | SEQ No 21 | SEQ No 13 | SEQ No 24 | SEQ No 1 | SEQ No 20 | SEQ No 10 | SEQ No 14 |
| SEQ No 4 | SEQ No 21 | SEQ No 13 | SEQ No 25 | SEQ No 1 | SEQ No 20 | SEQ No 10 | SEQ No 14 |
| SEQ No 4 | SEQ No 22 | SEQ No 13 | SEQ No 24 | SEQ No 1 | SEQ No 20 | SEQ No 10 | SEQ No 14 |
| SEQ No 4 | SEQ No 22 | SEQ No 13 | SEQ No 25 | SEQ No 1 | SEQ No 20 | SEQ No 10 | SEQ No 14 |
| SEQ No 4 | SEQ No 21 | SEQ No 13 | SEQ No 24 | SEQ No 1 | SEQ No 20 | SEQ No 10 | SEQ No 23 |
| SEQ No 4 | SEQ No 21 | SEQ No 13 | SEQ No 25 | SEQ No 1 | SEQ No 20 | SEQ No 10 | SEQ No 23 |
| SEQ No 4 | SEQ No 22 | SEQ No 13 | SEQ No 24 | SEQ No 1 | SEQ No 20 | SEQ No 10 | SEQ No 23 |
| SEQ No 4 | SEQ No 22 | SEQ No 13 | SEQ No 25 | SEQ No 1 | SEQ No 20 | SEQ No 10 | SEQ No 23 |
| SEQ No 4 | SEQ No 21 | SEQ NO 13 | SEQ No 24 | SEQ No 1 | SEQ No 2 | | SEQ No 12 |
| SEQ No 4 | SEQ No 21 | SEQ NO 13 | SEQ No 25 | SEQ No 1 | SEQ No 2 | | SEQ No 12 |
| SEQ No 4 | SEQ No 22 | SEQ NO 13 | SEQ No 24 | SEQ No 1 | SEQ No 2 | | SEQ No 12 |
| SEQ No 4 | SEQ No 22 | SEQ NO 13 | SEQ No 25 | SEQ No 1 | SEQ No 2 | | SEQ No 12 |
| SEQ No 4 | SEQ No 5 | | SEQ No 15 | SEQ No 1 | SEQ No 2 | | SEQ No 12 |
| SEQ No 4 | SEQ No 5 | SEQ NO 13 | SEQ No 23 | SEQ No 1 | SEQ No 2 | | SEQ No 12 |
| SEQ No 4 | SEQ No 20 | | SEQ No 15 | SEQ No 1 | SEQ No 2 | | SEQ No 12 |
| SEQ No 4 | SEQ No 20 | SEQ NO 13 | SEQ No 23 | SEQ No 1 | SEQ No 2 | | SEQ No 12 |
| SEQ No 4 | SEQ No 2 | SEQ NO 13 | SEQ No 11 | SEQ No 1 | SEQ No 21 | SEQ No 10 | SEQ No 24 |
| SEQ No 4 | SEQ No 2 | SEQ NO 13 | SEQ No 11 | SEQ No 1 | SEQ No 21 | SEQ No 10 | SEQ No 25 |
| SEQ No 4 | SEQ No 2 | SEQ NO 13 | SEQ No 11 | SEQ No 1 | SEQ No 22 | SEQ No 10 | SEQ No 24 |
| SEQ No 4 | SEQ No 2 | SEQ NO 13 | SEQ No 11 | SEQ No 1 | SEQ No 22 | SEQ No 10 | SEQ No 25 |
| SEQ No 4 | SEQ No 2 | SEQ NO 13 | SEQ No 11 | SEQ No 1 | SEQ No 5 | SEQ No 10 | SEQ No 14 |
| SEQ No 4 | SEQ No 2 | SEQ NO 13 | SEQ No 11 | SEQ No 1 | SEQ No 5 | SEQ No 10 | SEQ No 23 |
| SEQ No 4 | SEQ No 2 | SEQ NO 13 | SEQ No 11 | SEQ No 1 | SEQ No 20 | SEQ No 10 | SEQ No 14 |
| SEQ No 4 | SEQ No 2 | SEQ NO 13 | SEQ No 11 | SEQ No 1 | SEQ No 20 | SEQ No 10 | SEQ No 23 |

Design of the Linkers

The polypeptide linker, also designated "hinge-derived polypeptide linker sequence" or "pseudo hinge linker", comprises all or part of the sequence of the hinge region of one or more immunoglobulin(s) selected among IgA, IgG, and IgD, preferably of human origin. Said polypeptide linker may comprise all or part of the sequence of the hinge region of only one immunoglobulin. In this case, said immunoglobulin may belong to the same isotype and subclass as the immunoglobulin from which the adjacent CH1 domain is derived, or to a different isotype or subclass. Alternatively, said polypeptide linker may comprise all or part of the sequences of hinge regions of at least two immunoglobulins of different isotypes or subclasses. In this case, the N-terminal portion of the polypeptide linker, which directly follows the CH1 domain, preferably consists of all or part of the hinge region of an immunoglobulin belonging to the same isotype and subclass as the immunoglobulin from which said CH1 domain is derived.

Optionally, said polypeptide linker may further comprise a sequence of from 2 to 15, preferably of from 5 to 10 N-terminal amino acids of the CH2 domain of an immunoglobulin.

The polypeptide linker sequence typically consists of less than 80 amino acids, preferably less than 60 amino acids, still preferably less than 40 amino acids.

In some cases, sequences from native hinge regions can be used; in other cases point mutations can be brought to these sequences, in particular the replacement of one or more cysteine residues in native IgG1, IgG2 or IgG3 hinge sequences by alanine or serine, in order to avoid unwanted intra-chain or inter-chains disulfide bonds.

In a particular embodiment, the polypeptide linker sequence comprises or consists of amino acid sequence EPKX$_1$CDKX$_2$HX$_3$X$_4$PPX$_5$PAPELLGGPX$_6$X7PPX$_8$P-

$X_9PX_{10}GG$ (SEQ ID NO: 36), wherein $X_1$, $X_2$, $X_3$, $X_4$, $X_5$, $X_6$, $X_7$, $X_8$, $X_9$, $X_{10}$, identical or different, are any amino acid. In particular, the polypeptide linker sequence may comprise or consist of a sequence selected from the group consisting of

```
                                       (SEQ ID NO: 37)
EPKSCDKTHTSPPAPAPELLGGPGGPPGPGPGGG;

(SEQ ID NO: 3)
EPKSCDKTHTCPPCPAPELLGGPSTPPTPSPSGG;

(SEQ ID NO: 16)
EPKSCDKTHTSPPSPAPELLGGPSTPPTPSPSGG;

(SEQ ID NO: 34)
EPKSCDKTHTSPPAPAPELLGGPAAPPAPAPAGG;

(SEQ ID NO: 38)
EPKSCDKTHTSPPAPAPELLGGPAAPPGPAPGGG.
```

A non-limitative example of a hinge-derived polypeptide linker which can be used in a multispecific antigens-binding fragment of the invention is a polypeptide having SEQ ID NO: 3. Said polypeptide consists of the full length sequence of human IgG1 hinge, followed by the 9 N-terminal amino-acids of human IgG1 CH2 (APELLGGPS, SEQ ID NO: 28), by a portion of the sequence of human IgA1 hinge (TPPTPSPS, SEQ ID NO: 29), and by the dipeptide GG, added to provide supplemental flexibility to the linker. In another preferred embodiment, the hinge-derived polypeptide linker sequence is SEQ ID NO: 34 or SEQ ID NO: 16.

In a particular embodiment, $X_1$, $X_2$ and $X_3$, identical or different, are Threonine (T) or Serine (S).

In another particular embodiment, $X_1$, $X_2$ and $X_3$, identical or different, are selected from the group consisting of Ala (A), Gly (G), Val (V), Asn (N), Asp (D) and Ile (I), still preferably $X_1$, $X_2$ and $X_3$, identical or different, may be Ala (A) or Gly (G).

Alternatively, $X_1$, $X_2$ and $X_3$, identical or different, may be Leu (L), Glu (E), Gln (Q), Met (M), Lys (K), Arg (R), Phe (F), Tyr (T), His (H), Trp (W), preferably Leu (L), Glu (E), or Gln (Q).

In a particular embodiment, $X_4$ and $X_5$, identical or different, are any amino acid selected from the group consisting of Serine (S), Cysteine (C), Alanine (A), and Glycine (G).

In a preferred embodiment, $X_4$ is Serine (S) or Cysteine (C).

In a preferred aspect, $X_5$ is Alanine (A) or Cysteine (C).

In a particular embodiment, $X_6$, $X_7$, $X_8$, $X_9$, $X_{10}$, identical or different, are any amino acid other than Threonine (T) or Serine (S). Preferably $X_6$, $X_7$, $X_8$, $X_9$, $X_{10}$, identical or different, are selected from the group consisting of Ala (A), Gly (G), Val (V), Asn (N), Asp (D) and Ile (I).

Alternatively, $X_6$, $X_7$, $X_8$, $X_9$, $X_{10}$, identical or different, may be Leu (L), Glu (E), Gln (Q), Met (M), Lys (K), Arg (R), Phe (F), Tyr (T), His (H), Trp (W), preferably Leu (L), Glu (E), or Gln (Q).

In a preferred embodiment, $X_6$, $X_7$, $X_8$, $X_9$, $X_{10}$, identical or different, are selected from the group consisting of Ala (A) and Gly (G).

In still a preferred embodiment, $X_6$ and $X_7$ are identical and are preferably selected from the group consisting of Ala (A) and Gly (G).

In a preferred embodiment, the polypeptide linker sequence comprises or consists of sequence SEQ ID NO: 36, wherein $X_1$, $X_2$ and $X_3$, identical or different, are Threonine (T), Serine (S);

$X_4$ is Serine (S) or Cysteine (C);

$X_5$ is Alanine (A) or Cysteine (C);

$X_6$, $X_7$, $X_8$, $X_9$, $X_{10}$, identical or different, are selected from the group consisting of Ala (A) and Gly (G).

In another preferred embodiment, the polypeptide linker sequence comprises or consists of sequence SEQ ID NO: 36, wherein $X_1$, $X_2$ and $X_3$, identical or different, are Ala (A) or Gly (G);

$X_4$ is Serine (S) or Cysteine (C);

$X_5$ is Alanine (A) or Cysteine (C);

$X_6$, $X_7$, $X_8$, $X_9$, $X_{10}$, identical or different, are selected from the group consisting of Ala (A) and Gly (G).

Preferred Bispecific Antibodies

A preparation of several bispecific antibodies (designated BiXAb-3486, BiXAb-3489, BiXAb-3732SS, and BiXAb-E06528) is described in the Examples.

One preferred bispecific antibody of the invention (BiXAb-3486) has the following structure:

i) a continuous heavy chain which comprises
Trastuzumab heavy chain variable region (VH) corresponding to SEQ ID NO: 1
Wild-type CH1 constant domain (residue at Kabat position 192 is threonine, T) from human IgG1 corresponding to SEQ ID NO: 2
Polypeptide linker joining the 2 Fab heavy chains corresponding to SEQ ID NO: 3
Cetuximab heavy chain variable region (VH) corresponding to SEQ ID NO: 4
Mutated CH1 constant domain (residue at Kabat position 192 has been mutated from threonine to glutamic acid, E,) from human IgG1 corresponding to SEQ ID NO: 5
Wild-type Hinge region from human IgG1 corresponding to SEQ ID NO: 6
Wild-type CH2 domain of human IgG1 corresponding to SEQ ID NO: 7
Wild-type CH3 domain of human IgG1 allotype G1m(3) corresponding to SEQ ID NO: 8.

So, the bispecific antibody of the invention has a continuous heavy chain (701 residues) of SEQ ID NO: 9 ii) a wild-type trastuzumab light chain which comprises
A wild-type variable region (VL) corresponding to SEQ ID NO: 10
A wild-type human Kappa constant domain (residue at Kabat positions 114 and 137 are serine (S) and asparagine (N), respectively) corresponding to SEQ ID NO: 11

So, the Trastuzumab light chain corresponds to SEQ ID NO: 12 iii) a cetuximab light chain which comprises
A wild-type variable region (VL) corresponding to SEQ ID NO: 13
A mutated human Kappa constant domain (residue at Kabat positions 114 and 137 are alanine (A) and lysine (K), respectively) corresponding to SEQ ID NO: 14

So, Cetuximab light chain corresponds to SEQ ID NO: 15.

Another preferred bispecific antibody of the invention (BiXAb-3489) is the antibody having the following structure:

i) a continuous heavy chain which comprises
Trastuzumab heavy chain variable region (VH) corresponding to SEQ ID NO: 1

Wild-type CH1 constant domain (residue at Kabat position 192 is threonine, T) from human IgG1 corresponding to SEQ ID NO: 2
Polypeptide linker joining the 2 Fab heavy chains corresponding to SEQ ID NO: 16
Cetuximab heavy chain variable region (VH) corresponding to SEQ ID NO: 4
Mutated CH1 constant domain (residue at Kabat position 192 has been mutated from threonine to glutamic acid, E,) from human IgG1 corresponding to SEQ ID NO: 5
Wild-type Hinge region from human IgG1 corresponding to SEQ ID NO: 6
Wild-type CH2 domain of human IgG1 corresponding to SEQ ID NO: 7
Wild-type CH3 domain of human IgG1 allotype G1m(3) corresponding to SEQ ID NO: 8
So, the bispecific antibody of the invention has a continuous heavy chain (701 residues) of SEQ ID NO: 17
ii) a wild-type trastuzumab light chain which consists of SEQ ID NO: 12
iii) a cetuximab light chain which consists of SEQ ID NO: 15.

Another preferred bispecific antibody of the invention (BiXAb-E06528) is the antibody having the following structure:
i) a continuous heavy chain which comprises
Trastuzumab heavy chain variable region (VH) corresponding to SEQ ID NO: 1
Wild-type CH1 constant domain (residue at Kabat position 192 is threonine, T) from human IgG1 corresponding to SEQ ID NO: 2
Polypeptide linker joining the 2 Fab heavy chains corresponding to SEQ ID NO: 34
Cetuximab heavy chain variable region (VH) corresponding to SEQ ID NO: 4
Mutated CH1 constant domain (residue at Kabat position 192 has been mutated from threonine to glutamic acid, E,) from human IgG1 corresponding to SEQ ID NO: 5
Wild-type Hinge region from human IgG1 corresponding to SEQ ID NO: 6
Wild-type CH2 domain of human IgG1 corresponding to SEQ ID NO: 7
Wild-type CH3 domain of human IgG1 allotype G1m(3) corresponding to SEQ ID NO: 8.
So, the bispecific antibody of the invention has a continuous heavy chain (701 residues) of SEQ ID NO: 35
ii) a wild-type trastuzumab light chain which consists of SEQ ID NO: 12
iii) a cetuximab light chain which consists of SEQ ID NO: 15.

Another preferred bispecific antibody of the invention has the following structure:
i) a continuous heavy chain which comprises
Cetuximab heavy chain variable region (VH) corresponding to SEQ ID NO: 4
Mutated CH1 constant domain (residue at Kabat position 192 has been mutated from threonine to glutamic acid, E) from human IgG1 corresponding to SEQ ID NO: 5
Polypeptide linker joining the 2 Fab heavy chains corresponding to SEQ ID NO: 3
Trastuzumab heavy chain variable region (VH) corresponding to SEQ ID NO: 1
Wild-type CH1 constant domain (residue at Kabat position 192 is threonine, T) from human IgG1 corresponding to SEQ ID NO: 2
Wild-type Hinge region from human IgG1 corresponding to SEQ ID NO: 6
Wild-type CH2 domain of human IgG1 corresponding to SEQ ID NO: 7
Wild-type CH3 domain of human IgG1 allotype G1m(3) corresponding to SEQ ID NO: 8.
So, the bispecific antibody of the invention has a continuous heavy chain (701 residues) of SEQ ID NO: 18
ii) a wild-type trastuzumab light chain which consists of SEQ ID NO: 12
iii) a cetuximab light chain which consists of SEQ ID NO: 15.

Still another preferred bispecific antibody of the invention (BiXab 3732SS) has the following structure:
i) a continuous heavy chain which comprises
Cetuximab heavy chain variable region (VH) corresponding to SEQ ID NO: 4
Mutated CH1 constant domain (residue at Kabat position 192 has been mutated from threonine to glutamic acid, E) from human IgG1 corresponding to SEQ ID NO: 5
Polypeptide linker joining the 2 Fab heavy chains corresponding to SEQ ID NO: 16
Trastuzumab heavy chain variable region (VH) corresponding to SEQ ID NO: 1
Wild-type CH1 constant domain (residue at Kabat position 192 is threonine, T) from human IgG1 corresponding to SEQ ID NO: 2
Wild-type Hinge region from human IgG1 corresponding to SEQ ID NO: 6
Wild-type CH2 domain of human IgG1 corresponding to SEQ ID NO: 7
Wild-type CH3 domain of human IgG1 allotype G1m(3) corresponding to SEQ ID NO: 8.
So, the bispecific antibody of the invention has a continuous heavy chain (701 residues) of SEQ ID NO: 19
ii) a wild-type trastuzumab light chain which consists of SEQ ID NO: 12
iii) a cetuximab light chain which consists of SEQ ID NO: 15.

Mutated Derivatives

The invention makes use of wild-type sequences (of cetuximab or trastuzumab), or mutated derivates thereof.

The term "mutated derivative", "mutant", or "functional variant" designates a sequence that differs from the parent sequence to which it refers by deletion, substitution or insertion of one or several amino acids. Preferably the mutants preferably show at least 80%, preferably at least 85%, still preferably at least 90% homology sequence with the native sequence. In a particular embodiment, the mutations do not substantially impact the function of the antibody.

Mutated derivatives, or functional variants, can comprise a VH chain that comprises an amino acid sequence at least 85% (e.g., 90%, 92%, 94%, 95%, 96%, 97%, 98%, or 99%) identical to any of the reference sequences recited herein, a VL chain that has an amino acid sequence at least 85% (e.g., 90%, 92%, 94%, 95%, 96%, 97%, 98%, or 99%) identical to any of the reference sequences recited herein, or both. These variants are capable of binding to EGFR and HER2. In some examples, the variants possess similar antigen-binding affinity relative to the reference antibodies described above (e.g., having a Kd less than $1\times10^{-8}$, preferably less than $1\times10^{-9}$ or $1\times10^{-10}$ M).

The affinity of the binding is defined by the terms ka (associate rate constant), kd (dissociation rate constant), or KD (equilibrium dissociation). Typically, specifically binding when used with respect to an antibody refers to an antibody that specifically binds to ("recognizes") its target(s) with an affinity (KD) value less than $10^{-8}$ M, e.g., less than $10^{-9}$ M or $10^{-10}$ M. A lower KD value represents a higher binding affinity (i.e., stronger binding) so that a KD value of $10^{-9}$ indicates a higher binding affinity than a KD value of $10^{-8}$.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In other embodiments, the functional variants described herein can contain one or more mutations (e.g., conservative substitutions) which preferably do not occur at residues which are predicted to interact with one or more of the CDRs.

It is herein described mutated derivatives, or functional variants, which are substantially identical to the reference antibody.

The term "substantially identical" or "insubstantial" means that the relevant amino acid sequences (e.g., in framework regions (FRs), CDRs, VH, or VL domain) of a variant differ insubstantially (e.g., including conservative amino acid substitutions) as compared with a reference antibody such that the variant has substantially similar binding activities (e.g., affinity, specificity, or both) and bioactivities relative to the reference antibody. Such a variant may include minor amino acid changes, e.g. 1 or 2 substitutions in a 5 amino acid sequence of a specified region. Generally, more substitutions can be made in FR regions, in contrast to CDR regions, as long as they do not adversely impact the binding function of the antibody (such as reducing the binding affinity by more than 50% as compared to the original antibody). In some embodiment, the sequence identity can be about 85%, 90%, 95%, 96%, 97%, 98%, 99% or higher, between the original and the modified antibody. In some embodiments, the modified antibody has the same binding specificity and has at least 50% of the affinity of the original antibody.

Conservative substitutions will produce molecules having functional and chemical characteristics similar to those of the molecule from which such modifications are made. For example, a "conservative amino acid substitution" may involve a substitution of a native amino acid residue with another residue such that there is little or no effect on the polarity or charge of the amino acid residue at that position. Desired amino acid substitutions (whether conservative or non-conservative) can be determined by those skilled in the art. For example, amino acid substitutions can be used to identify important residues of the molecule sequence, or to increase or decrease the affinity of the molecules described herein. Variants comprising one or more conservative amino acid substitutions can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

The present disclosure also provides antibody variants with improved biological properties of the antibody, such as higher or lower binding affinity, or with altered ADCC properties, or with altered effects of viability inhibition of EGFR and/or HER2 expressing cells.

Amino acid sequence variants of the antibody can be prepared by introducing appropriate nucleotide changes into the antibody nucleic acid, or via peptide synthesis. Such modifications include, for example, deletions from, and/or insertions into and/or substitutions of, residues within the amino acid sequences of the antibody. Any combination of deletion, insertion, and substitution is made to achieve the final construct, provided that the final construct possesses the desired characteristics. Nucleic acid molecules encoding amino acid sequence variants of the antibody can be prepared by a variety of methods known in the art. These methods include, but are not limited to, oligonucleotide-mediated (or site-directed) mutagenesis, PCR mutagenesis, and cassette mutagenesis of an earlier prepared variant or a non-variant (natural) version of the antibody. In one embodiment, the equilibrium dissociation constant (KD) value of the antibodies of the invention is less than $10^{-8}$ M, particularly less than $10^{-9}$ M or $10^{-10}$ M. The binding affinity may be determined using techniques known in the art, such as ELISA or biospecific interaction analysis, or other techniques known in the art.

Any of the antibodies described herein can be examined to determine their properties, such as antigen-binding activity, antigen-binding specificity, and biological functions, following routine methods.

Any of the antibodies described herein can be modified to contain additional nonproteinaceous moieties that are known in the art and readily available, e.g., by PEGylation, hyperglycosylation, conjugation of toxins, radioactive labels and the like. Modifications that can enhance serum half-life are of interest.

Examples of mutated derivatives are described below.

According to the invention, bispecific antibodies are described, which comprise

- a mutated CH1 constant domain (residue at Kabat position 192 has been mutated from threonine to aspartic acid, D) from human IgG1 corresponding to SEQ ID NO: 20
- a mutated CH1 constant domain (residue at Kabat position 192 has been mutated from threonine to lysine, K from human IgG1 corresponding to SEQ ID NO: 21
- a mutated CH1 constant domain (residue at Kabat position 192 has been mutated from threonine to arginine, R) from human IgG1 corresponding to SEQ ID NO: 22
- a mutated human Kappa constant domain (residue at Kabat positions 114 and 137 are alanine (A) and arginine (R), respectively) corresponding to SEQ ID NO: 23
- a mutated human Kappa constant domain (residue at Kabat positions 114 and 137 are alanine (A) and glutamic acid (E), respectively) corresponding to SEQ ID NO: 24
- or a mutated human Kappa constant domain (residue at Kabat positions 114 and 137 are alanine (A) and aspartic acid (D), respectively) corresponding to SEQ ID NO: 25.

In another embodiment, residues at the following Kabat positions could be mutated in the VH and VL sequences of trastuzumab:

In VH at Kabat position 31, Asp to Glu or Ser
In VH at Kabat position 32, Thr to Ser, Asn or Tyr
In VH at Kabat position 54, Asn to Gln, His, Lys, Arg, Gly or Ser
In VH at Kabat position 55, Gly to Pro, Ala and Ser
In VH at Kabat position 61, Asp to Glu
In VH at Kabat position 62, Ser to Thr
In VH at Kabat position 95, Trp to Tyr or Phe
In VH at Kabat position 98, Asp to Glu
In VH at Kabat position 99, Gly to Pro or Ala
In VL at Kabat position 28, Asp to Glu or Gly
In VL at Kabat position 29, Val to Ile or Leu
In VL at Kabat position 30, Asn to Gln, His, Lys, Arg or Ser
In VL at Kabat position 31, Thr to Ser.

The antibodies of the invention may be glycosylated or not, or may show a variety of glycosylation profiles. In a preferred embodiment, antibodies are unglycosylated on the variable region of the heavy and light chains, but are glycosylated on the Fc region.

For example to remove the N-glycosylation site in the VH domain of cetuximab, the Asn at Kabat position H85 is mutated to aspartic acid (D) according the sequence SEQ ID NO:26, or the Asn at Kabat position H85 is mutated to glutamic acid (E) according the sequence SEQ ID NO:27.

Certain mutated derivatives may use humanized forms of the reference cetuximab antibody, which, in its original form, is a chimeric antibody with heavy and light chain variable regions of murine origin. In a humanization approach, complementarity determining regions (CDRs) and certain other amino acids from donor mouse variable regions are grafted into human variable acceptor regions and then joined to human constant regions. See, e.g. Riechmann et al., Nature 332:323-327 (1988); U.S. Pat. No. 5,225,539.

In some examples, it is described bispecific antibodies which comprise
a Light chain humanized version of cetuximab based on human immunoglobulin gene kappa variable 6-11 allele 02 (IGKV6-11*02) as defined in IMGT/Gene database, (SEQ ID NO: 30)
EIVLTQSPDFQSVTPKEKVTITCRASQSIGTNIHWYQQKPDQSPKLLIKY
ASESISGVPSRFSGSGSGTDFTLTINSLEAEDAATYYCQQNNNWPTTFGQ
GTKLEIK Where at the following Kabat positions the amino acid residues are:
Kabat position L31 a Thr or Ser
Kabat position L32 an Asn or Ser
Kabat position L33 a Ile or Leu
Kabat position L53 a Glu or Gln
Kabat position L89 a Gln or His
Kabat position L91 an Asn, Ser, His, Lys or Arg
Kabat position L92 an Asn, Ser, His, Lys or Arg
Kabat position L93 an Asn, Ser, His, Lys or Arg
Kabat position L94 a Trp, Tyr or Phe
Kabat position L96 a Thr or Tyr.
a Light chain humanized version of cetuximab based on human immunoglobulin gene kappa variable 3-11 allele 01 (IGKV3-11*01) as defined in IMGT/Gene database, (SEQ ID NO: 31)
EIVLTQSPATLSLSPGERATLSCRASQSIGTNIHWYQQKPGQAPRLLIKY
ASESISGIPARFSGSGSGTDFTLTISSLEPEDFAVYYCQQNNNWPTTFGQ
GTKLEIK Where at the following Kabat positions the amino acid residues are:
Kabat position L29 an Ile or Val
Kabat position L30 a Gly or Ser
Kabat position L31 a Thr or Ser
Kabat position L32 an Asn or Tyr
Kabat position L33 a Ile or Leu
Kabat position L34 a His or Ala
Kabat position L49 a Lys or Tyr
Kabat position L50 a Tyr or Asp
Kabat position L53 a Glu or Asn
Kabat position L54 a Ser or Arg
Kabat position L55 an Ile or Ala
Kabat position L56 a Ser or Thr
Kabat position L91 an Asn, Arg, His, or Lys
Kabat position L92 an Asn, Ser, His, Lys or Arg
Kabat position L94 a Trp, Tyr or Phe
Kabat position L96 a Thr or Tyr.
a Heavy chain humanized version of cetuximab mAb based on human immunoglobulin gene heavy variable 4-59 allele 01 (IGHV4-59*01) as defined in IMGT/Gene database, (SEQ ID NO: 32)
QVQLQESGPGLVKPSETLSLTCTVSGFSLTNYGVHVVVRQPPGKGLEWLG
VIWSGGNTDYNTPLTSRLTISKDNSKNQVSLKLSSVTAADTAVYYCARAL
TYYDYEFAYWGQGTLVTVSS Where at the following Kabat positions the amino acid residues are:
Kabat position H29 a Leu or Ile
Kabat position H30 a Thr or Ser
Kabat position H31 an Asn or Ser
Kabat position H33 a Gly or Tyr
Kabat position H35 a His or Ser
Kabat position H37 a Val or Ile
Kabat position H48 a Leu or Ile
Kabat position H50 at Val or Tyr
Kabat position H52 a Trp, Tyr or Phe
Kabat position H53 a Ser or Tyr
Kabat position H54 a Gly or Ser
Kabat position H56 an Asn or Ser
Kabat position H58 a Asp or Asn
Kabat position H61 a Thr or Pro
Kabat position H62 a Pro or Ser
Kabat position H64 a Thr or Lys
Kabat position H67 a Leu or Val
Kabat position H73 a Asn or Thr
Kabat position H78 a Val or Phe.
a Heavy chain humanized version of cetuximab mAb based on human immunoglobulin gene heavy variable 3-33 allele 01 (IGHV3-33*01) as defined in IMGT/Gene database, (SEQ ID NO: 33)
QVQLVESGGGVVQPGRSLRLSCAVSGFSLTNYGVHWVRQAPGKGLEWLGV
IWSGGNTDYNTPVTSRFTISKDNSKNTVYLQMNSLRAEDTAVYYCARALT
YYDYEFAYWGQGTLVTVSS Where at the following Kabat positions the amino acid residues are:
Kabat position H28 a Ser or Thr
Kabat position H30 a Thr or Ser
Kabat position H48 a Leu or Val
Kabat position H49 a Gly or Ala
Kabat position H53 a Ser or Asp
Kabat position H55 a Gly or Ser
Kabat position H57 a Lys or Thr
Kabat position H58 a Asp or Tyr
Kabat position H60 an Asn or Ala
Kabat position H61 a Thr or Asp
Kabat position H62 a Pro or Ser
Kabat position H64 a Thr or Lys
Kabat position H65 a Ser or Gly
Kabat position H78 a Val or Leu.

Production of the Antibodies

Nucleic acids encoding heavy and light chains of the antibodies of the invention are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence. Expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences.

In one example, both the heavy and light chain coding sequences (e.g., sequences encoding a VH and a VL, a VH-CH1 and a VL-CL, or a full-length heavy chain and a full-length light chain) are included in one expression vector. In another example, each of the heavy and light chains of the antibody is cloned into an individual vector. In the latter case, the expression vectors encoding the heavy and light chains can be co-transfected into one host cell for expression of both chains, which can be assembled to form intact antibodies either in vivo or in vitro. Alternatively, the expression vector encoding the heavy chain and that or those encoding the light chains can be introduced into different host cells for expression each of the heavy and light chains, which can then be purified and assembled to form intact antibodies in vitro.

In a particular embodiment, a host cell is co-transfected with three independent expression vectors, such as plasmids, leading to the coproduction of all three chains (namely the heavy chain HC, and two light chains LC1 and LC2, respectively) and to the secretion of the bispecific antibody.

More especially the three vectors may be advantageously used in a following molecular ratio of 2:1:1 (HC:LC1:LC2).

The recombinant vectors for expression the antibodies described herein typically contain a nucleic acid encoding the antibody amino acid sequences operably linked to a promoter, either constitutive or inducible. The vectors can be suitable for replication and integration in prokaryotes, eukaryotes, or both. Typical vectors contain transcription and translation terminators, initiation sequences, and promoters useful for regulation of the expression of the nucleic acid encoding the antibody. The vectors optionally contain generic expression cassettes containing at least one independent terminator sequence, sequences permitting replication of the cassette in both eukaryotes and prokaryotes, i.e., shuttle vectors, and selection markers for both prokaryotic and eukaryotic systems.

Bispecific antibodies as described herein may be produced in prokaryotic or eukaryotic expression systems, such as bacteria, yeast, filamentous fungi, insect, and mammalian cells. It is not necessary that the recombinant antibodies of the invention be glycosylated or expressed in eukaryotic cells; however, expression in mammalian cells is generally preferred. Examples of useful mammalian host cell lines are human embryonic kidney line (293 cells), baby hamster kidney cells (BHK cells), Chinese hamster ovary cells/– or +DHFR (CHO, CHO-S, CHO-DG44, Flp-in CHO cells), African green monkey kidney cells (VERO cells), and human liver cells (Hep G2 cells).

Mammalian tissue cell culture is preferred to express and produce the polypeptides because a number of suitable host cell lines capable of secreting intact immunoglobulins have been developed in the art, and include the CHO cell lines, various Cos cell lines, HeLa cells, preferably myeloma cell lines, or transformed B-cells or hybridomas.

In a most preferred embodiment, the bispecific antibodies of the invention are produced by using a CHO cell line, most advantageously a CHO-S or CHO-DG-44 cell lines or their derivatives.

Expression vectors for these cells can include expression control sequences, such as an origin of replication, a promoter, and an enhancer, and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like.

The vectors containing the polynucleotide sequences of interest (e.g., the heavy and light chain encoding sequences and expression control sequences) can be transferred into the host cell by well-known methods, which vary depending on the type of cellular host. For example calcium phosphate treatment or electroporation may be used for other cellular hosts. (See generally Sambrook et al., Molecular Cloning: A Laboratory Manual (Cold Spring Harbor Press, 2nd ed., 1989). When heavy and light chains are cloned on separate expression vectors, the vectors are co-transfected to obtain expression and assembly of intact immunoglobulins.

Host cells are transformed or transfected with the vectors (for example, by chemical transfection or electroporation methods) and cultured in conventional nutrient media (or modified as appropriate) for inducing promoters, selecting transformants, or amplifying the genes encoding the desired sequences.

The expression of the antibodies may be transient or stable.

Preferably, the bispecific antibodies are produced by the methods of stable expression, in which cell lines stably transfected with the DNA encoding all polypeptide chains of a bispecific antibody, such as BiXAb-3486, BiXAb-3489, BiXAb-3732SS and BiXAb-E06528, are capable of sustained expression, which enables manufacturing of therapeutics. For instance stable expression in a CHO cell line is particularly advantageous.

Once expressed, the whole antibodies, their dimers, individual light and heavy chains, or other immunoglobulin forms of the present invention can be further isolated or purified to obtain preparations that substantially homogeneous for further assays and applications. Standard protein purification methods known in the art can be used. For example, suitable purification procedures may include fractionation on immunoaffinity or ion-exchange columns, ethanol precipitation, high-performance liquid chromatography (HPLC), sodium dodecyl sulfate polyacrylamide gel electrophoresis (SDS-PAGE), ammonium sulfate precipitation, and gel filtration (see generally Scopes, Protein Purification (Springer-Verlag, N.Y., 1982). Substantially pure immunoglobulins of at least about 90 to 95% homogeneity are preferred, and 98 to 99% or more homogeneity most preferred, for pharmaceutical uses.

In vitro production allows scale-up to give large amounts of the desired bispecific antibodies of the invention. Such methods may employ homogeneous suspension culture, e.g. in an airlift reactor or in a continuous stirrer reactor, or immobilized or entrapped cell culture, e.g. in hollow fibers, microcapsules, on agarose microbeads or ceramic cartridges.

Therapeutic Uses

The bispecific antibodies of the invention have been shown to induce tumor growth inhibition.

The bispecific antibody of the invention is useful as a medicament, in particular in treating a cancer.

The term "cancer" as used herein includes any cancer, especially pancreatic cancer and any other cancer characterized by EGFR or HER2 expression or overexpression, and especially those cancers characterized by co-expression of both EGFR and HER2.

In some embodiments, the cancer comprises cells with a wild-type KRAS gene.

Examples of cancers are solid tumors such as pancreatic cancer, head and neck cancer, including squamous cell carcinoma, colorectal cancer, breast cancer, lung cancer, gastric cancer, ovarian cancer.

It is thus described a method of treatment of a patient suffering from cancer by administering an antibody according to the invention to said patient in the need of such treatment. Another aspect of the invention is thus the use of the bispecific antibodies according to the invention for the manufacture of a medicament for the treatment of cancer.

One aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention.

In another aspect, the present invention provides a composition, e.g. a pharmaceutical composition, containing an antibody as defined herein, formulated together with a pharmaceutical carrier.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. The route and/or mode of administration will vary depending upon the desired results.

To administer the bispecific antibody of the invention by certain routes of administration, it may be necessary to coat the bispecific antibody of the invention with, or co-administer the bispecific antibody of the invention with a material to prevent its inactivation. For example, the bispecific antibody of the invention may be administered to a subject in an appropriate carrier, for example, liposomes, or a diluent.

Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol, sorbic acid, and the like. It may also be desirable to include isotonic agents, such as sodium chloride into the compositions. In addition, prolonged absorption of the injectable pharmaceutical form may be brought about by the inclusion of agents which delay absorption.

Actual dosage levels of the active ingredients in the pharmaceutical compositions of the present invention may be varied so as to obtain an amount of the active ingredient, which is effective to achieve the desired therapeutic response for a particular patient, composition, and mode of administration, without being toxic to the patient.

The selected dosage level will depend upon a variety of pharmacokinetic factors including the activity of the particular compositions of the present invention employed, the route of administration, the time of administration, the duration of the treatment, other drugs, compounds and/or materials used in combination with the particular compositions employed, the age, sex, weight, condition, general health and prior medical history of the patient being treated, and like factors well known in the medical arts. For example the bispecific antibody of the invention can be administrated at a dosage of 0.2-20 mg/kg from 3 times/week to 1 time/month.

The present invention, thus generally described above, will be understood more readily by reference to the following examples, which are provided by way of illustration and are not intended to be limiting the instant invention. The examples are not intended to represent that the experiments below are all or the only experiments performed.

EXAMPLES

Example 1. Preparation of the Bispecific Antibodies of the Invention BIXAb-3486, BIXAb-3489 and BIXAb-3732SS Gene Synthesis The amino acid sequences of anti-HER2 (trastuzumab, clone humAb4D5-8) ((Carter P., Presta L., Gorman C. M., Ridgway J. B., Henner D., Wong W. L., Rowland A. M., Kotts C., Carver M. E., Shepard H. M. (1992) Humanization of an anti-p185HER2 antibody for human cancer therapy. Proc Nat Acad Sci USA. 15, 4285-4289) and anti-EGFR (cetuximab) ((Humblet Y. (2004). Cetuximab: an IgG1 monoclonal antibody for the treatment of epidermal growth factor receptor expressing tumors. Expert Opin Pharmacother 5: 1621-1633.) were used to design the DNA sequences after codon optimization for mammalian expression using GeneScript program. For the heavy chain, the DNAs encoding signal peptides, variable region and constant CH1 domain of Fab1 followed the pseudo hinge linker and variable region and constant CH1 domain of Fab2 with flanking sequences for restriction enzyme digestion were synthesized by GeneScript. For the light chain, the DNAs encoding signal peptides and variable and constant Kappa regions were synthesized by GeneScript.

PCR reactions using PfuTurbo Hot Start were carried out to amplify the inserts which were then digested by NotI+ApaI and NotI+HindIII for heavy and light chains, respectively. The double digested heavy chain fragments were ligated with NotI+ApaI treated pcDNA3.1 expression vector (Invitrogen) in which the human IgG1 CH1+hinge+CH2+CH3 domains were already inserted. The double digested light chain fragments were ligated with NotI+HindIII treated pcDNA3.1 expression vector (Invitrogen). Plasmid DNAs were verified by double strand DNA sequencing.

Expression and Purification of Variants

The bispecific antibodies of the invention (also referred to as "BiXAb" molecules) were produced by means of transient gene expression by co-transfection of 3 genes coded on separate vectors in a 2:1:1=HC:LC1:LC2 molecular ratio (1 continuous heavy chain (HC) and 2 light chains (LC)) in CHO-S cells adapted to serum-free medium in suspension (CHO SFM-II medium from LIFE TECHNOLOGIES). Typically, for 50 mL medium scale expression testing, a total of 50 µg of plasmid DNAs (25 µg heavy chain1, 12.5 µg of trastuzumab (anti-HER2) light chain and 12.5 µg of cetuximab (anti-EGFR) light chain were mixed in 1.5 mL Eppendorf tube, 1 mL of CHO SFM medium containing 25 µL of 3 mg/mL PEI transfection reagent (Polyplus) pH7.0 was added, incubated at RT for 20 min. The mixture of DNA-PEI was loaded into 49 mL of LIFE TECHNOLOGIES' INVITROGEN FREESTYLE CHO-S cells at $1\sim2\times10^6$/mL in 125 mL shaking flask. Cells were shaken for 6 more days. The supernatant was harvested by centrifuging cells at 3,000 rpm for 15 min. The expression titer of the BiXAbs in the supernatant was determined using FortéBio's protein A biosensors (OCTET Systems). The bispecific monoclonal antibody (BiXAb) was then purified on protein An affinity medium using MabSelect SuRe (GE Healthcare Life Sciences). The antibody was eluted from protein A using 0.1 M glycine pH 3.5 with neutralization in 1 M TRIS. The purified antibody in Dulbecco's PBS (Lonza BE17-512Q) was sterile-filtered (0.2 µM sterile filters from Techno Plastic Products AG) and the final concentration determined by OD reading at 280 nm using Eppendorf BIOSPECTROMETER.

SDS Polyacrylamide Gel Electrophoresis Analysis

The SDS-PAGE analysis of purified BiXAb-3486, BiXAb-3489, and BiXAb-3732SS antibodies was performed by using Experion™ automated electrophoresis system from BioRad. In the presence of sodium laurylsulfate (SDS) in the buffer the rate at which the antibody migrates in the gel depends primarily on its size, enabling molecular weight determination.

The SDS-PAGE profile is presented in FIGS. 2A and 2B. Lanes 1 and 2 in FIG. 2A show the profile obtained under non-reducing (left) and reducing (right) conditions for BiXAb-3732SS and BiXAb-3489, respectively. FIG. 2B demonstrates the SDS-PAGE profile (reducing and non-reducing) for BiXAb-3486.

Under non-reducing conditions, the quaternary structure of the antibody is maintained and the molecular mass observed should represent the sum of the molecular weight of the different heavy and light chains.

The bispecific antibody format of the invention consists of six chains: 2 heavy and 4 light chains. The theoretical molecular mass, without taking into account post translational modifications (PTM), e.g. N-glycosylation, is 245.50, 245.44 and 245.451 kDa for BiXAb-3486, BiXAb-3489, and BiXAb-3732SS, respectively. The non-reducing gels (FIGS. 2A and 2B) were calibrated using standards of known molecular mass. The profiles obtained in Lane 1 and 2 (FIG. 2A) and Lane 1 (FIG. 2B) show a major broad band at and above the 260 kDa standard molecular weight, which is in accordance with the calculated molecular weight of 245 kDa without PTM. BiXAb-3489, BiXAb-3732SS, and BiXAb-3486 have four N-glycosylation sites in their heavy chains, two in the Fc region (one on each heavy chain) as found in all conventional monoclonal antibodies at N297, and two in each Fabs (one on each heavy chain in the variable region of cetuximab at N88).

Under reducing conditions, a reducing agent dithiothreitol (DTT) further denatures the BiXAb proteins by reducing disulfide linkages and breaks the quaternary structure of the BiXAb molecules.

The 6 polypeptide chains migrate separately in the gel according to their relative molecular mass; the two heavy chains which have exactly the same molecular mass and the 2 pairs of light chains from anti-EGFR and anti-HER2 Fab domains.

The profiles obtained in reduced gel demonstrate the presence of 2 groups of major bands, one around 75 kDa and the second one around 25 kDa based on the mobility of molecular weight standards. As discussed in the section above, each heavy chain possesses 2 N-glycosylation sites, which explain the broadness of the band, typical mark of a glycosylated protein and its apparent molecular mass, which is higher than the calculated mass.

Though the calculated molecular masses of anti-EGFR (23.425 kDa) and anti-HER2 (23.443 kDa) light chains are similar they permit separation on the gel probably due to the difference in the hydrodynamic properties of each light chain.

All molecules, BiXAb-3486, BiXAb-3489, and BiXAb-3732SS, have a good expression level (~200 mg/L) by means of transient expression in CHO cells. This level of expression is comparable to the level of expression seen with conventional monoclonal antibodies like that of one of the parent antibodies, anti-EGFR.

In conclusion, the profile obtained by SDS-PAGE analysis for BiXAb-3486, BiXAb-3489, and BiXAb-3732SS is very similar and is in agreement with the calculated theoretical molecular weights. The differences in molecular mass are likely due to the presence of PTM, and especially the presence of 4 N-glycosylation sites in two heavy chains.

Size Exclusion Chromatography Analysis

Protein aggregation is frequently observed in engineered protein molecules. We performed analytical size exclusion chromatography (SEC) to assay the high molecular weight species content of the single-step affinity-purified BiXAb-3489 and BiXAb-3732SS preparation. We employed a SEC-s3000 (300×7.8 mm) column (BioSep) and an Aktapurifier 10 system (GE Healthcare); the assay was conducted at a flow rate of 1 mL/min using PBS buffer pH 7.4.

Figure 3A:
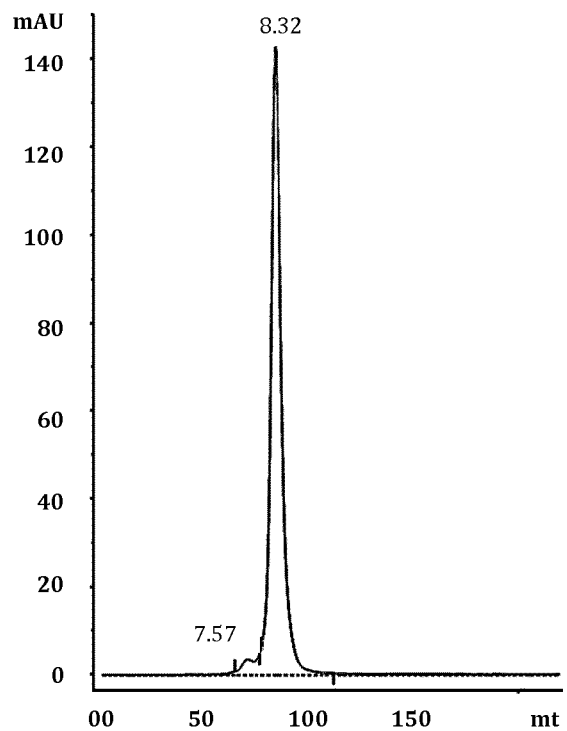
FIG. 3A shows the Size Exclusion chromatography analysis of BiXAb-3489.
Figure 3B:
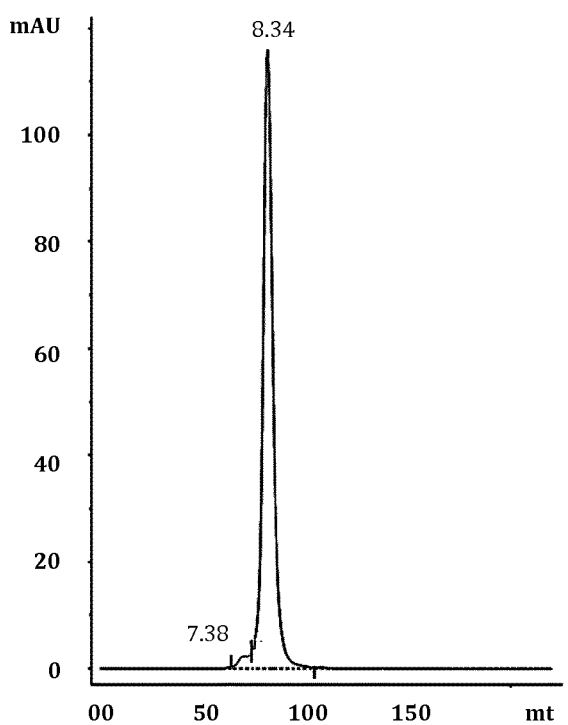
FIG. 3B shows the Size Exclusion chromatography analysis of BiXAb-3732SS.

The SEC chromatograms presented in FIGS. 3A and 3B demonstrated that the main peak in both chromatograms corresponded to the expected size of the monomeric BiXAb-3489 and BiXAb-3732SS representing 96.4% and 97.4%, respectively, of total samples. In addition, a small peak corresponding to higher molecular weight species (possibly dimers) was observed for BiXAb-3489 and BiXAb-3732SS; this peak represented 3.6% and 2.6%, respectively, of the total sample. Thus, we concluded that the percentage content of higher molecular weight species is minor, and is similar to conventional monoclonal antibodies produced in CHO expression systems. The narrow and symmetric shape of the monomeric peak suggested that both BiXAb-3489 and BiXAb-3732SS were correctly assembled and were represented by single species.

Example 2. Preparation of Bispecific Antibody of the Invention BIXAb-E06528

Gene Synthesis

The amino acid sequences of anti-EGFR (cetuximab) and anti-HER2 (trastuzumab) were used to design the DNA sequences, after codon optimization for mammalian expression, using the GeneScript program. These antibodies are referred to as the "parental" anti-EGFR and the "parental" anti-HER2 mAbs.

The DNA construct of the heavy chain was designed as such: signal peptide followed by a sequence consisting of the variable region, followed by the constant CH1 domain of Fab1 (anti-HER2) followed by the AP linker, followed by the variable region, followed by the constant CH1 domain of Fab2 (anti-EGFR), in which mutation Thr to Glu at Kabat position 192 was introduced; flanking sequences for restriction enzyme digestion were introduced on both ends of the heavy chain DNA construct. The DNA construct for the light chain was designed as such: signal peptide, followed by the variable region, followed by the constant Kappa region. For the anti-EGFR light chain, mutations at Kabat positions 137 (Asn to Lys) and 114 (Ser to Ala) were introduced into the constant Kappa domain. All DNA constructs were synthesized by Gene Art.

PCR reactions, using PfuTurbo Hot Start, were carried out to amplify the inserts, which were then digested with NotI and ApaI, and NotI and HindIII for heavy and light chains, respectively. The double digested heavy chain fragments were ligated with NotI and ApaI treated pcDNA3.1 expression vector (Invitrogen) into which the human IgG1 hinge followed by the CH2-CH3 domains were already inserted. The double-digested light chain fragments were ligated with NotI and HindIII treated pcDNA3.1 expression vector (Invitrogen). Plasmid DNAs were verified by double strand DNA sequencing.

Expression and Purification

The bispecific antibody BiXAb-E06528 was produced employing transient gene expression by co-transfecting 3 genes coded on separate vectors in a 2:1:1=HC:LC1:LC2 molecular ratio (1 continuous heavy chain (HC) and 2 light chains (LC)) in CHO-S cells adapted to serum-free medium in suspension (CHO SFM-II medium, Life Technologies). Typically, for 50 mL scale expression, a total of 50 μg of plasmid DNA (25 μg heavy chain, 12.5 μg of anti-HER2 light chain and 12.5 μg of anti-EGFR light chain) were mixed in a 1.5 mL Eppendorf tube, then 1 mL of CHO SFM medium containing 25 μL of 3 mg/mL PEI transfection reagent pH7.0 (Polyplus) was added, and the reaction incubated at room temperature for 20 min. The DNA-PEI mixture was subsequently added to 49 mL of Life Technologies' Invitrogen FreeStyle™ CHO-S cells at $1\sim2\times10^6$/mL in a 125 mL shake flask. Cells were shaken for 6 days. The supernatant was harvested by centrifugation at 3,000 rpm for 15 min. The expression titer of BiXAb-E06528 in the supernatant was determined using ForteBio's protein A biosensors (OCTET Systems). BiXAb-E06528 was then purified on protein A affinity resin (MabSelect SuRe, GE Healthcare Life Sciences). The antibody was eluted from protein A using 0.1 M glycine pH 3.5, and the eluate was neutralized by 1 M TRIS. The purified antibody, in Dulbecco's PBS (Lonza), was sterile-filtered (0.2 μM sterile filters, Techno Plastic Products AG), and the final concentration determined by reading the optical density (OD) at 280 nm (Eppendorf BIOSPECTROMETER).

BiXAab-E06528 typically exhibited good expression titer (>180 mg/liter) in transient CHO expression. This level of expression is comparable to the level of expression seen with conventional monoclonal antibodies.

SDS Polyacrylamide Gel Electrophoresis

In order to evaluate the quality of purified BiXAb-E06528, we performed SDS-PAGE. In the presence of sodium dodecyl sulfate (SDS) in the running buffer, the rate at which an antibody migrates in the gel depends primarily on its size, enabling molecular weight determination. This assay was performed under non-reducing conditions and under reducing conditions; the latter permits disruption of the disulfide bonds, and hence visualization of individual polypeptide chains (the light chains and the heavy chain).

The SDS-PAGE data are presented in FIG. 2C. Under non-reducing conditions, the quaternary structure of the antibody is maintained, and the molecular weight observed should represent the sum of the molecular weights of the different heavy and light chains. The bispecific antibody of the invention (BiXAb-E06528) consists of six chains: two heavy chains and four light chains. The theoretical molecular weight of BiXAb-E06528 is 245.139 kDa, not accounting for post-translational modifications (PTM), e.g. N-glycosylation in the Fc at asparagine 297. The gel was calibrated using a mixture of standards of known molecular weight. The non-reducing data exhibit a major band running close to the 250 kDa molecular weight standard, which is in accordance with the calculated molecular weight and the expected glycosylation of two asparagines at position 297 in the Fc domain. Under reducing conditions, dithiothreitol (DTT) further denatures BiXAb-E06528 by reducing the disulfide linkages and breaking the quaternary structure, and thus the six polypeptide chains should migrate separately in the gel according to their molecular weight. The two identical heavy chains of BiXAb-E06528 co-migrate as a single band, and the two pairs of light chains, due to their nearly identical molecular weight, co-migrated as the second band. Therefore, the data exhibit two major groups of bands, at approximately 75 kDa and 25 kDa, based on the mobility of the molecular weight standards. Each heavy chain possessed one N-glycosylation site at asparagine 297, which explains the broadness of the higher molecular weight band and the observed molecular weight slightly higher than calculated (75.701 kDa); this broadening is typical for glycosylated proteins. Though the calculated molecular weights of the light chains of anti-HER2 (23.443 kDa) and anti-EGFR (23.425 kDa) are similar, they permit separation on the gel probably due to the difference in the hydrodynamic properties of each light chain.

In conclusion, the SDS-PAGE of BiXAb-E06528 exhibited the expected profiles, under both non-reducing and reducing conditions, and was in agreement with the calculated theoretical molecular weights, when accounting for the existence of an N-glycosylation site in the heavy chain.

Size Exclusion Chromatography Analysis

Protein aggregation is frequently observed in engineered protein molecules. We performed analytical size exclusion chromatography (SEC) to assay the high molecular weight species content of the single-step affinity-purified BiXAb-6567 preparation (see Expression and Purification of variants). We employed an SEC-s3000 (300×7.8 mm) column (BioSep) and an Aktapurifier 10 system (GE Healthcare); the assay was conducted at a flow rate of 1 mL/min using PBS buffer pH 7.4.

Figure 3C:
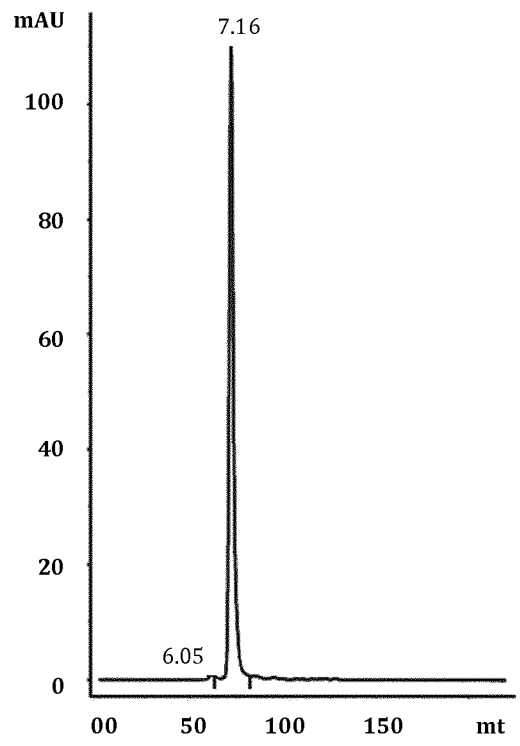
FIG. 3C shows the Size Exclusion chromatography analysis of BiXAb-E06528.

The SEC chromatogram presented in FIG. 3C demonstrated that the main peak corresponded to the expected size of the monomeric BiXAb-E06528; this peak represented 99.9% of the total sample. Thus, BiXAb-E06528 demonstrates no aggregates or higher molecular weight species and could be produced as a homogenous antibody after a single step affinity chromatography. The narrow and symmetric shape of the monomeric peak suggested that BiXAb-E06528 was correctly assembled and was represented by a single species.

Example 3. Characterization by Differential Scanning Calorimetry

Differential Scanning Calorimetry (DSC) was used to compare the thermal stability of BiXAb-3489, the parental anti-HER2 mAb, and the parental anti-EGFR mAb. A Microcal™ VP-Capillary DSC system (Malvern Instruments) was used to perform differential scanning calorimetry experiments.

All samples were centrifuged (20,000× g, 5 min, 4° C.), and their protein content was quantitated prior to the DSC analysis using a Nanodrop ND-1000 spectrophotometer (Thermo Scientific) employing the IgG analysis program. For assay, all samples were diluted in PBS to a final concentration of 1 mg/mL.

The pre-equilibration time was 3 min, and the resulting thermograms were acquired between 20 and 110° C. at a scan rate of 60° C./h, a filtering period of 25 sec, and medium feedback. Prior to sample analysis, 5 buffer/buffer scans were measured to stabilize the instrument, and a buffer/buffer scan was performed between each protein/buffer scan. The data were fit to a non-2-state unfolding model, with the pre- and post-transition adjusted by subtraction of the baseline.

Figure 4:
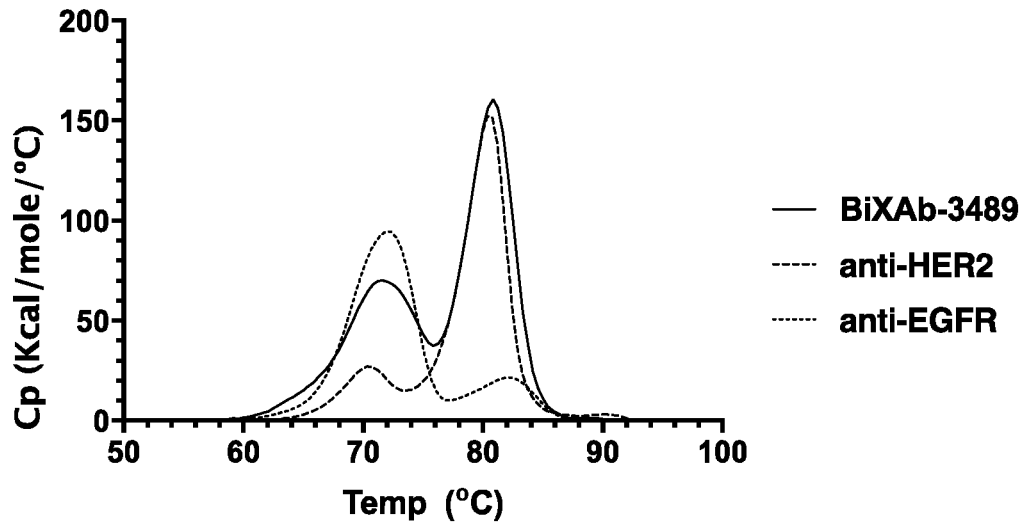
FIG. 4 shows the melting profiles of the two parental antibodies (anti-HER2 and anti-EGFR) and BiXAb-3489 as determined by Digital Scanning Calorimetry.

The DSC curves presented in FIG. 4 (covering the 50 to 100° C. range) demonstrated the manner in which individual Fv regions can lead to different Fab unfolding profiles; this experiment also demonstrated that the Fv regions dictate the apparent stabilities of the Fabs.

The DSC profile of the anti-HER2 mAb exhibited two transitions: a small peak having a Cp max of 27 Kcal/molePC and a Tm1 of 70.4° C., corresponding to the unfolding of the CH2 domain, and a large peak having a Cp max of 152 Kcal/molePC and a Tm2 of 80.4° C., corresponding to the unfolding of both CH3 and Fab domains. The DSC profile of the anti-EGFR mAb exhibited two transitions: a large peak having a Cp max of 95 Kcal/molePC and a Tm1 of 71.9° C., corresponding to the unfolding of both CH2 and Fab domains, and a small peak having a Cp max of 22 Kcal/molePC and a Tm2 of 82.4° C., corresponding to the unfolding of the CH3 domain.

The DSC profile of BiXAb-3489 also exhibited two transitions with two large peaks. The first peak had a Cp max of 70 Kcal/molePC and a Tm1 of 71.7° C., and corresponded to the unfolding of the CH2 and Fab domains of the anti-EGFR mAb; the second peak had a Cp max of 161 Kcal/molePC and a Tm2 of 80.9° C., and corresponded to the unfolding of the CH3 and Fab domains of the anti-HER2 mAb. Thus, the DSC profile of BiXAb-3489 resembled the superposition of the two DSC profiles of the two parental mAbs, and illustrated the excellent assembly and stability of BiXAb-3489. The Tonset of BiXAb-3489 (60.0° C.) was similar to that of the parental mAbs (anti-HER2 Tonset=63.1° C. and anti-EGFR Tonset=61.5° C.), indicating that BiXAb-3489 possessed stability properties similar to those of the parental antibodies.

Definitions

Tm or denaturation/melting temperature is the point at which the concentration of the unfolded and folded species is equal, and is the midpoint of the unfolding transition.

As a parameter, it describes the susceptibility of the protein to thermal denaturation, and thus it relates to the stability of the protein. The higher the Tm the more stable the protein.

Tonset is the temperature at which the unfolding transition begins. The values for this parameter are usually 5 to 10° C. lower than the Tm. It is also a parameter describing protein stability, but with relevance to the resistance to thermal denaturation.

Example 4. Cell Free Binding Properties

Dual Antigen-Binding ELISA Assay

100 µL of recombinant human Fc-tagged HER2 (Biotechne), at 2 µg/mL prepared by dilution with 1×PBS pH7.4, was used to coat Maxisorp plates at 4° C. overnight. The plates were washed 5 times with 1×PBST, and then blocked with 200 µL/well 1% BSA in 1×PBS at room temperature for 2 hrs. The plates were washed 5 times with 1×PBST. An eight-point three-fold dilution series in 1×PBS of BiXAb-3486 and BiXAb-3489 (starting at 2 µg/mL) were prepared, and 100 µL of each dilution step was added per assay well. The plates were incubated at room temperature for 1 hr, and subsequently washed 5 times with 1×PBST. 100 µL/well of 1 µg/mL biotinylated human EGFR (AcroBiosystems) in 1×PBS was added, and the plates were incubated at room temperature for 1 hr. After 5 washes with 1×PBST, 100 µL/well of 0.1 µg/mL of streptavidin-conjugated HRP (Biotechne) prepared by dilution with 1×PBS was added. The plates were incubated at room temperature for 1 hr. After 5 washes with 1×PBST, 100 µL/well of TMB substrate in 1×PBS was added for calorimetric readout, and the plates incubated for 10 min at room temperature for color development. The assay data were collected employing a Victor2 microplate reader (Perkin Elmer) at 650 nm.

Figure 5:
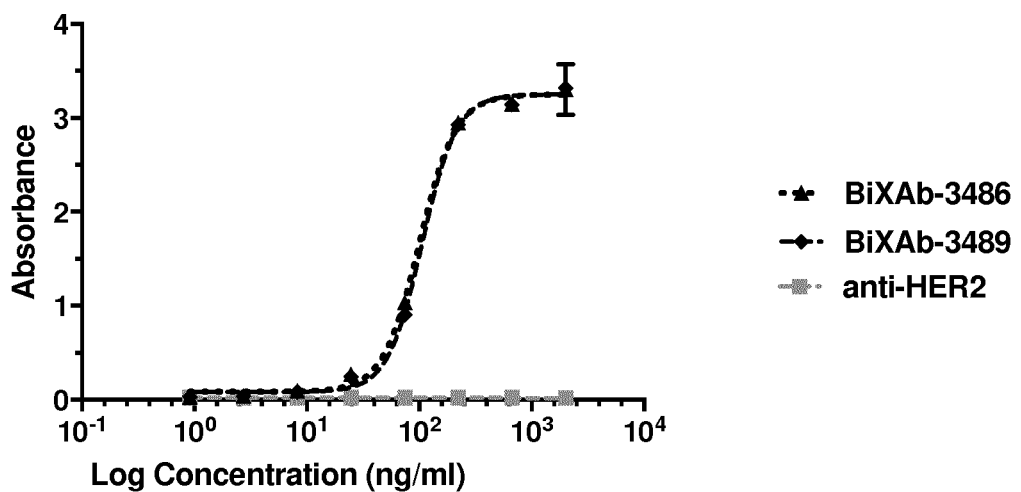
FIG. 5 shows the binding profile of BiXAb-3486 and BiXAb-3489 in a dual antigen (HER2 and EGFR) binding ELISA.

BiXAb-3486 and BiXAb-3489 exhibited overlapping dose-dependent binding curves in the dual ELISA format, suggesting that they possessed correctly assembled anti-HER2 and anti-EGFR Fab domains (FIG. 5). This demonstrated that both BiXAb-3486 and BiXAb-3489 are bispecific antibodies capable of binding HER2 and EGFR simultaneously with EC50 of 100 ng/mL and 106 ng/mL, respectively. Parental anti-HER2 exhibited no binding in this dual ELISA format, as expected.

Example 5. Determination of Binding Parameters by SPR

SPR spectroscopy was conducted on a T200GxP instrument (Biacore, GE Healthcare). As running Buffer HBS-EP+ pH7.4 (Diluted from 10×HBS-EP+ supplied by GE Healthcare) was used. The measurements were conducted at 25° C. as recommended by the manufacturer. All experiments were conducted at a flow rate of 30 µL/min. Since protein A capture can lead to impaired ligand binding affinity in case of Trastuzumab, a human Fab-specific capture was chosen. Therefore a CM5-S-Series sensor chip (GE Healthcare) was employed for antibody capture using the Human Fab Capture Kit (GE Healthcare) according to the manufacturer's instructions (Rimmob~10 000 RU) by EDC-NHS chemistry using the Amine Coupling Kit (GE Healthcare). Flow cell one (Fc 1) was activated and deactivated to be used as a reference for blank subtraction. The surface was regenerated between the measurement cycles by pulsing for 45 sec with the recommended regeneration buffer (10 mM glycine-HCl pH 2.1 supplied within the Human Fab Capture Kit). Buffer injections were used for double referencing.

For the determination of binding parameters of BiXAb-3489 and BiXAb-3732SS, and their parental anti-EGFR and anti-HER2 mAbs, to hEGFR (EGR-H5222, Acro Biosystems) and hHER2 (HE2-H5225, Acro Biosystems), approximately 100 RU of analyte (a mAb or a BiXAb) was captured by injecting an appropriate dilution of each respective molecule in running buffer for 180 sec, followed by an injection of either hEGFR (20 nM) or hHER2 (20 nM) for 180 sec, followed by a 300s dissociation phase. Affinity constants were determined through fitting the resulting sensograms with the BiacoreEval 3.0 software after performing double-referencing using the Biocore T200 evaluation software. A 1:1 binding model was used together with experimentally determined RMax as fixed parameter to determine association rate constant (ka), dissociation rate constant (kd), and equilibrium dissociation constant (KD).

The affinity constants for the interaction of anti-EGFR and anti-HER2 parental mAbs and BiXAb-3489 and BiXAb-3732SS with cognate ligands, EGFR and HER2, were determined by fitting single concentration curves using a 1:1 interaction model. In general very similar KD values in the low nanomolar range were observed (Table 3). Two-fold deviations are expected when measuring high affinities, so differences of up to 50% should not be considered as relevant. It is conceivable that anti-HER2 Fabs in BiXAb-3732SS exhibit a slightly faster kd for the "reverse" series; nevertheless, this is inconsistent with steric hindrance of interior Fab domains since in that case kon would have been reduced.

In conclusion, the properties of anti-HER2 and anti-EGFR Fab domains were very similar in both BiXAb-3489 and BiXAb-3732SS, independent of whether they were located proximal or distal to the Fc domain, and were similar to corresponding parental antibodies (anti-EGFR and anti-HER2). Therefore, Fab binding of cognate antigens, EGFR and HER2, in the BiXAb molecule is not sterically hindered.

TABLE 3

Binding parameters determined by SPR analysis.

| Antibody | Ka $10^5$ [M$^{-1}$s$^{-1}$] | Kd $10^{-4}$ [s$^{-1}$] | KD [nM] |
|---|---|---|---|
| Anti-EGFR (parental) | 5.40 | 16.61 | 3.08 |
| BiXAb-3489 | 5.97 | 14.17 | 2.37 |
| BiXAb-3732SS | 8.45 | 16.84 | 1.99 |
| Anti-HER2 (parental) | 2.02 | 3.53 | 1.75 |
| BiXAb-3489 | 1.88 | 2.95 | 1.57 |
| BiXAb-3732SS | 1.42 | 7.76 | 5.48 |

Example 6. Antibody Dependent Cell-Mediated Cytotoxicity (ADCC) with Unfractionated Non-Preactivated Mononuclear Cells (MNC)

BxPC3 pancreatic cancer cells, A431 skin squamous carcinoma, SKOV-3 ovarian cancer cells were cultured in RPMI 1640-Glutamax-I medium, supplemented with 100 μg/ml penicillin, 100 μg/ml streptomycin, and 10% fetal calf serum.

For preparation of MNC the following procedure was employed. Freshly drawn peripheral blood was anti-coagulated with citrate. Subsequently, 5 ml of Ficoll-Paque PLUS solution was layered with 6 ml anti-coagulated whole blood. Samples were centrifuged for 20 min at 2,500 rpm at RT with no subsequent centrifuge breaking. MNC were collected from the plasma/Ficoll interface. The MNC cell suspension was diluted 1:10 in PBS and centrifuged for 5 minutes at 1,800 rpm at room temperature. The supernatant was removed, and the erythrocytes were lysed by addition of 45 ml ice-cold distilled water to the cell suspension for 30 seconds, after which 5 ml of 10×PBS was added. The cells were centrifuged for 5 min at 1800 rpm at room temperature and washed with 1×PBS three times to remove platelets. Finally cells were re-suspend in 5 ml cell culture medium. Cell numbers were adjusted to achieve 40:1=Effector cell: Tumor cell ratio in the ADCC assays, which corresponded to 8:1=NK cell: Tumor cell ratio, when calculated based on the fraction of NK cells in MNC.

For the ADCC $^{51}$Chromium release assay, $1\times10^6$ target cells (BxPC-3, A541, A431) were incubated with 100 μCi 51Chromium in 200 μl PBS for 2 hours at 37° C. and 5% CO2. After 2 hours incubation, cells were washed three times with 7 ml of medium and finally re-suspended at a concentration of 0.1×106 cells/ml. Target cells (5,000 cells/well) and MNC in the presence of antibodies were incubated in a 96-well micro-titer plate (200 μl assay volume) for 4 hours at 37° C. and 5% CO2. For the determination of maximal target cell lysis (=maximal cpm) Triton X-100 was added. To determine basal $^{51}$Chromium release (=basal cpm) target cells were not further manipulated. After 4 hr incubation, micro-titer plates were centrifuged for 5 min at 2000 rpm and 25 μl supernatant was mixed with 125 μl of Optiphase Supermix (Perkin Elmer) and incubated in a shake incubator for 1 min. Samples were assayed in a MicroBeta TriLux (Perkin Elmer) beta-counter instrument. Target cell lysis was calculated using the following formula:

% lysis=(experimental cpm−basal cpm)/(maximal cpm−basal cpm)×100.

All of the measurements were performed in triplicate. ADCC assays were performed employing non-pre-activated MNC as effector cells.

Figure 6A:
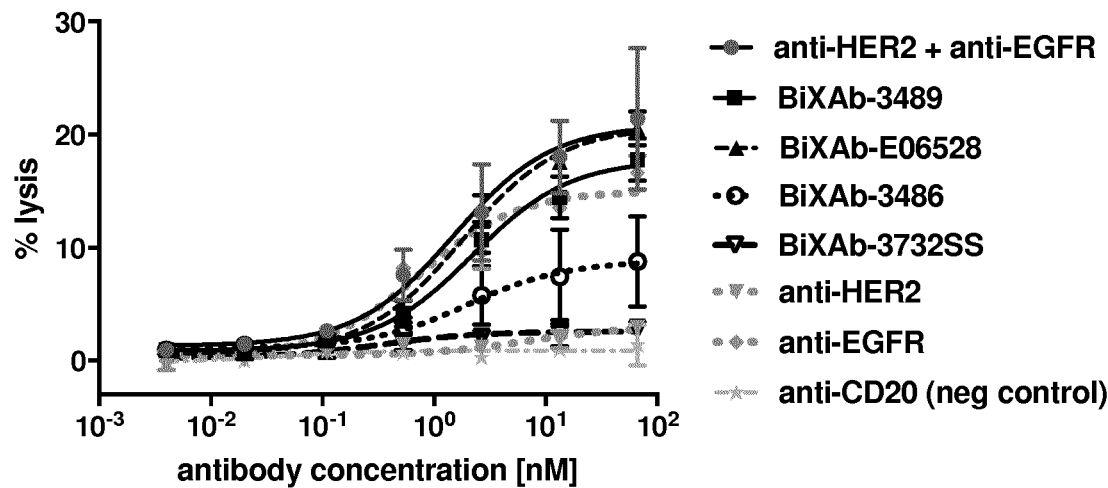
FIG. 6A shows the cytotoxic activity profiles of the two parental antibodies (anti-HER2 and anti-EGFR), their 1:1 mixture, BiXAb-3486, BiXAb-3489, BiXAb-3732SS, BiXAb-E06528, and a negative control antibody, anti-CD20, in an ADCC assay employing a human pancreatic cancer cell line, BxPC-3, as target cells and unfractionated non-pre-activated mononuclear cells as effector cells.
Figure 6B:
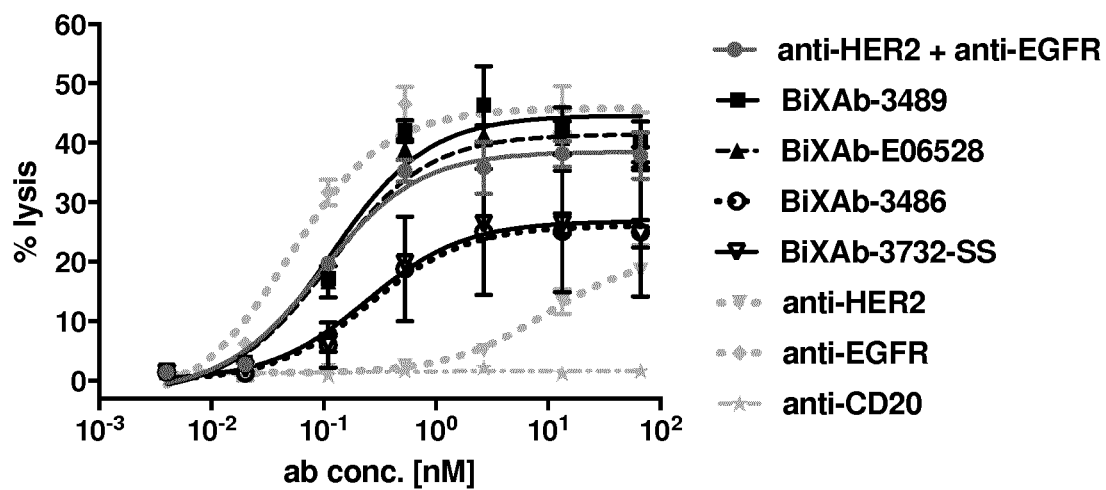
FIG. 6B shows the cytotoxic activity profiles of the two parental antibodies (anti-HER2 and anti-EGFR), their 1:1 mixture, BiXAb-3486, BiXAb-3489, BiXAb-3732SS, BiXAb-E06528, and a negative control antibody, anti-CD20, in an ADCC assay employing a human skin squamous carcinoma cell line, A431, as target cells and unfractionated non-pre-activated mononuclear cells as effector cells.
Figure 6C:
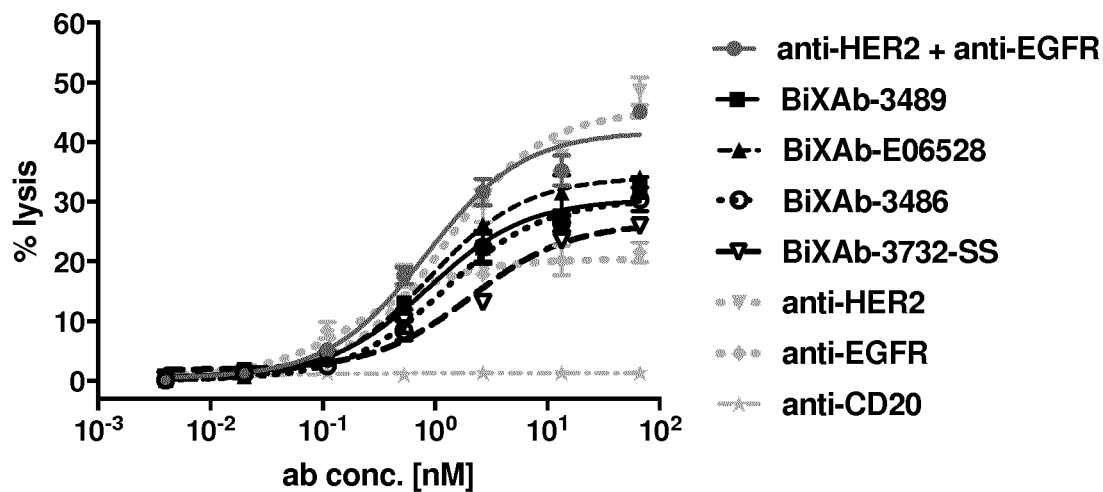
FIG. 6C shows the cytotoxic activity profiles of the two parental antibodies (anti-HER2 and anti-EGFR), their 1:1 mixture, BiXAb-3486, BiXAb-3489, BiXAb-3732SS, BiXAb-E06528, and a negative control antibody, anti-CD20, in an ADCC assay employing a human ovarian cancer cell line, SKOV3, as target cells and unfractionated non-pre-activated mononuclear cells as effector cells.

In FIG. 6A ADCC assay with BiXAb-3486, BiXAb-3489, BiXAb-3732SS, and BiXAb-E06528 on BxPC-3 cells is presented. Potent cytotoxicity was observed for BiXAb-E06528 (EC50=1.8 nM) and BiXAb-3489 (EC50=2.2 nM), which was similar to that of the combination of both parental antibodies, anti-EGFR+anti-HER2 (EC50=1.5 nM); maximal lysis was nearly identical for all three antibody groups~20%. BiXAb-3486 demonstrated similar potency of killing (EC50=2.0 nM) albeit with much reduced total lysis of <10%. BiXAb-3732SS exhibited almost no lysis, similar to that of parental anti-EGFR antibody. Parental anti-EGFR antibody exhibited high potency (EC50=0.8 nM), however total lysis was reduced (15%) relative to BiXAb-E06528, BiXAb-3489, and the combination of both parental antibodies, anti-EGFR+anti-HER2. Similarly, BiXAb-E06528 (EC50=0.12 nM) and BiXAb-3489 (EC50=0.12 nM) displayed similar maximal lysis and very high potency against A431 cells as the combination of parental anti-EGFR+anti-HER2 (EC50=0.09 nM) and anti-EGFR alone (EC50=0.05 nM) (FIG. 6B). BiXAb-3486 and BiXAb-3732SS again demonstrated reduced potency (EC50=0.26 nM and EC50=0.24 nM, respectively) and reduced maximal lysis. ADCC on SKOV-3 cells demonstrated that BiXAb-E06528 (EC50=0.87 nM) and BiXAb-3489 (EC50=0.87 nM) and the combination of parental anti-EGFR+anti-HER2 (EC50=0.83 nM) and anti-HER2 (EC50=1.2 nM) were potently killing cancer cells (FIG. 6C), however the maximal lysis of both BiXAb molecules was slightly reduced relative to combination or anti-HER2 alone. BiXAb-3486 and BiXAb-3732SS exhibited slightly reduced cytotoxic potency (EC50=1.2 nM and EC50=2.1 nM) and maximal lysis. In conclusion, all BiXAbs demonstrated cytotoxic activity against several different types of EGFR/HER2* cancer cells, and BiXAb-E06528 and BiXAb-3489 exhibited the highest cytotoxic potency and maximal lysis against these cancer cell lines.

Example 7. Evaluation of Effects on Viability of Cancer Cell Lines

NCI-N87 human gastric carcinoma and CAL27 human tongue squamous cell carcinoma cell lines were grown as monolayer at 37° C. in a humidified atmosphere (5% CO2, 95% air) in their culture media (RPMI1640+10% FBS and DMEM+10% FBS, respectively). For experimental use, tumor cells were detached from the culture flask by a 5-minute treatment with trypsin-versene and neutralized by addition of complete culture medium. The cells were counted in a hemocytometer (KOVA slide) following supplier's instructions and their viability was assessed by 0.25% trypan blue exclusion.

To evaluate antibody effects on viability of cancer cell lines optimal cell line density, 111 000 cells/mL in 96-well flat-bottom microtiter plates, was used. They were incubated at 37° C. for 24 hours before treatment in drug-free RPMI 1640 medium supplemented with 10% FBS. Volumes for seeding were 90 µl. Compounds were tested in triplicates in one independent experiment.

At treatment start, a volume of 10 µL of the test and control substance dilutions were added to wells to reach the following final concentrations:

For test and control substances concentrations were equal to 190; 100; 50; 25 and 10 µg/mL
For the combination of anti-HER2+anti-EGFR antibodies concentrations of both anti-EGFR and anti-HER2 were equal to 140; 100; 50; 25 and 10 µg/mL.

Cells were incubated in triplicate for 96 hours in a 100 µL final volume of culture medium containing test substances at 37° C. under 5% CO2.

The effect of the compounds on the viability of cancer cells was revealed by CellTiter-Glo luminescent assay kit (Promega) according to manufacturer's instructions after 96 h hours of compound incubation. Briefly, 100 µL of CellTiter Glo reagent was prepared and added in each well. Plates were then shaken to induce cell lysis before recording luminescence.

The dose response inhibition of survival (IC) was expressed as following:

$$IC = 100 \times (OD_{drug\text{-}exposed\ wells} / OD_{vehicle\text{-}exposed\ wells})$$

The OD values were the mean of 3 experimental measurements.

BiXAb-E06528 and BiXAb-3489 potently inhibited viability of NCI-N87 with IC50 of 102.6 g/mL and 50.2 µg/mL, respectively. The combination of anti-EGFR+anti-HER2 antibodies did not reach the 50% viability inhibition level and the IC50 was estimated to be >140 µg/mL. Individual preparations of parental anti-EGFR or anti-HER2 were minimally active in the concentration range tested and also did not reach the 50% viability inhibition level; therefore both IC50 were estimated to be >190 µg/mL.

CAL27 was also efficiently inhibited by BiXAb-E06528 and BiXAb-3489, which inhibited its viability at the lowest concentration by ~60% and thus the IC50 for both molecules was estimated to be <10 µg/mL. The combination of two parental antibodies, anti-EGFR+anti-HER2, inhibited viability with IC50=10.5 µg/mL. The individual preparation of parental anti-EGFR mAb exhibited much lower degree of inhibition with IC50=93.1 µg/mL; the individual preparation of parental anti-HER2 mAb demonstrated no inhibition in the tested range of concentrations.

In conclusion, both BiXAb-E06528 and BiXAb-3489 demonstrated potent inhibition of viability of gastric and tongue squamous cell carcinomas, which was more potent than that of either of the two parental antibodies or their combination.

Example 8: Evaluation of the Biological Properties of the Antibodies of the Invention The original bispecific tetravalent antibodies of the invention, which target simultaneously EGFR and HER2 receptor in an original way has been evaluated in mice bearing the pancreatic tumor BxPC-3 and compared to the combination of anti-EGFR and anti-HER2 parental antibodies.

The bispecific tetravalent antibodies of the invention BiXAb-3486 and BiXAb-3489 were used for the assays.
Treatment Schedule The BxPC-3 cell line was obtained from the ATCC (Rockville, MD) and cultured in RPMI 1640 containing 10% fetal calf serum, 50 U/ml penicillin, and 50 µg/ml streptomycin.

All in vivo experiments were performed in compliance with the French regulations and ethical guidelines for experimental animal studies in an accredited establishment.

Six week-old nude female athymic mice, purchased from Harlan (Le Malcourlet, France), were injected subcutaneously into the right flank with BxPC-3 ($3.5 \times 10^6$) cells.

Tumor-bearing bearing detectable growing tumors were then distributed in the various groups. Animals were treated with intraperitoneal (ip) injections according to the following schedules after tumors reached the predefined volume of 100 mm$^3$:

Control mice received an irrelevant antibody from the day the animals were randomized and enrolled into 6 cohorts (day 0), twice a week, up to day 28.
C+T mice received anti-EGFR+anti-HER2 antibodies, each at 2 mg/kg from day 0, twice a week, up to day 28.
BiXAb mice received the bispecific antibodies according to the following protocols:
BiXAb-3486 at 2 mg/kg from day 0, twice a week up to day 28
BiXAb-3486 at 10 mg/kg from day 0, twice a week up to day 28
BiXAb-3489 at 2 mg/kg from day 0, twice a week up to day 28
BiXAb-3489 at 10 mg/kg from day 0, twice a week up to day 28

Criteria for Assessing Antitumor Activity

Safety (body weight, survival, clinical signs, and behavior) and tumor growth as a biomarker for efficacy were taken as major end-points for follow-up and recorded for all mice twice a week throughout the course of the experiment. Graphs and analysis were performed by the Newlab Oncology Software.

Tumor Volume

Tumor dimensions were measured with a caliper and the volume calculated by the formula $D_1 \times D_2 \times D_3/2$, and various endpoints were evaluated to assess the efficacy of treatments.

Tumor Growth Inhibition

Tumor growth inhibition (T/C %), defined as the ratio of the median tumor volume for the treated vs. control group was calculated as T/C %=[(median tumor volume of treated group at day X)/(median tumor volume of control group at day X)]×100. The optimal value is the minimal T/C % ratio reflecting the maximal tumor growth inhibition achieved.

The effective criteria for the T/C % ratio according to the National Cancer Institute standard (Bissery M C and Chabot G G History and new development of screening and evauation methods of anticancer drugs used in vivo and in vitro. 1991. Bull Cancer 78:587-602) is <42%. T/C<10% is considered very high activity that merits a clinical study (B. A. Teicher. Tumor models in cancer research. Science & Business media 2010).

In this experiment, T/C was evaluated all along the experiment, from day 1 up to day 49.

ΔT/ΔC

Changes from baseline of tumor volume in treated and control groups were used to calculate the median in treated (ΔT) and control (ΔC) groups. T/C (%) is the ratio of median at any chosen day.

When ΔT/ΔC values are negative, it indicates regressions of tumors.

Partial Regression, Complete Regression and Tumor Free Survivors

Partial regression (PR) was defined as a decrease in tumor volume≥50%, whatever the day of evaluation. Complete regression (CR) is defined as a decrease in tumor volume below the limit of palpation (T=30 mm$^3$), whatever the day of evaluation. At study end (day 105), the number of tumor-free survivors (TFS), which correspond to mice without any palpable tumor, was determined (Vrignaud P, Sémiond D, Lejeune P, Bouchard H, Calvet L, Combeau C, Riou J F, Commergon A, Lavelle F, Bissery M C. Preclinical antitumor activity of cabazitaxel, a semisynthetic taxane active in taxane-resistant tumors. Clin Cancer Res. 2013; 19 (11):2973-83).

Log Cell Kill (LCK)

Gross Log cell kill was calculated using the formula (T−C)/(3.32×Td). In this formula, tumor growth delay (T−C) was defined as the difference between tumors in the T and C groups in the median time (days) to reach a predetermined volume (750-1,000 mm$^3$).

The tumor doubling time (Td) was estimated in the control group, where the log of the tumoral volume as a function of day (in the exponential growth phase, i.e. 100 to 1000 mm$^3$ range) follows a linear model with slope "a", as Td=log 2/a.

Using these criteria, antitumor activity is defined as a log cell kill value >0.7.

The Southern Research Institute (Birmingham, AL, USA) score was used to categorize antitumor activity based on log cell kill values as follows: <0.7=−(inactive); 0.7-1.2=+; 1.3-1.9=++; 2.0-2.8=+++; >2.8=++++(highly active) (Schabel F M, Griswold D P, Laster W R, Corbett T H, Lloyd H H. Quantitative evaluation of anticancer agent activity in experimental animals. Pharmacol. Ther 1977; 1:411-35).

Net LCK was also evaluated according to the following formula: n−LCK=[(T−C)—duration of treatment period]/(3.32×Td). If n−LCK-net values are positive, there are fewer cells present at the end of therapy than at the start. If, on the other hand, the value is negative, the tumor grows under treatment.

Median Survival and Therapeutic Benefit

The results were also expressed by an adapted Kaplan-Meier survival curve, using the time taken for the tumor to reach a determined volume of 2000 mm$^3$. A median delay was defined as the time at which 50% of the mice had a tumor reaching the determined volume.

Mann-Whitney U Test

The Mann-Whitney test is a nonparametric test that allows two groups or conditions or treatments to be compared without making the assumption that values are normally distributed. In medicine, it is used to determine the effect of two medicines and whether they are equal or not. The Mann-Whitney U test has been evaluated with the Newlab Oncology software (NewLab, 11 rue d'Amsterdam 54500 Vandceuvre-Lès-Nancy FRANCE).

Drug Toxicity

Both drug-related deaths and maximum percent relative mean net body weight loss were also determined. A body weight loss nadir (mean of group) >20% or 10% drug deaths were considered to indicate an excessive toxic dosage.

The pancreatic tumor BxPC-3 was already observed to express high level of EGFR receptors, and in this tumor, the anti EGFR monoclonal Ab cetuximab was observed to be significantly active. Contrary, this tumor expresses very low level of Her2 (Larbouret C, et al. In pancreatic carcinoma, dual EGFR/HER2 targeting with cetuximab/trastuzumab is more effective than treatment with trastuzumab/erlotinib or lapatinib alone: implication of receptors' down-regulation and dimers' disruption. Neoplasia. 2012 February; 14(2): 121-130) and as a consequence, the anti HER2 monoclonal antibody Trastuzumab, was not significantly active.

Interestingly, the combination of both Abs creates a significant higher activity than that as detected with cetuximab.

In this experiment, the activity of the bispecific tetravalent antibodies of the invention, BiXAb-3486 and BiXAb-3489, was compared with the combination of parental anti-EGFR and anti-HER2 antibodies in mice bearing the BxPC-3 tumor and no toxic effect was detected all along the study.

Mice bearing BxPC-3 cells were treated twice a week with IP anti-EGFR and anti-HER2 antibodies, from day 0, day of randomization, to day 28 for each antibody at 2 mg/kg/injection. A 2 mg/kg dose was chosen on the basis of previous experiments. The two bispecific antibodies of the invention were also given under the same schedule of treatment either at 2 or at 10 mg/kg/injection (FIG. 7a).

Tumors grew in the vehicle-treated mice with a doubling time of 9 days and reached a mean value of 1859+/−459 mm$^3$ on day 28, the last day of treatment. On that day, the tumor mean volume was 634 mm$^3$ for the group of mice treated with the combination of anti-EGFR and anti-HER2 antibodies at a 2 mg/kg dose. For the groups treated with BiXAb-3486 at 2 or 10 mg/kg, the tumor mean volumes were only 214 mm$^3$ and 111 mm$^3$, and 223 mm$^3$ and 200 mm$^3$ for the groups treated with BiXAb-3489 at 2 or 10 mg/kg.

The T/C and ΔT/ΔC evaluations (FIG. 7b) indicate that:
All treatments were active with T/C<42% according to NCI criteria.
Only groups of mice treated with BiXAb-3486 or BiXAb-3489 demonstrated a very high activity (T/C<10%), whereas mice treated with anti-EGFR and anti-HER2 antibodies experienced a moderate activity.

The very high activity is maintained after the end of treatment (after day 28)

Partial or total regressions (defined as a decrease in tumor volume≥50% or a decrease in tumor volume below the limit of palpation) and cures were monitored all along the experiment (table 4). A total of 6/10 and 3/10 animals experienced respectively complete regressions and cures in the group of mice treated with BiXAb-3486 at 10 mg/kg, indicating a potent activity.

TABLE 4

Regressions and cures

| Groups | Partial regressions | Complete regressions | Total regressions (%) | Tumor-free survivors at day 1010 |
|---|---|---|---|---|
| BiXAb-3486 at 2 mg/kg | 2/10 | 3/10 | 50% | 0/10 |
| BiXAb-3486 at 10 mg/kg | 2/10 | 6/10 | 80% | 3/10 |
| BiXAb-3489 at 2 mg/kg | 1/9 | 3/9 | 44% | 0/10 |
| BiXAb-3489 at 10 mg/kg | 2/9 | 3/9 | 56% | 0/10 |
| anti-EGFR + anti-HER2 antibodies at 2 mg/Kg | 0/9 | 0/9 | 0% | 0/9 |
| Control | 0/8 | 0/8 | 0% | 0/8 |

Exponential growth and its associated concept of the doubling time are clinically relevant (Frei E III. Models and the clinical dilemma. In: Fidler I J, White R J, editors. Design of models for testing therapeutic agents. New York: Van Nostrand Reinhold; 1982. p. 248-59). Different histologic types of cancer display a great variety of doubling times within the observable range of tumor sizes (Shackney S E, McCormack G W, Guchural G J Jr. Growth rate patterns of solid tumors and their relation to responsiveness to therapy. An analytical review. Ann Intern Med. 1978; 89:107).

The most therapeutically responsive human cancers, such as testicular cancer and choriocarcinoma, tend to have doubling times that are <1 month long. Less responsive cancers, such as squamous cell cancer of the head and neck, seem to double in about 2 months. The relatively unresponsive cancers, such as colon adenocarcinoma, tend to double every 3 months. Clearly, this clinical observation may relate to the higher chemosensitivity of proliferating cells (see below), that is, if a tumor has a high fraction of dividing cells, it will tend to grow faster and will also tend to be more responsive to drugs that kill dividing cells. Alternatively, tumors with a higher rate of cell loss tend to have a relatively slower growth rate and also a higher rate of mutations toward drug resistance.

The log cell kill model proposes that anticancer drugs act with first-order kinetics, and hence, assuming homogeneous sensitivity to the drug, they will eliminate a constant proportion rather than a constant number of tumor cells regardless of the initial size of the tumor. In other words, if a drug treatment reduces $10^6$ cells to $10^5$, the same therapy would reduce $10^4$ cells to 103.

In the experiment, we observed that the doubling time of the tumors in the control group was 7 days (FIG. 7a).

According to gross Log cell kill calculation [(T–C)/(3.32×Td)] and net Log cell kill calculation [(T–C)—duration of treatment period]/(3.32×Td) (Table 5), it appears that the combination of anti-EGFR and anti-HER2 antibodies was globally not active and that tumors grew under treatment.

Contrary, mice treated with BiXAb-3486 or BiXAb-3489 experienced a significant activity (++ or +++) and up to 2 logs (99%) of the initial tumor mass was eliminated by BiXAb compounds. The net log cell kill calculation, which is positive, indicates that treatments with BiXAb compounds were efficient and that there are fewer tumor cells at the end of treatment (day 28) compared to before the treatment (day 0).

TABLE 5

Gross and Net Log cell kill evaluation

| Treatments | Dosage (mg/kg/injection) | Gross Log cell kill | Net Log cell kill | Antitumor activity | General comments |
|---|---|---|---|---|---|
| Control C + T | | 0.7 | <0 | + | Modest activity Growth under treatment |
| BiXAb-3486 | 2 | 1.32 | 0.13 | ++ | Active compounds |
| | 10 | 2.00 | 0.77 | +++ | |
| BiXAb-3489 | 2 | 1.33 | 0.13 | ++ | |
| | 10 | 1.55 | 0.34 | ++ | |

The median survival, the days after the graft, when 50% of mice possess tumors with the volume of 2000 mm³ and therapeutic benefit (median of treated groups—median of the control group) (FIGS. 7C and 7D), indicate a clear therapeutic advantage of the BiXAb therapy relative to the combination of two monoclonal antibodies therapy.

Finally, a Mann-Whitney U test was performed in order to compare the four groups of animals treated with the BiXAb compounds with the group treated with the combination of anti-EGFR and anti-HER2 antibodies (Table 6).

TABLE 6

Mann-Whitney U test (BiXAb groups vs. anti-EGFR + anti-HER2 group)
Groups Vs anti-EGFR + anti-HER2 (p value Mann-Whitney U test)

| | Days | | | | | | | |
|---|---|---|---|---|---|---|---|---|
| | 1 | 7 | 10 | 14 | 21 | 28 | 35 | 42 | 49 |
| BiXAb-3486 at 2 mg/kg | 0.5 | 0.1844 | 0.2838 | 0.035 | 0.0045 | 0.0057 | 0.0035 | 0.0137 | 0.0362 |
| BiXAb-3486 at 10 mg/kg | 0.4191 | 0.0826 | 0.0652 | 0.0035 | 0.0009 | 0.001 | 0.003 | 0.001 | 0.005 |
| BiXAb-3489 at 2 mg/kg | 0.4299 | 0.4475 | 0.2829 | 0.0425 | 0.0121 | 0.0122 | 0.0096 | 0.019 | 0.0153 |
| BiXAb-3489 at 10 mg/kg | 0.3619 | 0.4824 | 0.3619 | 0.0425 | 0.019 | 0.0153 | 0.0005 | 0.0002 | 0.005 |

Treatment period

Once again, it appears clearly that groups treated with BiXAb compounds experienced a higher activity than the group treated with the combination of anti-EGFR and anti-HER2 antibodies. This difference was also observable 21 days after the end of the treatments.

In fact, several endpoints that are classically used for the antitumor evaluation of cytotoxic compounds were used. It appeared that the two bispecific antibodies of the invention are more potent than the combination of anti-EGFR and anti-HER2 antibodies.

1) T/C<10% is only obtained with the two bispecific antibodies of the invention a parameter which is required by NCI for classification into highly active compounds, that merits a clinical study;
2) Log cell kill parameters (Gross and Net) and their translations into activity rating also confirm that the two bispecific antibodies of the invention were more active than the combination of anti-EGFR and anti-HER2 antibodies;
3) Regression, which is the hallmark of potent activity was only observed in groups treated with two bispecific antibodies of the invention.

Conclusion: In Examples 6 and 7 we evaluated individual mechanisms of action (MOA) that are frequently associated with therapeutic activity of antibodies. In Example 6 we tested antibody-dependent cell-mediated cytotoxicity (ADCC) on three different cell lines. The two BiXAb molecules, BiXAb-E06528 and BiXAb-3489, demonstrated cell-mediated cytotoxicity similar to that of the combination of two parental antibodies, anti-EGFR+anti-HER2. Some variability observed in the assays may be due to the different ratio of EGFR/HER2 on target cancer cells. In Example 7 we tested "direct" effects of antibodies, i.e. their ability to block pro-proliferative signaling via EGFR, HER2 and heterodimers associated with these receptors, which has the effect on reducing the viability of cancer cell lines. These experiments demonstrated that BiXAb-E06528 and BiXAb-3489 display a substantially higher anti-proliferative activity than that associated with each of the parental antibodies individually (anti-EGFR, anti-HER2) or their combination (anti-EGFR+anti-HER2). This means that both BiXAbs exhibit much stronger ability to inhibit proliferation and growth than that associated with parental antibodies. In Example 8 we tested BiXAb-3489 and BiXAb-3486 in vivo in a xenograft model of pancreatic cancer. This model demonstrated a surprising increase in tumor growth inhibition associated with the BiXAbs compared to the combination of 2 parental antibodies.

In the in vivo model we were capable of evaluating the sum of all MOA that are relevant for activity of a drug; in this case this means that both immune cell-mediated cytotoxicity and direct effect of inhibition of proliferation are contributing to the outcome of the xenograft model. The bispecific antibodies of the invention demonstrated potency, which is rarely observed with pancreatic tumors.

Since the in vivo model reflected a substantially improved activity of BiXAbs relative to that of the combination of both parental antibodies, we conclude that direct inhibition of pro-proliferative signaling in tumors is providing a major contribution to activity of the BiXAbs in inhibiting the growth of tumors and extending the survival of the animals (Example 8).

The invention claimed is:

1. A bispecific antibody comprising two heavy chains and four light chains, wherein each heavy chain comprises:
   a) a Fc region of an immunoglobulin comprising Hinge-CH2-CH3 domains,
   b) which Fc region is linked to Fab heavy chain CH1-VH of antibody 1 (Ab1) by said Hinge domain,
   c) which is linked to Fab heavy chain CH1-VH of antibody 2 (Ab2), by a polypeptide linker sequence, wherein the polypeptide linker sequence links the N-terminus of said Fab heavy chain VH domain of Ab1 with the C-terminus of said CH1 domain of Ab2,
   and the four light chains comprise Fab light chains CL-VL of Ab1 and Fab light chains CL-VL of Ab2 paired with their cognate heavy chain domains;
   wherein one of Ab1 or Ab2 comprises a VH domain comprising a heavy chain CDR1 comprising amino acids 26-33 of SEQ ID NO: 4, a heavy chain CDR2 comprising amino acids 51-57 of SEQ ID NO: 4 and a heavy chain CDR3 comprising amino acids 96-108 of SEQ ID NO: 4 and a VL domain comprising a light chain CDR1 comprising amino acids 27-32 of SEQ ID NO: 13, a light chain CDR2 comprising amino acids 50-52 of SEQ ID NO: 13, and a light chain CDR3 comprising amino acids 89-97 of SEQ ID NO: 13, and the other of Ab1 or Ab2 comprises a VH domain comprising a heavy chain CDR1 comprising amino acids 26-33 of SEQ ID NO: 1, a heavy chain CDR2 comprising amino acids 51-58 of SEQ ID NO: 1 and a heavy chain CDR3 comprising amino acids 97-109 of SEQ ID NO: 1 and a VL domain comprising a light chain CDR1 comprising amino acids 27-32 of SEQ ID NO: 10, a light chain CDR2 comprising amino acids 50-52 of SEQ ID NO: 10, and a light chain CDR3 comprising amino acids 89-97 of SEQ ID NO: 10.

2. The bispecific antibody of claim 1, wherein Ab1 or Ab2 comprises:
   a VH domain comprising SEQ ID NO: 4,
   a CH1 domain comprising a sequence selected from the group consisting of SEQ ID NO: 2, SEQ ID NO: 5, SEQ ID NO: 20, SEQ ID NO: 21 and SEQ ID NO: 22,
   a VL domain comprising SEQ ID NO: 13,
   a CL domain comprising a sequence selected from the group consisting of SEQ ID NO: 11, SEQ ID NO: 14, SEQ ID NO: 23, SEQ ID NO: 24 and SEQ ID NO: 25,
   wherein the CH1 and CL domains associate as follows:
   SEQ ID NO: 2 with SEQ ID NO: 11,
   SEQ ID NO: 5 with either SEQ ID NO: 14 or SEQ ID NO: 23,
   SEQ ID NO: 20 with either SEQ ID NO: 14 or SEQ ID NO: 23,
   SEQ ID NO: 21 with either SEQ ID NO: 24 or SEQ ID NO: 25,
   SEQ ID NO: 22 with either SEQ ID NO: 24 or SEQ ID NO: 25.

3. The bispecific antibody of claim 1, wherein Ab1 or Ab2 comprises:
   a VH domain comprising SEQ ID NO: 1,
   a CH1 domain comprising a sequence selected from the group consisting of SEQ ID NO: 2, SEQ ID NO: 5, SEQ ID NO: 20, SEQ ID NO: 21 and SEQ ID NO: 22,
   a VL domain comprising a sequence consisting of SEQ ID NO: 10,
   a CL domain comprising a sequence selected from the group consisting of SEQ ID NO: 11, SEQ ID NO: 14, SEQ ID NO: 23, SEQ ID NO: 24 and SEQ ID NO: 25,
   wherein the CH1 and CL domains associate as follows:
   SEQ ID NO: 2 with SEQ ID NO: 11,
   SEQ ID NO: 5 with either SEQ ID NO: 14 or SEQ ID NO: 23, SEQ ID NO: 20 with either SEQ ID NO: 14 or SEQ ID NO: 23,
SEQ ID NO: 21 with either SEQ ID NO: 24 or SEQ ID NO: 25,
SEQ ID NO: 22 with either SEQ ID NO: 24 or SEQ ID NO: 25.

4. The bispecific antibody of claim 1, wherein the sequences of the CH1 and CL domains of Ab1 are different from the sequences of the CH1 and CL domains of Ab2.

5. The bispecific antibody of claim 1, wherein the polypeptide linker sequence comprises SEQ ID NO: 3, SEQ ID NO: 16 or SEQ ID NO: 34.

6. The bispecific antibody of claim 1 which comprises:
a) two heavy chains, each comprising a continuous sequence comprising, in N- to C-terminus order:
VH domain comprising SEQ ID NO: 1,
CH1 domain comprising SEQ ID NO: 2,
the polypeptide linker sequence comprising SEQ ID NO: 3, SEQ ID NO: 16 or SEQ ID NO: 34,
VH domain comprising SEQ ID NO: 4,
CH1 domain comprising SEQ ID NO: 5,
Hinge domain comprising SEQ ID NO: 6,
CH2 domain comprising SEQ ID NO: 7,
CH3 domain comprising SEQ ID NO: 8,
b) two light chains, each comprising:
a VL domain comprising SEQ ID NO: 10,
a CL domain comprising SEQ ID NO: 11, or
c) two light chains, each comprising:
a VL domain comprising SEQ ID NO: 13,
a CL domain comprising SEQ ID NO: 14.

7. The bispecific antibody of claim 1, comprising:
a) two heavy chains, each comprising a continuous sequence comprising, in N- to C-terminus order:
VH domain comprising SEQ ID NO: 4,
CH1 domain comprising SEQ ID NO: 5,
the polypeptide linker sequence comprising SEQ ID NO: 3, SEQ ID NO: 16, or SEQ ID NO: 34,
VH domain comprising SEQ ID NO: 1,
CH1 domain comprising SEQ ID NO: 2,
Hinge domain comprising SEQ ID NO: 6,
CH2 domain comprising SEQ ID NO: 7,
CH3 domain comprising SEQ ID NO: 8,
b) two light chains, each comprising SEQ ID NO: 12; or
c) two light chains, each comprising SEQ ID NO: 15.

8. A polypeptide which comprises a heavy chain of the bispecific antibody as defined in claim 1 and contains SEQ ID NO: 5.

9. The bispecific antibody of claim 1, wherein the sequences of the CH1 and CL domains of Ab1 and Ab2, being different, are independently selected from:
a CH1 domain consisting of SEQ ID NO: 2 and a CL domain consisting of SEQ ID NO: 11; and
a CH1 domain consisting of SEQ ID NO: 5 and a CL domain consisting of SEQ ID NO: 14.

10. The bispecific antibody of claim 1, wherein the four light chains comprise Fab light chains of Ab1 and Fab light chains of Ab2 and are paired with their cognate heavy chain domains by inter-chain disulfide bonds.

* * * * *

UNITED STATES PATENT AND TRADEMARK OFFICE
CERTIFICATE OF CORRECTION

PATENT NO. : 12,054,550 B2
APPLICATION NO. : 16/096698
DATED : August 6, 2024
INVENTOR(S) : Eugene Zhukovsky et al.

It is certified that error appears in the above-identified patent and that said Letters Patent is hereby corrected as shown below:

In the Specification

Column 7,
Line 9, "chains: γ and κ" should read --chains: λ and κ--.

Column 17,
Line 40, "Gin (Q)" should read --Gln (Q)--.
Line 42, "Gin (Q)" should read --Gln (Q)--.
Line 56, "Gin (Q)" should read --Gln (Q)--.
Line 58, "Gin (Q)" should read --Gln (Q)--.

Column 23,
Line 6, "to Gin," should read --to Gln,--.
Line 17, "to Gin," should read --to Gln,--.
Line 57, "or Gin" should read --or Gln--.
Line 58, "a Gin" should read --a Gln--.

Column 34,
Line 41, "calorimetric" should read --colorimetric--.

Column 37,
Line 9, "EGFR/HER2*" should read --$EGFR^+/HER2^+$--.
Line 60, "102.6 g/mL" should read --102.6 µg/mL--.

Column 42,
Line 16, "to 103." should read --to $10^3$.--.

Signed and Sealed this
Twenty-first Day of October, 2025

John A. Squires
*Director of the United States Patent and Trademark Office*